United States Patent
Shapiro et al.

(10) Patent No.: US 9,115,122 B2
(45) Date of Patent: Aug. 25, 2015

(54) NON-ATP DEPENDENT INHIBITORS OF EXTRACELLULAR SIGNAL-REGULATED KINASE (ERK)

(71) Applicants: Paul S. Shapiro, Baltimore, MD (US); Alexander D. MacKerell, Jr., Baltimore, MD (US); Steven Fletcher, Baltimore, MD (US)

(72) Inventors: Paul S. Shapiro, Baltimore, MD (US); Alexander D. MacKerell, Jr., Baltimore, MD (US); Steven Fletcher, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 14/137,999

(22) Filed: Dec. 20, 2013

(65) Prior Publication Data

US 2014/0179743 A1   Jun. 26, 2014

Related U.S. Application Data

(60) Provisional application No. 61/740,156, filed on Dec. 20, 2012, provisional application No. 61/740,172, filed on Dec. 20, 2012.

(51) Int. Cl.
*A61K 31/44* (2006.01)
*C07D 277/00* (2006.01)
*C07D 417/06* (2006.01)
*C07D 277/34* (2006.01)

(52) U.S. Cl.
CPC ............ *C07D 417/06* (2013.01); *C07D 277/34* (2013.01)

(58) Field of Classification Search
None
See application file for complete search history.

(56) References Cited

U.S. PATENT DOCUMENTS 8,642,660 B2 *  2/2014  Goldfarb ................ 514/641
2004/0137472 A1 *  7/2004  Kole ...................... 435/6

FOREIGN PATENT DOCUMENTS

WO   WO 2004089276 A2 *  10/2004

OTHER PUBLICATIONS

CAPLUS 2011:1407166.*
The Merck Index 2001 edition, p. 573.*
Dains, F.B. et al., J. Amer. Chem. Soc. 1916, vol. 38, pp. 1841-1844.*
CAPLUS 2009:106690.*
CAPLUS 1977:165782.*
Xia, Z et al J. Med Chem 2009 vol. 52 pp. 74-86.*

* cited by examiner

*Primary Examiner* — Heidi Reese
(74) *Attorney, Agent, or Firm* — Nevrivy Patent Law Group P.L.L.C.

(57) ABSTRACT

A compound, having the formula A-1:

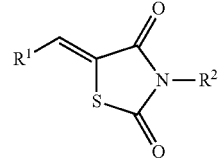

Wherein $R^1$ and $R^2$ are defined herein. Methods of using the compound and compositions containing the compound are provided.

4 Claims, 14 Drawing Sheets

Figure 10

| compound | ERK2 | ERK2 T157A | ERK2 D319N | T157A/ D319N | p38α | ERK2 selectivity | IC₅₀ A375 |
|---|---|---|---|---|---|---|---|
| SF-2-062 | 1.3±0.4 | 6.0±1.5 | 3.7±0.2 | 6.8±1.6 | 4.2±0.3 | 3.2 | 20 |
| SF-2-054 | 0.17±0.02 | 10.2±1.3 | 0.4±0.1 | 1.4±0.1 | 12.0±2.0 | 71.0 | 2 |
| SS-1-019 | 9.3±2.0 | ND | ND | ND | 8.3±1.4 | 0.9 | >100 |
| 76.3 | 1.5±0.1 | 8.1±0.8 | 13.4±0.6 | >20 | 4.5±0.9 | 3.0 | >100 |
| 76 | 5.0±0.3 | 6.1±0.6 | 7.0±1.0 | 6.4±0.3 | 7±1 | 1.4 | 30 |

Selective binding of DRS targeted lead compounds and inhibition of A375 melanoma cell proliferation. Compounds (0.01 – 20 µM) were tested for interactions with ERK2 wild type, DRS mutators, or p38α MAP kinase by FQ Binding ($K_D$) and proliferation (IC₅₀) data are in µM. Data show mean ± SD from 3-4 independent studies.

Structures of SF-2-054, SS-1-019 and SF-2-062.

NON-ATP DEPENDENT INHIBITORS OF EXTRACELLULAR SIGNAL-REGULATED KINASE (ERK)

CROSS-REFERENCE TO RELATED APPLICATIONS

This application claims the benefit of U.S. Provisional Appl. Nos. 61/740,156 and 61/740,172, both filed Dec. 20, 2012; the entire contents of each of which are hereby incorporated by reference.

STATEMENT OF FEDERALLY SPONSORED RESEARCH

This invention was made with government support under Grant No. R01 CA120215 awarded by the National Institutes of Health. The government has certain rights in the invention.

BACKGROUND

1. Field of the Application

The present application relates to inhibitors of extracellular signal-regulated kinase (ERK), compositions containing and methods for making same, and their use.

2. Discussion of the Background

Over the past decade, the inhibition of protein kinases has emerged as one of the most promising therapeutic approaches for treating cancer. Significant efforts in developing anti-cancer therapies have focused on the targeted inhibition of the extracellular signal-regulated kinase (ERK) pathway in cancers that contain activating mutations in upstream RTK, Ras and BRaf proteins. The usefulness of many of these targeted compounds has been limited, however, because of toxicity, lack of efficacy, and development of drug resistance through mutations or activation of alternate survival pathways. The identification of an activating point mutation (primarily V600E) in the BRaf kinase in melanoma patients led to the discovery of PLX4032 (vemurafenib), a drug which selectively inhibits the mutated and constitutively active form of BRaf. While patients showed remarkable initial responses to PLX4032, they invariably developed a resistance to the drug and consequently poor survival outcomes. A major contributor to PLX4032 drug resistance and poor prognosis is the re-activation of the extracellular signal-regulated kinases (ERK). Currently, all small molecule kinase inhibitors in the clinic act by blocking ATP binding or catalytic sites and inhibit all enzyme activity. While this approach may be useful in some cancers, the inevitable drug resistance that occurs in melanoma remains a barrier to achieving sustained therapeutic responses.

The mitogen activated protein kinase (MAPK) family consist of four major members including the extracellular signal-regulated kinases-1 and 2 (ERK1/2), c-Jun N-terminal kinases (JNK), p38 MAP kinases, and ERK5. The MAPK proteins are serine/threonine kinases involved in signal transduction pathways that regulate cell proliferation, apoptosis, differentiation, migration, and inflammation responses to a variety of extracellular signals. MAPK proteins regulate cellular functions through phosphorylation of a diverse number of substrates. In particular, the ERK1/2 proteins have been implicated in the phosphorylation of well over 100 substrates and stringent control over interactions of ERK1/2 with substrate proteins that allow efficient phosphate transfer is essential for proper cellular function. Unregulated activation of the ERK1/2 pathway is often observed in a variety of cancers, which contributes to uncontrolled cell proliferation, survival, and resistance to anti-cancer drugs. Although several selective ATP-competitive inhibitors of ERK1/2 have been developed, these compounds have not advanced to the clinic and do not allow examination of select ERK functions that are dependent on interactions with specific substrate proteins.

Many ERK1/2 substrate and interacting proteins, including the Elk-1 transcription factor, p90 ribosomal S6 kinase-1 (RSK-1), the caspase-9 protease, and the HePTP protein tyrosine phosphatase, contain a DEJL (docking site for ERK and JNK, Leu-X-Leu) motif or D-domain that is involved in kinase recognition. The D-domain consists of basic residues followed by a hydrophobic Leu-X-Leu motif, and interacts with acidic and hydrophobic regions in the carboxy terminus of ERK1/2, referred to as the common docking (CD domain) or D-recruitment site (DRS). A second docking domain, known as the F-site or DEF (docking site for ERK, Phe-X-Phe) motif, has been identified on several ERK1/2 substrates, including transcription factors like Elk-1 and c-Fos, A-Raf kinase, the kinase suppressor of Ras-1 (KSR-1) scaffold protein, and nuclear pore proteins like NUP153 and NUP214. The F-site is typically separated from the phosphorylation site by 6-10 amino acids, whereas the D-domain may be located 20 amino acids further from the phosphorylation site to accommodate the spatially separated hydrophobic interactions.

The DRS on ERK2 includes residues Asp316 and Asp319, adjacent hydrophobic amino acids, and ED domain residues (Glu160/Asp161 for p38α MAP kinase and Thr157/Thr158 for ERK2) that facilitate selective interactions between D-domain containing substrates and MAP kinases. F-site containing substrates interact with hydrophobic regions that make up the F-recruitment site (FRS) on ERK2 and include residues Leu198, Tyr231, Leu232, Leu235, and Tyr261. Other MAP kinases, including p38α, may also utilize a FRS-like binding motif during substrate recognition. Beyond the DRS and FRS sites, experimental studies using ERK2 mutants have implicated other residues that may be important for ERK interactions with substrates or other regulatory proteins. Indeed, ERK2, and other MAP kinases, have a unique insert in the kinase homology region that may regulate it's interactions with upstream activating MEK proteins. Given the large number of substrates regulated by ERK1/2 proteins, it is likely that additional docking sites will be identified on ERK1/2 proteins that regulate specific protein-protein interactions.

Promising new drugs that target the mutated and active form of BRaf in melanoma cells have clinical limitations due to the unanticipated activation of the ERK1/2 pathway through alternate mechanisms and the activation of compensatory signaling pathways that lead to drug resistance. In addition, MEK-independent mechanisms may activate ERK in cancer cells resistant to clinically relevant Raf or MEK inhibitors. A recent study suggested that targeting ERK directly with ATP competitive inhibitors may overcome resistance to MEK inhibitors. Whether complete blockade of ERK using this approach will induce resistance pathways as observed with the MEK1/2 and BRaf inhibitors remains to be determined.

Regulated activity of ERK1/2 serves integral roles in normal cell processes, whereas unregulated and constitutively active ERK1/2 sustains cancer cell proliferation and survival. Thus, in the absence of discriminating between cancer and normal cells, inhibitors that completely block ERK1/2 signaling are destined to have toxicity to normal cells. Despite extensive data demonstrating the role of ERK1/2 signaling in normal cellular processes and disease states, there is surprisingly little known about the mechanisms involved in ERK1/2 recognition and binding interactions with substrate proteins.

Given that ERK proteins may have nearly 300 interacting partners, with over half of these being phosphorylated substrates, there is a knowledge gap regarding ERK1/2 interactions with substrates that are especially relevant to cancer cell proliferation and survival. The identification of molecules that selectively disrupt these interactions will have a significant impact on the development of novel inhibitors that prevent the phosphorylation and regulation of ERK substrates involved in disease processes while preserving ERK functions in normal cells.

Although the ERK1/2 proteins are key drivers of proliferation and survival in many cancers, they also play essential roles in regulating normal cellular processes. Competitive ATP inhibitors, such as conventionally used in the treatment of cancer, may have toxic effects due to off-target effects involving other kinases. There exists selective pressure on cancer cells to induce compensatory pathways that results from complete ablation of ERK1/2 signaling. Currently, chemotherapeutic drugs that block ERK-regulated pathways by targeting MEK1/2 and BRaf proteins invariably cause drug resistance due to treatment-induced activation of compensatory survival proteins and MEK1 mutations.

BRIEF DESCRIPTION OF THE DRAWINGS

FIG. 10. Selective binding of DRS compound and inhibition of A375.

DETAILED DESCRIPTION OF THE SEVERAL EMBODIMENTS

Figure 1:
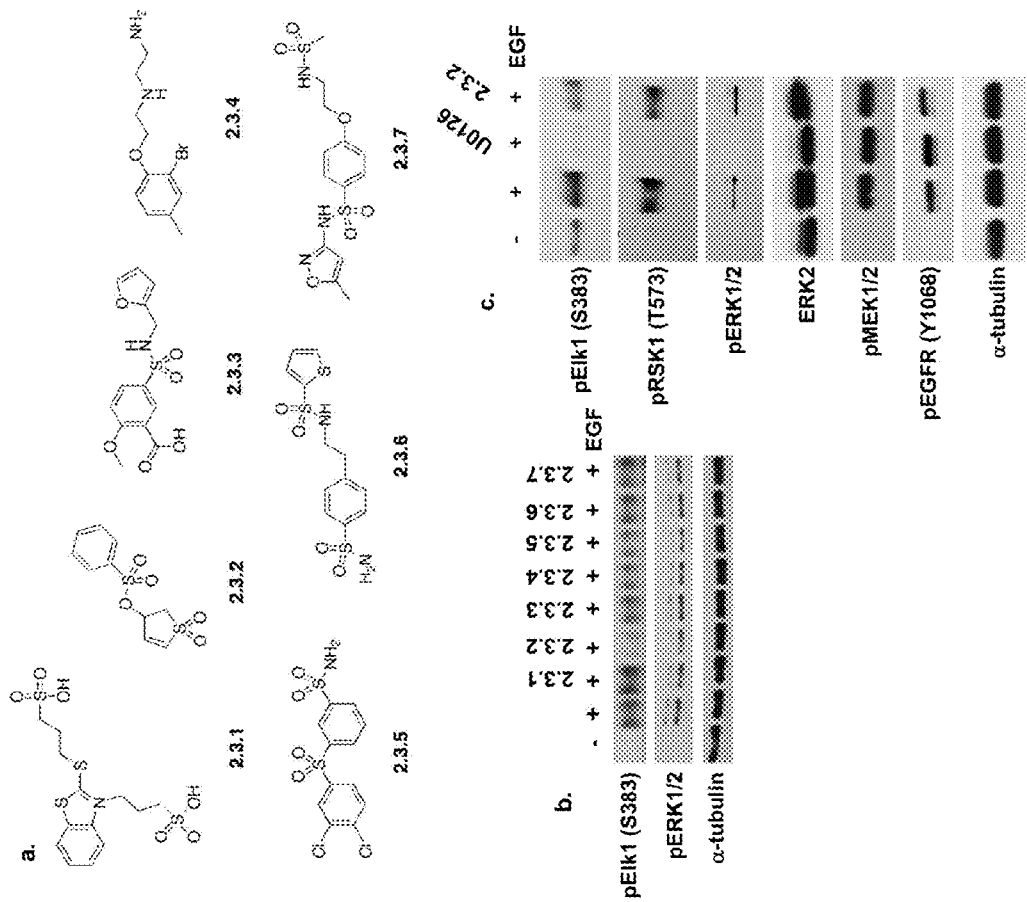
FIG. 1. Selective inhibition of ERK-mediated phosphorylation of substrates by compounds. (a) Structures of the seven diverse compounds identified by CADD and initially tested. (b) HeLa cells were pre-incubated for 30 min with indicated compounds (100 μM) followed by treatment with EGF (25 ng/mL) for 10 min. to activate ERK1/2 signaling. Lysates were immunoblotted for phosphorylated Elk1 (pElk1 S383) or active ERK1/2 (pERK1/2). (c) Following treatment as in FIG. 1b, immunoblot analysis of lysates from cells treated with 2.3.2 showing selectivity for phosphorylation inhibition of Elk1 and less so for RSK1 (pElk1 and pRSK1 T573). Phosphorylation of ERK1/2, MEK1/2 (pERK1/2 and pMEK1/2) or Tyr1068 autophosphorylation of EGFR (pEGFR Y1068) was not affected by 2.3.2. The MEK1/2 inhibitor U0126 (10 μM) was used to block all ERK1/2 signaling and α-tubulin expression was used as a protein loading control.

One embodiment provides a compound, having the formula A-1:

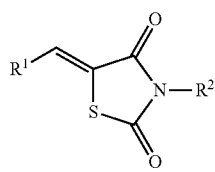

wherein:

$R^1$=alkyl, alkenyl, alkynyl, aryl, cycloalkyl, $CH_2$-aryl, —$C_6H_4$-alkyl, —$C_6H_4$-aryl, —$C_6H_4$-cycloalkyl, —$C_6H_4$—$CH_2$-aryl, —$C_6H_4$—$OR^5$, —$C_6H_4$—$NHR^6$, $OR^5$, $NHR^5$, $NR^5R^6$; wherein $R^5$ and $R^6$ are independently hydrogen, alkyl, aryl, cycloalkyl, or $CH_2$-aryl; and $R^2$=alkyl, aryl, cycloalkyl, $CH_2$-aryl, $CH_2CH_2NH_2$, $CH_2CH_2CH_2NH_2$, $CH_2CH_2NHR^4$, $CH_2CH_2NR^4R^4$, $CH_2CH_2NHCOR^4$, $CH_2CH_2NHCO_2R^4$, $CH_2CH_2NHSO_2R^4$, $CH_2CH_2CH_2NHR^4$, $CH_2CH_2CH_2NR^4R^4$, $CH_2CH_2CH_2NHCOR^4$, $CH_2CH_2CH_2NHCO_2R^4$, $CH_2CH_2CH_2NHSO_2R^4$; wherein $R^4$=independently hydrogen, alkyl, aryl, cycloalkyl, or $CH_2$-aryl, or wherein two $R^4$'s can form a ring;

and wherein A-1 is not one of the following compounds:

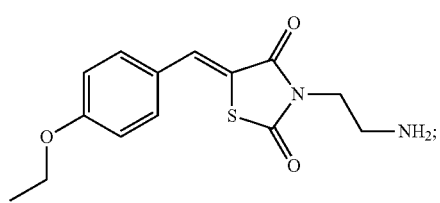
76

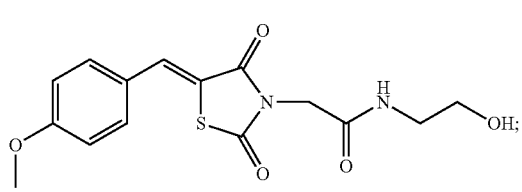
76.1

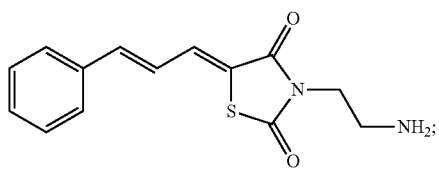
76.2

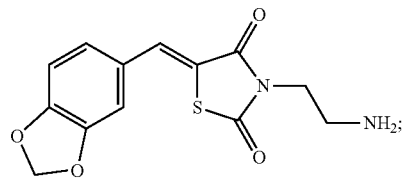
76.3

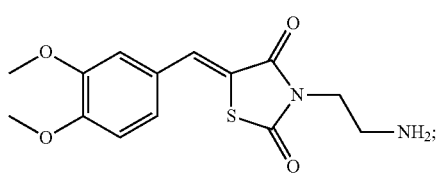
76.4

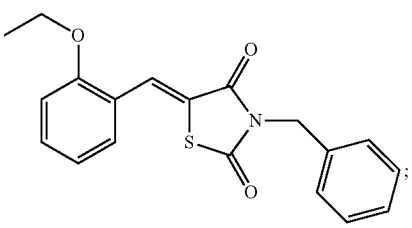
76.5

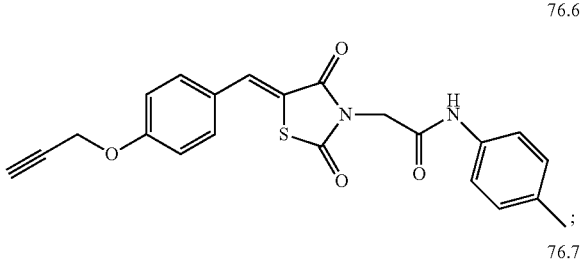
76.6

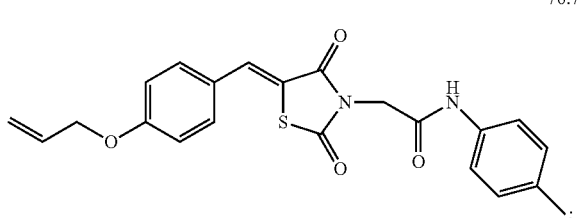
76.7

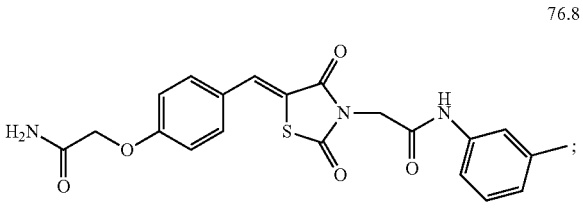
76.8

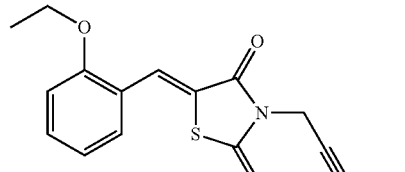
76.9

; or

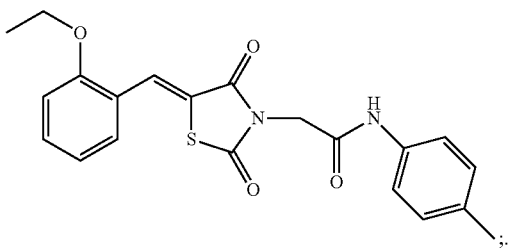

76.10

One embodiment provides a composition, comprising the having the formula A-1 and a pharmaceutically acceptable carrier.

One embodiment provides a compound, having the formula E-1:

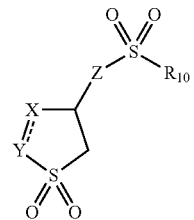

E-1 wherein:

$R^9$=alkyl, alkenyl, alkynyl, aryl, cycloalkyl, $CH_2$-aryl, —$C_6H_4$-alkyl, —$C_6H_4$-aryl, —$C_6H_4$-cycloalkyl, —$C_6H_4$—$CH_2$-aryl, —$C_6H_4$—$OR^5$, —$C_6H_4$—$NHR^6$, $OR^5$, $NHR^5$, $NR^5R^6$; wherein $R^5$ and $R^6$ are independently hydrogen, alkyl, aryl, cycloalkyl, or $CH_2$-aryl; and $R^{10}$=alkyl, aryl, cycloalkyl, $CH_2$-aryl, $CH_2CH_2NH_2$, $CH_2CH_2CH_2NH_2$, $CH_2CH_2NHR^4$, $CH_2CH_2NR^4R^4$, $CH_2CH_2NHCOR^4$, $CH_2CH_2NHCO_2R^4$, $CH_2CH_2NHSO_2R^4$, $CH_2CH_2CH_2NHR^4$, $CH_2CH_2CH_2NR^4R^4$, $CH_2CH_2CH_2NHCOR^4$, $CH_2CH_2CH_2NHCO_2R^4$, $CH_2CH_2CH_2NHSO_2R^4$; wherein $R^4$=independently hydrogen, alkyl, aryl, cycloalkyl, or $CH_2$-aryl, or wherein two $R^4$'s can form a ring;

and wherein E-1 is not one of the following compounds:

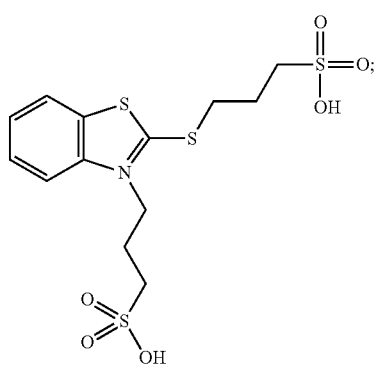

2.3.1

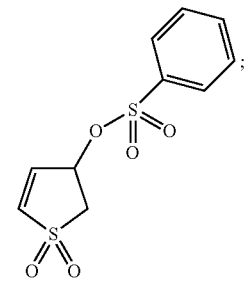

2.3.2

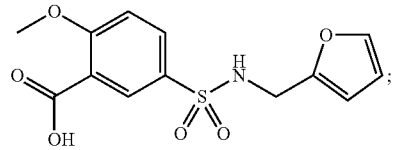

2.3.3

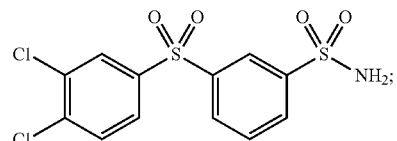

2.3.5

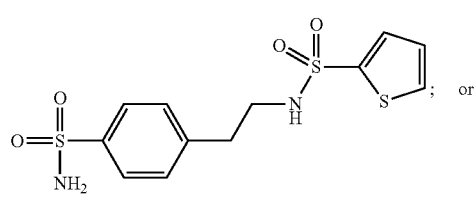

2.3.6

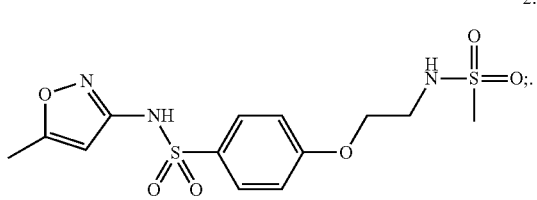

; or 2.3.7

In one embodiment, the compound has the formula E-2:

E-2 wherein:

$R^{10}$=alkyl, aryl, cycloalkyl, or $CH_2$-aryl;

X=>C=O, >$CR^{13}$, >$CHR^{13}$; wherein $R^{13}$=independently hydrogen, alkyl, aryl, cycloalkyl, $CH_2$-aryl, or >$CR^{13}R^{14}$; wherein $R^{14}$=independently hydrogen, alkyl, aryl, cycloalkyl, or $CH_2$-aryl;

Y=>$CR^{15}$, >$CHR^{15}$; wherein $R^{15}$=independently hydrogen, alkyl, aryl, cycloalkyl, $CH_2$-aryl, or >$CR^{15}R^{16}$; wherein $R^{16}$=independently hydrogen, alkyl, aryl, cycloalkyl, or $CH_2$-aryl; and Z=—O—, >NR$^{17}$; wherein R$^{17}$=independently hydrogen, alkyl, aryl, cycloalkyl, or CH$_2$-aryl.

One embodiment provides a composition, comprising the compound having formula E-1 and a pharmaceutically acceptable carrier.

One embodiment provides a method for treating cancer, comprising administering the compound having formula A-1 to a subject in need of cancer treatment.

One embodiment provides a method for treating cancer, comprising administering the subject compound to a subject in need of cancer treatment, wherein the cancer is an ERK-dependent cancer associated with an extracellular signal-related kinase (ERK) pathway.

One embodiment provides a method for treating cancer, comprising administering the subject compound to a subject in need of cancer treatment, wherein the ERK pathway is adenosine triphosphate (ATP) independent.

One embodiment provides a method for treating cancer, comprising administering the subject compound to a subject in need of cancer treatment, wherein the cancer is associated with receptor tyrosine kinase overexpression (EGFR, HER2).

One embodiment provides a method for treating cancer, comprising administering the subject compound to a subject in need of cancer treatment, wherein the cancer is associated with a Ras or BRaf mutation.

One embodiment provides a method for treating cancer, comprising administering the subject compound to a subject in need of cancer treatment, wherein the cancer is carcinoma, breast cancer, pancreatic cancer, non-small cell lung carcinoma, thyroid cancer, melanoma, seminoma, bladder cancer, liver cancer, kidney cancer, myelodysplastic syndrome, acute myelogenous leukemia, colorectal cancer, or a combination thereof.

In one embodiment, the compound has the formula B-2:

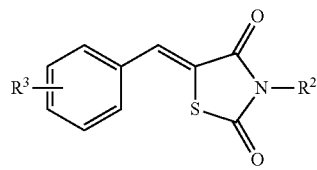

B-2 wherein:
R$^2$=alkyl, aryl, cycloalkyl, alkoxy, cycloalkoxy, aryloxy, CH$_2$-aryl, CH$_2$CH$_2$NH$_2$, CH$_2$CH$_2$NHR$^4$, CH$_2$CH$_2$NHCOR$^4$, CH$_2$CH$_2$NHCO$_2$R$^4$, CH$_2$CH$_2$NHSO$_2$R$^4$; wherein R$^4$=independently hydrogen, alkyl, aryl, cycloalkyl, or CH$_2$-aryl; and
R$^3$=ortho-, meta- and/or para-alkyl, aryl, cycloalkyl, CH$_2$-aryl, OR$^5$, NHR$^6$; wherein R$^5$ and R$^6$ are independently alkyl, aryl, cycloalkyl, or CH$_2$-aryl.

In one embodiment, the compound has the formula B-3:

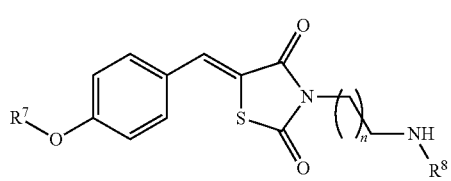

B-3 wherein n=0, 1, 2;
R$^7$=alkyl, aryl, cycloalkyl, CH$_2$-aryl; and
R$^8$=alkyl, aryl, cycloalkyl, CH$_2$-aryl.

One embodiment provides a method for treating cancer, comprising administering a compound having the formula G1 to a subject in need of cancer treatment:

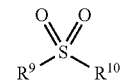

G-1 wherein:
R$^9$=alkyl, alkenyl, alkynyl, aryl, cycloalkyl, CH$_2$-aryl, —C$_6$H$_4$-alkyl, —C$_6$H$_4$-aryl, —C$_6$H$_4$-cycloalkyl, —C$_6$H$_4$—CH$_2$-aryl, —C$_6$H$_4$—OR$^5$, —C$_6$H$_4$—NHR$^6$, OR$^5$, NHR$^5$, NR$^5$R$^6$; wherein R$^5$ and R$^6$ are independently hydrogen, alkyl, aryl, cycloalkyl, or CH$_2$-aryl; and R$^{10}$=alkyl, aryl, cycloalkyl, CH$_2$-aryl, CH$_2$CH$_2$NH$_2$, CH$_2$CH$_2$CH$_2$NH$_2$, CH$_2$CH$_2$NHR$^4$, CH$_2$CH$_2$NR$^4$R$^4$, CH$_2$CH$_2$NHCOR$^4$, CH$_2$CH$_2$NHCO$_2$R$^4$, CH$_2$CH$_2$NHSO$_2$R$^4$, CH$_2$CH$_2$CH$_2$NHR$^4$, CH$_2$CH$_2$CH$_2$NR$^4$R$^4$, CH$_2$CH$_2$CH$_2$NHCOR$^4$, CH$_2$CH$_2$CH$_2$NHCO$_2$R$^4$, CH$_2$CH$_2$CH$_2$NHSO$_2$R$^4$; wherein R$^4$=independently hydrogen, alkyl, aryl, cycloalkyl, or CH$_2$-aryl, or wherein two R$^4$'s can form a ring.

In one embodiment, the compound has the formula G-2:

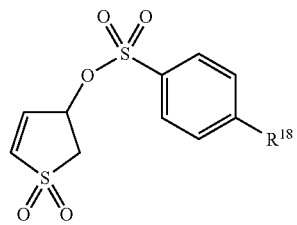

G-2 wherein R$^{18}$=alkyl, aryl, cycloalkyl, CH$_2$-aryl, alkenyl, vinyl.

Although the ERK 1/2 proteins are key drivers of proliferation and survival in many cancers, they also play essential roles in regulating normal cellular processes. The present inventors have adopted an innovative approach to develop small molecular weight compounds that are able to selectively inhibit ERK functions by disrupting the phosphorylation of key substrate proteins. The approach is innovative in that the compounds target substrate docking domains on ERK and do not act as competitive ATP inhibitors, such that they may be less toxic due to fewer off-target effects involving other kinases. It is believed that this approach will reduce selective pressure on cancer cells to induce compensatory pathways that results from complete ablation of ERK 1/2 signaling. Unlike conventional chemotherapeutic drugs that block ERK-regulated pathways by targeting MEK1/2 and BRaf proteins, which invariably cause drug resistance due to treatment-induced activation of compensatory survival proteins and MEK1 mutations, one embodiment targets multiple signaling pathways and provides a benefit to cancer patients who have developed drug resistance. In one embodiment, a partial inhibition of ERK signaling functions is achieved, and arrests cancer cell growth and apoptosis while reducing the selective pressures that induce drug resistance pathways.

In one embodiment, the compounds described herein may be desirably utilized as in vivo chemical probes for their potential use in studying disease treatment, to discover and/or validate novel biological targets that will inform studies of disease mechanisms, and to further the development of more potent therapeutic agents against cancer. In one embodiment, the compounds herein desirably act on a known target, ERK, but also specifically target substrate binding domains of ERK, rather than the ATP binding site. In one embodiment, the compounds and methods herein may have particular advantages in the study of the complex signaling networks regulated by ERK proteins as well as potential development into novel therapeutic agents for treatment of cancer.

For the compounds herein, any one or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ may be suitably and independently selected from hydrogen, an alkyl group, a cycloalkyl group, an aryl group, an alkenyl group, an alkynyl group, a hydroxy group, an alkoxy group, a heterocyclic group, a heteroaryl group, an aryloxy group, a heteroaryloxy group, an aralkyl group, a heteroaralkyl group, an aralkoxy group, a heteroaralkoxy group, an amino group, an alkylamino group, a dialkylamino group, an arylalkylamino group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an oxo group, a carbonyl group, a carboxylic acid group, a carboxylate group, an alkylsulfonyl group, an arylsulfonyl group, a mercapto group, an alkylthio group, a halo group, perhaloalkyl group, a perhaloalkoxy group, a perhalocycloalkyl group, a perhaloalkenyl group, a perhaloalkynyl group, a perhaloaryl group, or a perhaloaralkyl group; wherein each group may be optionally and independently straight or branched; wherein each group may be optionally and independently substituted by one or more independent substituents; and wherein one or more than one atom in each group may be optionally and independently replaced with one or more independent heteroatoms.

In one embodiment, in the compound A-1, $R^1$ is alkyl, alkenyl, alkynyl, aryl, cycloalkyl, $CH_2$-aryl, —$C_6H_4$-alkyl, —$C_6H_4$-aryl, —$C_6H_4$-cycloalkyl, —$C_6H_4$—$CH_2$-aryl, —$C_6H_4$—$OR^5$, —$C_6H_4$—$NHR^6$, $OR^5$, $NHR^5$, $NR^5R^6$; wherein $R^5$ and $R^6$ are independently hydrogen, alkyl, aryl, cycloalkyl, or $CH_2$-aryl. In one embodiment, in the compound A-1, $R^1$ is substituted with one or more substituents. In one embodiment, $R^1$ is straight or branched. In one embodiment, $R^1$ contains one or more hetero atoms, e.g., N, O, or both. In one embodiment, $R^1$ is substituted with an amide, carbamide, sulfonamide, halogen, methoxy, nitro, amino, carbonyl, sulfonyl, thiol, hydroxyl, carboxylic acid, alkyl ester. In one embodiment, $R^1$ is hydrophobic. In one embodiment, $R^1$ is polar, but non-ionizable under physiological conditions.

In one embodiment, in the compound A-1, $R^2$ is para-benzoic acid. In one embodiment, in the compound A-1, $R^2$ is morpholine or piperidine.

In one embodiment, an alkyl group is a univalent, acyclic, straight or branched, substituted or unsubstituted, saturated or unsaturated, hydrocarbon radical. In one embodiment, the alkyl group has the general formula (notwithstanding optional unsaturation, substitution or the like) —$C_nH_{2n+1}$. In one embodiment, n is 1-15 (($C_1$-$C_{15}$) alkyl), which may suitably include $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, and $C_{15}$ alkyl groups. In one embodiment, the alkyl group may be straight or branched, substituted or unsubstituted, saturated or unsaturated, or any combination thereof. In one embodiment, one or more hydrogens may be optionally and independently replaced by one or more substituent groups. In one embodiment, one or more carbon atoms may be optionally and independently replaced with one or more heteroatoms such as O, S, N, B, or any combination thereof. In one embodiment, the alkyl group may contain one or more double bond, one or more triple bond, or any combination thereof. In one embodiment, the alkyl group is attached to the parent structure through one or more independent divalent intervening substituent groups. Some examples of alkyl groups, which are not intended to be limiting, include methyl, ethyl, n-propyl, isopropyl, n-butyl, iso-butyl, secondary-butyl, tertiary-butyl, and the like.

In one embodiment, a cycloalkyl group is a univalent, mono- or polycyclic, substituted or unsubstituted, saturated or unsaturated hydrocarbon radical. In one embodiment, the cycloalkyl group has the general formula (notwithstanding optional unsaturation, substitution, or the like) —$C_nH_{2n-1}$. In one embodiment, n is 3-10 (($C_3$-$C_{10}$) cycloalkyl), which may suitably include $C_3$, $C_4$, $C_5$, $C_6$, $C_7$, $C_8$, $C_9$, and $C_{10}$ cycloalkyl groups. In one embodiment, the cycloalkyl group is substituted or unsubstituted, saturated or unsaturated, mono-, bi-, tri-, or poly-cyclic, or any combination thereof. In one embodiment, one or more hydrogens may be optionally and independently replaced by one or more substituent groups. In one embodiment, the cycloalkyl group may have one or more sites of unsaturation, e.g., it may contain one or more double bond, one or more triple bond, or any combination thereof. In one embodiment, one or more carbon atoms may be optionally and independently replaced with one or more heteroatoms such as O, S, N, B, or any combination thereof. In one embodiment, the cycloalkyl group is attached to the parent structure through one or more independent divalent intervening substituent groups. Some examples of cycloalkyl groups, which are not intended to be limiting, include cyclopropyl, cyclobutyl, cyclopentyl, cyclohexyl, cycloheptyl, cyclooctyl, cyclononyl, and the like.

In one embodiment, an alkenyl group is a univalent, straight or branched, substituted or unsubstituted, unsaturated hydrocarbon radical. In one embodiment, the alkenyl group has the general formula (notwithstanding optional substitution, higher degree of unsaturation, or the like) —$C_nH_{2n-2}$. In one embodiment, n is 2-15 (($C_2$-$C_{15}$) alkenyl), which may suitably include $C_2$, $C_3$, $C_4$, $C_5$, $C_6$, $C_7$, $C_8$, $C_9$, $C_{10}$, $C_{11}$, $C_{12}$, $C_{13}$, $C_{14}$, and $C_{15}$ alkenyl groups. In one embodiment, the alkenyl group may be straight or branched, substituted or unsubstituted, have more than one degree of unsaturation, or any combination thereof. In one embodiment, one or more carbon atoms may be optionally and independently replaced with one or more heteroatoms such as O, S, N, B, or any combination thereof. In one embodiment, the alkenyl group is attached to the parent structure through one or more independent divalent intervening substituent groups. Some examples of alkenyl groups, which are not intended to be limiting, include ethenyl, 1-propenyl, 2-propenyl(allyl), iso-propenyl, vinyl, 2-methyl-1-propenyl, 1-butenyl, 2-butenyl, alkadienes, alkatrienes, and the like.

In one embodiment, an alkynyl group is a univalent, straight or branched, substituted or unsubstituted, hydrocarbon radical that contains one or more carbon-carbon triple bond. In one embodiment, the alkenyl group has the general formula (notwithstanding optional substitution, higher degree of unsaturation, or the like) —$C_nH_{2n-3}$. In one embodiment, n is 2-15 (($C_2$-$C_{15}$) alkynyl), which may suitably include $C_2$, $C_3$, $C_4$, $C_5$, $C_6$, $C_7$, $C_8$, $C_9$, $C_{10}$, $C_{11}$, $C_{12}$, $C_{13}$, $C_{14}$, and $C_{15}$ alkynyl groups. In one embodiment, the alkynyl group may be straight or branched, substituted or unsubstituted, have more than one degree of unsaturation, or any combination thereof. In one embodiment, one or more carbon atoms may be optionally and independently replaced with one or more heteroatoms such as O, S, N, B, or any combination thereof. In one embodiment, the alkynyl group is attached to the parent structure through one or more independent divalent intervening substituent groups. Some examples of alkynyl groups, which are not intended to be limiting, include alkadiynes, alkatriynes, ethynyl, propynyl, butynyl, and the like.

In one embodiment, an aryl group is a univalent, substituted or unsubstituted, monocyclic or polycyclic aromatic hydrocarbon radical. In one embodiment, an aryl group is a radical which, in accordance with Hückel's theory, includes a cyclic, delocalized (4n+2) pi-electron system. In one embodiment the aryl group is a $C_5$-$C_{20}$ aryl group. The $C_5$-$C_{20}$ aryl group may suitably include $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ aryl groups. In one embodiment, the aryl group may be substituted or unsubstituted, be substituted with two or more groups that taken together form a cyclic group, or any combination thereof. In one embodiment, the aryl group is attached to the parent structure through one or more independent divalent intervening substituent groups. Some examples of aryl groups, which are not intended to be limiting, include phenyl, naphthyl, tetrahydronaphthyl, phenanthryl, pyrenyl, anthryl, indanyl, chrysyl, and the like.

In one embodiment, a heterocyclic group is a univalent, substituted or unsubstituted, saturated or unsaturated, mono- or polycyclic hydrocarbon radical that contains one or more heteroatoms in one or more of the rings. In one embodiment, the heterocyclic group is a $C_3$-$C_{15}$ cyclic group, in which one or more ring carbons is independently replaced with one or more heteroatoms. The $C_3$-$C_{15}$ heterocyclic group may suitably include $C_3$, $C_4$, $C_5$, $C_6$, $C_7$, $C_8$, $C_9$, $C_{10}$, $C_{11}$, $C_{12}$, $C_{13}$, $C_{14}$, and $C_{15}$ cyclic groups in which one or more ring carbons is independently replaced with one or more heteroatoms. In one embodiment, the heteroatoms are selected from one or more of N, O, or S, or any combination thereof. In one embodiment, the N or S or both may be independently substituted with one or more substituents. In one embodiment, the heterocyclic group is substituted or unsubstituted, saturated or unsaturated, mono-, bi-, tri-, or poly-cyclic, or any combination thereof. In one embodiment, one or more hydrogens may be optionally and independently replaced by one or more substituent groups. In one embodiment, the heterocyclic group may include one or more carbon-carbon double bonds, carbon-carbon triple bonds, carbon-nitrogen double bonds, or any combination thereof. In one embodiment, the heterocyclic group is attached to the parent structure through one or more independent divalent intervening substituent groups. Some examples of heterocyclic groups, which are not intended to be limiting, include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, 1,4-oxazin-2-yl, 1,2,5-oxathiazin-4-yl, and the like In one embodiment, a heteroaryl group is univalent, substituted or unsubstituted, monocyclic or polycyclic aromatic hydrocarbon radical in which one or more ring carbons is independently replaced with one or more heteroatoms selected from 0, S and N. In one embodiment, in addition to said heteroatom, the heteroaryl group may optionally have up to 1, 2, 3, or 4 N atoms in the ring. In one embodiment, the heteroaryl group is an aryl group in which one or more ring carbons are independently replaced with one or more heteroatoms. In one embodiment, a heteroaryl group is an aromatic radical, which contains one or more heteroatoms and which, in accordance with Hückel's theory, includes a cyclic, delocalized (4n+2) pi-electron system. In one embodiment, the heteroaryl group is a $C_5$-$C_{20}$ heteroaryl group. The $C_5$-$C_{20}$ heteroaryl group may suitably include $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ aryl groups in which one or more than one ring carbon is independently replaced with one or more heteroatoms. In one embodiment, the heteroaryl group may be substituted or unsubstituted, be substituted with two or more groups that taken together form a cyclic group, or any combination thereof. In one embodiment, the heteroaryl group is attached to the parent structure through one or more independent divalent intervening substituent groups. Some examples of heteroaryl groups, which are not intended to be limiting, include heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like.

In one embodiment, an aralkyl group is a univalent radical derived from one or more aryl groups attached to one or more of an alkylene group, cycloalkylene group, alkenylene group, alkynylene group, or combination thereof. The alkylene, cycloalkylene, alkenylene, and alkynylene groups are divalent radicals derived from the removal of hydrogen from the respective alkyl, cycloalkyl, alkenyl, or alkynyl groups. In this context, any combination of aryl group and alkyl, cycloalkyl, alkenyl, or alkynyl group is contemplated. In one embodiment, the aryl group is attached to the parent structure through one or more of the alkylene group, cycloalkylene group, alkenylene group, alkynylene group, or combination thereof as appropriate. In one embodiment, the aralkyl group may be attached to the parent structure through one or more independent divalent intervening substituent groups.

In one embodiment, a heteroaralkyl group is a univalent radical derived from one or more heteroaryl groups attached to one or more of an alkylene group, cycloalkylene group, alkenylene group, alkynylene group, or combination thereof. The alkylene, cycloalkylene, alkenylene, and alkynylene groups are divalent radicals derived from the removal of hydrogen from the respective alkyl, cycloalkyl, alkenyl, or alkynyl groups. In this context, any combination of heteroaryl group and alkyl, cycloalkyl, alkenyl, or alkynyl group is contemplated. In one embodiment, the heteroaryl group is attached to the parent structure through one or more of the alkylene group, cycloalkylene group, alkenylene group, alkynylene group, or combination thereof as appropriate. In one embodiment, the heteroaralkyl group may be attached to the parent structure through one or more independent divalent intervening substituent groups.

In one embodiment, a halo group is a univalent halogen radical or halogen-containing substituent group, e.g., one that is or contains one or more F, Br, Cl, I, or combination thereof. As used herein, the term "halogen" or "halo" includes fluoro, chloro, bromo, or iodo, or fluoride, chloride, bromide or iodide. In one embodiment, a halogen containing substituent group may suitably include a substituent group in which one or more hydrogen atoms are independently replaced with one or more halogens. In one embodiment, the halo group may be attached to the parent structure through one or more independent divalent intervening substituent groups.

In one embodiment, a hydroxy group is a univalent hydroxyl radical (—OH) or hydroxy-containing substituent group, e.g., one that is or contains one or more —OH. As used herein the term, "hydroxy" includes an —OH group. In one embodiment, a hydroxy-containing substituent group may suitably include a substituent group in which one or more hydrogen atoms are independently replaced with one or more —OH groups. In one embodiment, the hydroxyl group may be attached to the parent structure through one or more independent divalent intervening substituent groups.

In one embodiment, an oxo group is a univalent radical that contains an oxygen atom, =O, doubly bonded to carbon or another element. In one embodiment, the oxo group suitably includes aldehydes, carboxylic acids, ketones, sulfonic acids, amides, esters, and combinations thereof. In one embodiment, the oxo group may be attached to the parent structure through one or more independent divalent intervening substituent groups.

In one embodiment, a mercapto or thiol group is a univalent —SR radical or an —SR— containing group. The R group is suitably chosen from any of the substituent groups. In one embodiment, the mercapto group may be attached to the parent structure through one or more independent divalent intervening substituent groups.

In one embodiment, an amino group is a univalent —NH$_2$ radical or an —NH$_2$-containing substituent group. In one embodiment, the amino group may be attached to the parent structure through one or more independent divalent intervening substituent groups.

In one embodiment, an alkylamino group is a univalent —NRH radical or an —NRH— containing substituent group. The R group is suitably chosen from any of the substituent groups. In one embodiment, the alkylamino group may be attached to the parent structure through one or more independent divalent intervening substituent groups.

In one embodiment, a dialkylamino group is a univalent —NRR radical or an —NRR— containing substituent group. The R groups may be the same or different and are suitably and independently chosen from any of the substituent groups. In one embodiment, the dialkylamino group may be attached to the parent structure through one or more independent divalent intervening substituent groups.

In one embodiment, a carbonyl group is a univalent radical that contains a —CR(=O) group. In one embodiment, the carbonyl group suitably includes aldehydes, ketones, and combinations thereof. The R group is suitably chosen from any of the substituent groups. In one embodiment, the carbonyl group may be attached to the parent structure through one or more independent divalent intervening substituent groups.

In one embodiment, a carboxylic acid group is a univalent —C(C=O)OH radical or a —C(=O)OH-containing substituent group. In one embodiment, the carboxylic acid group may be attached to the parent structure through one or more independent divalent intervening substituent groups.

In one embodiment, a carboxylate group is a univalent —C(=O)O$^-$ anion, —C(C=O)OR, or —C(=O)OM, wherein M is a metal cation, or —C(=O)O$^-$ anion, —C(C=O)OR, or —C(C=O)OM-containing substituent group. The R group is suitably chosen from any of the substituent groups. The metal cation is suitably chosen from Li, Na, K, and the like. In one embodiment, the carboxylate group may be attached to the parent structure through one or more independent divalent intervening substituent groups.

In one embodiment, an amide group is a univalent -E(=O) NRR radical or a -E(=O)NRR— containing substituent group, in which E may be other than carbon, e.g., a chalcogen (e.g., S, Se, Te), or P. In one embodiment, the amide group suitably includes univalent lactams, peptides, phosphoramides, or sulfamides, —S(=O)$_2$NRR, —P(=O)(OH)NRR, and the like. The R groups may be the same or different and are suitably and independently chosen from any of the substituent groups. In one embodiment, the amide group may be attached to the parent structure through one or more independent divalent intervening substituent groups.

In one embodiment, a carbamoyl group is a univalent —C(C=O)NRR radical or a —C(=O)NRR-containing substituent group. The R groups may be the same or different and are suitably and independently chosen from any of the substituent groups. In one embodiment, the carbamoyl group may be attached to the parent structure through one or more independent divalent intervening substituent groups.

In one embodiment, a sulfonyl group is a univalent —S(=O)$_2$R radical or a —S(=O)$_2$R— containing substituent group. The R group is suitably chosen from any of the substituent groups. In one embodiment, the sulfonyl group may be attached to the parent structure through one or more independent divalent intervening substituent groups.

In one embodiment, an alkylthio or sulfide group is a univalent —SR radical or an —SR— containing substituent group. The R group is suitably chosen from any of the substituent groups.

In one embodiment, the alkylthio group may be attached to the parent structure through one or more independent divalent intervening substituent groups.

In one embodiment, an alkoxy group is a univalent radical derived from an —O-alkyl group. In one embodiment, the alkylthio group may be attached to the parent structure through one or more independent divalent intervening substituent groups.

In one embodiment, an aryloxy group is a univalent radical derived from an —O-aryl group. In one embodiment, the aryloxy group may be attached to the parent structure through one or more independent divalent intervening substituent groups.

In one embodiment, a heteroaryloxy group is a univalent radical derived from an —O-heteroaryl group. In one embodiment, the heteroaryloxy group may be attached to the parent structure through one or more independent divalent intervening substituent groups.

In one embodiment, an aralkoxy group is a univalent radical derived from an —O-aralkyl group. In one embodiment, the aralkoxy group may be attached to the parent structure through one or more independent divalent intervening substituent groups.

In one embodiment, a heteroaralkoxy group is a univalent radical derived from an —O-heteroaryl group. In one embodiment, the heteroaralkoxy group may be attached to the parent structure through one or more independent divalent intervening substituent groups.

In one embodiment, an alkylcarbonyl group is a univalent is radical derived from a -carbonyl-alkyl group. In one embodiment, the alkylcarbonyl group may be attached to the parent structure through one or more independent divalent intervening substituent groups.

In one embodiment, an alkoxycarbonyl group is a univalent radical derived from a -carbonyl-O-alkyl group. In one embodiment, the alkoxycarbonyl group may be attached to the parent structure through one or more independent divalent intervening substituent groups.

In one embodiment, an alkylaminocarbonyl group is a univalent radical derived from a -carbonyl-alkylamino group. In one embodiment, the heteroaralkoxy group may be attached to the parent structure through one or more independent divalent intervening substituent groups.

In one embodiment, a dialkylamino carbonyl group is a univalent radical derived from a carbonyl-dialkylamino group. In one embodiment, the dialkylamino carbonyl group may be attached to the parent structure through one or more independent divalent intervening substituent groups.

In one embodiment, an arylcarbonyl group is a univalent radical derived from a -carbonyl-aryl group. In one embodiment, the arylcarbonyl group may be attached to the parent structure through one or more independent divalent intervening substituent groups.

In one embodiment, an aryloxycarbonyl group is a univalent radical derived from a -carbonyl-O-aryl group. In one embodiment, the aryloxycarbonyl group may be attached to the parent structure through one or more independent divalent intervening substituent groups.

In one embodiment, an alkylsulfonyl group is a univalent radical derived from a -sulfonyl-alkyl group. In one embodiment, the alkylsulfonyl group may be attached to the parent structure through one or more independent divalent intervening substituent groups.

In one embodiment, an arylsulfonyl group is a univalent radical derived from a -sulfonyl-aryl group. In one embodiment, the arylsulfonyl group may be attached to the parent structure through one or more independent divalent intervening substituent groups.

In one embodiment, a perhaloalkyl group is a univalent radical derived from a completely or substantially completely halogenated alkyl group. In one embodiment, the parhaloalkyl group may be attached to the parent structure through one or more independent divalent intervening substituent groups.

In one embodiment, a perhaloalkoxy group is a univalent radical derived from a completely or substantially completely halogenated alkoxy group. In one embodiment, the arylsulfonyl group may be attached to the parent structure through one or more independent divalent intervening substituent groups.

In one embodiment, a perhalocycloalkyl group is a univalent radical derived from a completely or substantially completely halogenated cycloalkyl group. In one embodiment, the perhalocycloalkyl group may be attached to the parent structure through one or more independent divalent intervening substituent groups.

In one embodiment, a perhaloalkenyl group is a univalent radical derived from a completely or substantially completely halogenated alkenyl group. In one embodiment, the perhaloalkenyl group may be attached to the parent structure through one or more independent divalent intervening substituent groups.

In one embodiment, a perhaloalkynyl group is a univalent radical derived from a completely or substantially completely halogenated alkynyl group. In one embodiment, the perhaloalkynyl group may be attached to the parent structure through one or more independent divalent intervening substituent groups.

In one embodiment, a perhaloaryl group is a univalent radical derived from a completely or substantially completely halogenated aryl group. In one embodiment, the perhaloaryl group may be attached to the parent structure through one or more independent divalent intervening substituent groups.

In one embodiment, a perhaloaralkyl group is a univalent radical derived from a completely or substantially completely halogenated aralkyl group. In one embodiment, the perhaloaralkyl group may be attached to the parent structure through one or more independent divalent intervening substituent groups.

In one embodiment, an alkylcarbonyloxy group is a univalent radical derived from an —O-carbonyl-alkyl group. In one embodiment, the alkylcarbonyloxy group may be attached to the parent structure through one or more independent divalent intervening substituent groups.

In one embodiment, an alkoxycarbonyloxy group is a univalent radical derived from an —O-carbonyl-O-alkyl group. In one embodiment, the alkoxycarbonyloxy group may be attached to the parent structure through one or more independent divalent intervening substituent groups.

In one embodiment, an alkylsulfonyloxy group is a univalent radical derived from an —O-sulfonyl-alkyl group. In one embodiment, the alkylsulfonyloxy group may be attached to the parent structure through one or more independent divalent intervening substituent groups.

In one embodiment, an alkoxysulfonyloxy group is a univalent radical derived from an —O-sulfonyl-O-alkyl group. In one embodiment, the alkoxysulfonyloxy group may be attached to the parent structure through one or more independent divalent intervening substituent groups.

In one embodiment, an arylcarbonyloxy group is a univalent radical derived from an —O-carbonyl-aryl group. In one embodiment, the arylcarbonyloxy group may be attached to the parent structure through one or more independent divalent intervening substituent groups.

In one embodiment, an aryloxycarbonyloxy group is a univalent radical derived from an O-carbonyl-O-aryl group. In one embodiment, the aryloxycarbonyloxy group may be attached to the parent structure through one or more independent divalent intervening substituent groups.

In one embodiment, an arylsulfonyloxy group is a univalent radical derived from an —O-sulfonyl-aryl group. In one embodiment, the arylsulfonyloxy group may be attached to the parent structure through one or more independent divalent intervening substituent groups.

In one embodiment, an aryloxysulfonyloxy group is a univalent radical derived from an —O-sulfonyl-O-aryl group. In one embodiment, the aryloxysulfonyloxy group may be attached to the parent structure through one or more independent divalent intervening substituent groups.

In one embodiment, referring to two groups taken together to form a cyclic group, the cyclic group may be suitably derived from a divalent cycloalkylene group or divalent heterocyclic group. The divalent cycloalkylene and heterocyclic groups may be suitably derived from the respective cycloalkyl or heterocyclic groups.

In one embodiment, referring to the replacement of one or more than one atom in each group with one or more heteroatoms, the heteroatoms may be suitably chosen from N, O, P, S, B, or any combination thereof as appropriate. In one embodiment, one or more carbons is replaced with a nitrogen or oxygen.

In one embodiment, the substituent groups described herein may be suitably and independently chosen from one or more of a hydrogen, an azido group, a carbamido group, a carbazoyl group, a cyanato group, a cyano group, an isocyanato group, an isocyano group, a hydroxamino group, a guanidino group, a guanyl group, an imino group, a nitro group, a phospho group, a phosphate group, a phosphine group, a sulfo group, a sulfate group, a sulfonyl group, a carbonyl group, a carboxylic acid group, a carboxylate group, an alkyl group, a cycloalkyl group, a halo group, an alkenyl group, an alkynyl group, a hydroxy group, an oxo group, a mercapto group, an alkylthio group, an alkoxy group, an aryl group, a heterocyclic group, a heteroaryl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, an alkylcarbonyloxy group, an alkoxycarbonyloxy group, an alkylsulfonyloxy group, an alkoxysulfonyloxy group, an arylcarbonyloxy group, an aryloxycarbonyloxy group, an arylsulfonyloxy group, an aryloxysulfonyloxy group, an a perhaloalkyl group, a perhaloalkoxy group, a perhalocycloalkyl group, a perhaloalkenyl group, a perhaloalkynyl group, a perhaloaryl group, a perhaloaralkyl group, or combination thereof. Univalent residues or divalent intervening residues of any substituent group or combination thereof may be suitably used as appropriate.

In one embodiment, the divalent intervening substituent groups may be suitably and independently chosen from one or more of an azo group, an azino group, an azoxy group, a carbonyl group, a dioyl group, a diazoamino group, a disulfinyl group, a dithio group, an oxy group, a hydrazo group, an oxalyl group, a sulfonyl group, a thiocarbonyl group, a thionyl group, a phosphono ester group, a carboxylate group, a thio group; divalent residues of one or more of the following groups: an alkyl group, a cycloalkyl group, an alkenyl group, an alkynyl group, an alkylthio group, an alkyloxy group, an aryl group, a heterocyclic group, a heteroaryl group, an aryloxy group, a heteroaryloxy group, an aralkyl group, a heteroaralkyl group, an aralkoxy group, a heteroaralkoxy group, an amino group, an alkylamino group, a dialkylamino group, an amidine group, an amide group, a carbamoyl group, an alkylcarbonyl group, an alkoxycarbonyl group, an alkylaminocarbonyl group, a dialkylamino carbonyl group, an arylcarbonyl group, an aryloxycarbonyl group, an alkylsulfonyl group, an arylsulfonyl group, an alkylcarbonyloxy group, an alkoxycarbonyloxy group, an alkylsulfonyloxy group, an alkoxysulfonyloxy group, an arylcarbonyloxy group, an aryloxycarbonyloxy group, an arylsulfonyloxy group, an aryloxysulfonyloxy group, an a perhaloalkyl group, a perhaloalkoxy group, a perhalocycloalkyl group, a perhaloalkenyl group, a perhaloalkynyl group, a perhaloaryl group, a perhaloaralkyl group, combination thereof; or combination thereof.

In one embodiment, the compound having formula A-1 has the following formula:

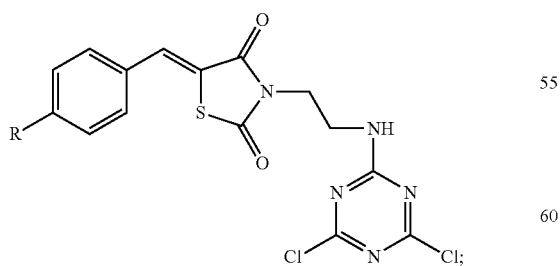

Wherein R can be any alkoxy, cycloalkoxy, aryloxy, aryl, primary amine, secondary amine, or tertiary amine. For example, in the formula above, R may be one of the following:

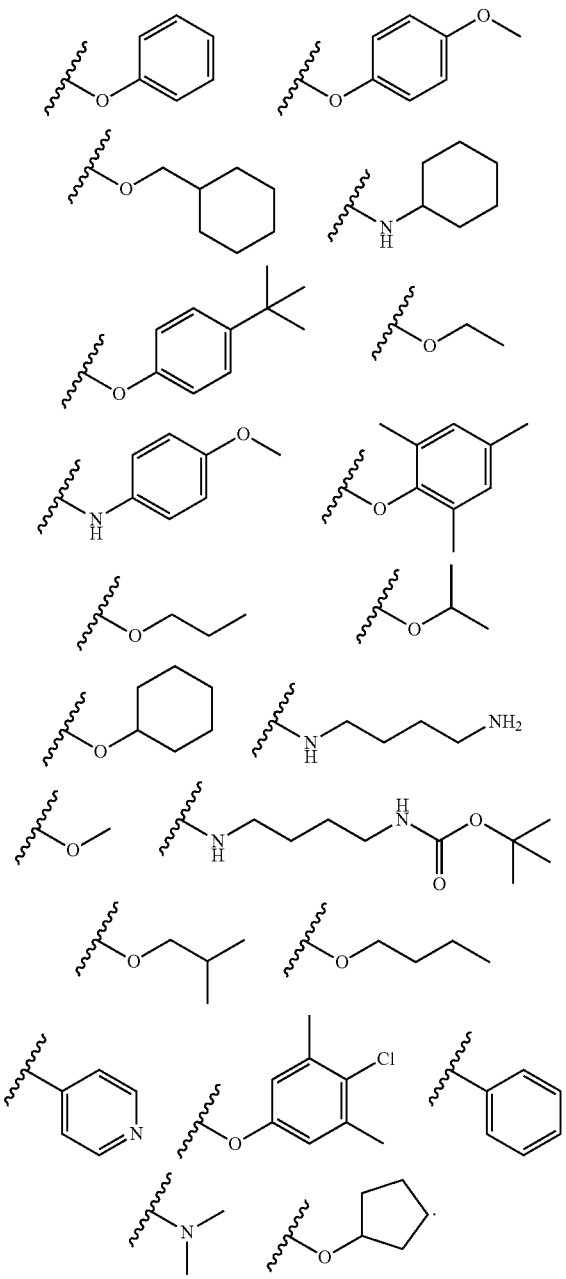

In one embodiment, the compound having formula A-1 has the following formula (SF-2-054):

In one embodiment, the compound having formula A-1 has the following formula (SS-1-019):

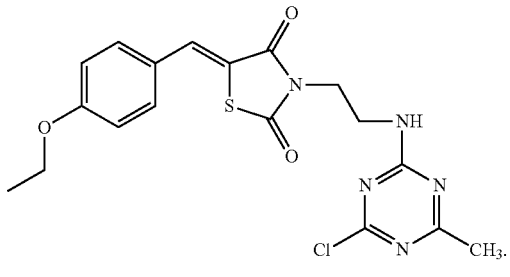 [SMILES: CCOc1ccc(/C=C2\SC(=O)N(CCNc3nc(C)nc(Cl)n3)C2=O)cc1]

In one embodiment, the compound having formula A-1 has the following formula (SF-2-062):

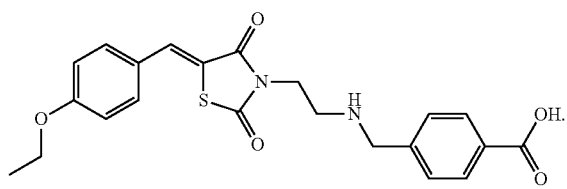 [SMILES: CCOc1ccc(/C=C2\SC(=O)N(CCNCc3ccc(C(=O)O)cc3)C2=O)cc1]

In one embodiment, the compound having formula E-1 has the following formula (2.3.2 (SF-3-026)):

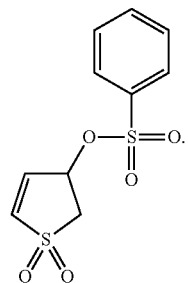 [SMILES: O=S1(=O)C=CC(OS(=O)(=O)c2ccccc2)C1]

In one embodiment, the compound having formula E-1 has the following formula (SF-3-027):

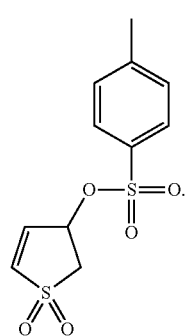 [SMILES: Cc1ccc(S(=O)(=O)OC2C=CS(=O)(=O)C2)cc1]

In one embodiment, the compound having formula E-1 has the following formula (SF-2-028):

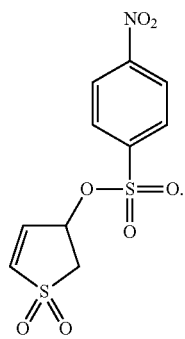 [SMILES: O=[N+]([O-])c1ccc(S(=O)(=O)OC2C=CS(=O)(=O)C2)cc1]

In one embodiment, the compound having formula E-1 has the following formula (SF-2-029)

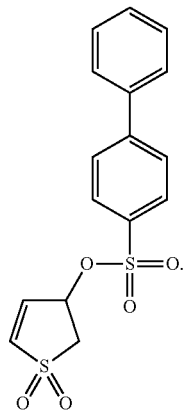 [SMILES: O=S1(=O)C=CC(OS(=O)(=O)c2ccc(-c3ccccc3)cc2)C1]

In one embodiment, the compound having formula E-1 has the following formula (SF-3-030):

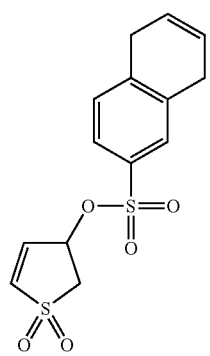

In one embodiment, the compound having formula E-1 has the following formula:

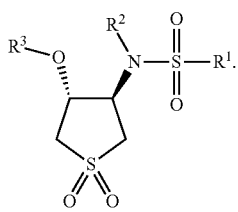

In one embodiment, the compound having formula E-1 has the following formula:

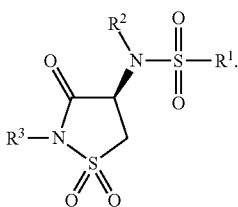

In the E-1 formulas, $R^1$, $R^2$, and $R^3$ are not particularly limiting, and may suitably be one of the following:

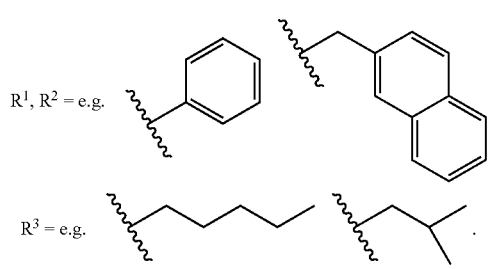

All of the compounds described herein may be easily prepared without undue experimentation by known methods given the teachings herein and the knowledge available to one of ordinary skill in organic chemical syntheses.

In one embodiment, at least one of the subject compounds, salt thereof, prodrug thereof, or combination thereof, may be suitably used in contact with at least one pharmaceutically acceptable carrier or excipient, for use in the methods described herein as a pharmaceutical composition.

In one embodiment, at least one of the subject compounds, salt thereof, prodrug thereof, or combination thereof, optionally in contact with at least one pharmaceutically acceptable carrier or excipient, may be used for the preparation of a medicament for the methods described herein.

In one embodiment, pharmaceutically acceptable means a material that is compatible with the other ingredients of the composition without rendering the composition unsuitable for its intended purpose, and is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers or excipients include, without limitation, any of the standard pharmaceutical carriers or excipients such as phosphate buffered saline solutions, water, emulsions such as oil/water emulsions, microemulsions, and the like.

The compounds and compositions described herein can be formulated without undue experimentation for administration to a mammal, including humans, as appropriate for the particular application. The pharmaceutical compositions may be manufactured without undue experimentation in a manner that is itself known, e.g., by means of conventional mixing, dissolving, dragee-making, levitating, emulsifying, encapsulating, entrapping, spray-drying, or lyophilizing processes, or any combination thereof.

Suitable routes of administration may include, for example, oral, lingual, sublingual, rectal, transmucosal, nasal, buccal, intrabuccal, intravaginal, or intestinal administration; intravesicular; intraurethral; topical administration; transdermal administration; administration by inhalation; parenteral delivery, non-parenteral delivery, including intramuscular, subcutaneous, intramedullary injections, as well as intrathecal, direct intraventricular, intravenous, intraperitoneal, intranasal, or intraocular injections, and optionally in a depot or sustained release formulation. Furthermore, one may administer the compound in a targeted drug delivery system, for example in a liposome. Combinations of administrative routes are possible.

Proper dosages of the compounds and compositions can be determined without undue experimentation using standard dose-response protocols. In one embodiment, the dosage of the compound, salt thereof, or a combination thereof, or pharmaceutical composition, may vary from about 0.001 μg/kg to about 1000 mg/kg. This includes all values and subranges therebetween, including 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, and 1 μg/kg, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1 2, 3, 4, 5, 6, 7, 8, 9, 10, 11, 12, 13, 14, 15, 16, 17, 18, 19, 20, 21, 22, 23, 24, 25, 50, 75, 100, 200, 300, 400, 500, 600, 700, 800, 900, and 1000 mg/kg, and any combination thereof.

The frequency of administration of the compounds and compositions can be determined without undue experimentation using standard dose-response protocols. In one embodiment, the frequency of administration of the compound, salt thereof, or a combination thereof, or pharmaceutical composition, may vary from about 0.5 hours to one month. This range includes all values and subranges therebetween, including about 0.5, 0.75, 1, 2, 3, 4, 5, 6, 7, 8, 9, 10, 12, 14, 16, 18, 20, 24 hours, 1, 2, 3, 4, 5, 6, 7, 8, 9, 10, 12, 14, 16, 18, 20, 24, 28, 30, 31 days, and one month, or any combination thereof. The administration can be suitably adjusted in the case a controlled or sustained release formulation is used. The compounds and compositions for administration can be made without undue experimentation by means well known in the art, for example with pharmaceutically acceptable carrier or excipient for example an inert diluent, solvent, suspending agent or the like. The compositions may be enclosed in gelatin capsules or compressed into tablets. In one embodiment, the pharmaceutical compositions may be incorporated with a carrier or excipient and used in the form of tablets, troches, capsules, elixirs, suspensions, syrups, wafers, chewing gums and the like.

In one embodiment, the compounds and/or compositions are administered orally.

Tablets, pills, capsules, troches and the like may also contain pharmaceutically acceptable carriers or excipients for example binders, additives, disintegrating agents, lubricants, sweetening agents, and flavoring agents. Some examples of binders include microcrystalline cellulose, gum tragacanth or gelatin. Examples of additives include starch or lactose. Some examples of disintegrating agents include alginic acid, cornstarch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compounds can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the compound, in a pharmaceutical composition, into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Some examples of transdermal formulations include patches (such as the well-known nicotine patch), iontophoretic devices, microneedles, ointments, creams, gels, salves and the like.

The compounds can also be prepared for nasal administration. As used herein, nasal administration includes administering the compound to the mucous membranes of the nasal passage or nasal cavity of the subject. Pharmaceutical compositions for nasal administration of the compound include therapeutically effective amounts of the compound prepared by well-known methods to be administered, for example, as a nasal spray, nasal drop, suspension, gel, ointment, cream or powder. Administration of the compound may also take place using a nasal tampon or nasal sponge.

The compounds may be administered per se (neat) or in the form of a pharmaceutically acceptable salt. When used in medicine, the salts should be both pharmacologically and pharmaceutically acceptable, but non-pharmaceutically acceptable salts may conveniently be used to prepare the free active compound or pharmaceutically acceptable salts thereof. Pharmacologically and pharmaceutically acceptable salts include, but are not limited to, those prepared from the following acids: hydrochloric, hydrobromic, sulphuric, nitric, phosphoric, maleic, acetic, salicyclic, p-toluenesulfonic, tartaric, citric, methanesulphonic, formic, malonic, succinic, naphthalene-2-sulphonic, and benzenesulphonic. Also, pharmaceutically acceptable salts can be prepared as alkaline metal or alkaline earth salts, such as sodium, potassium or calcium salts of the carboxylic acid group. Both simple and complex salts are possible.

In one embodiment, the compound is not ionic.

The compositions may also suitably include one or more preservatives, anti-oxidants, or the like.

The compounds can be administered orally. Thus, in any of the methods herein, the pharmaceutical composition can be administered orally. Alternatively, the pharmaceutical composition can be administered parenterally.

Some examples of techniques for the formulation and administration of the compounds may be found in *Remington: The Science and Practice of Pharmacy*, Lippincott Williams & Wilkins Publishing Co., $21^{st}$ addition, incorporated herein by reference.

In one embodiment, the compound may be chemically modified for administration in the form of a prodrug. As is known in the art, prodrugs liberate the active compound in vivo by enzymatic or chemical processes, and their preparation can be carried out without undue experimentation given the teachings herein and the knowledge available to one of skill in the art.

Any combination of one or more compounds, salts, prodrugs, metabolites, isotopically-labeled compounds, tautomers, isomers, enantiomers, diastereomers, and/or atropisomers is possible in the pharmaceutical composition.

In one embodiment, the compounds may be delivered using a sustained-release system, such as semipermeable matrices of solid hydrophobic polymers containing the therapeutic agent. Various forms of sustained-release materials are well known by those skilled in the art and can be prepared without undue experimentation. Sustained-release capsules may, depending on their chemical nature, release the compounds for a few hours, a few days, a few weeks to up to over 100 days. Depending on the chemical nature and the biological stability of the compound, additional strategies for stabilization may be employed.

In one embodiment, the pharmaceutical compositions contain the compound in an effective amount to achieve their intended purpose. In one embodiment, an effective amount means an amount sufficient to prevent or treat the disease. In one embodiment, to treat means to reduce the development of, inhibit the progression of, or ameliorate the symptoms of a disease in the subject being treated. In one embodiment, to treat means to reduce or inhibit the metastasis of a disease in the subject being treated. In one embodiment, to prevent means to administer prophylactically, e.g., in the case wherein in the opinion of the attending physician the subject's background, heredity, environment, occupational history, or the like, give rise to an expectation or increased probability that that subject is at risk of contracting the disease, even though at the time of diagnosis or administration that subject either does not yet have the disease or is asymptomatic of the disease. In one embodiment, prevention reduces the likelihood of an individual contracting the disease. In another embodiment, prevention reduces the number of individuals that contract the disease in a population.

Each of the prevention and/or treatment of the disease, for example, cancer, or a combination thereof, by administering to a subject in need thereof one or more compounds described herein, prodrug thereof, salt thereof, or a combination thereof, optionally in contact with a pharmaceutically acceptable carrier or excipient; the identification of a subject and determination of that subject's need for the treatment or prevention of cancer, weight loss accompanying cancer, pain accompanying cancer, metastasis therefrom, generalized wasting syndrome associated with cancer, or a combination thereof, by administering to a subject in need thereof one or more compounds described herein, prodrug thereof, salt thereof, or a combination thereof, optionally in contact with a pharmaceutically acceptable carrier or excipient; and the determination of the effective amount of the compound and route of administration can be carried out without undue experimentation by the skilled artisan in light of the detailed disclosure herein.

In one embodiment, the cancer is an ERK-dependent cancer associated with an extracellular signal-related kinase (ERK) pathway. In one embodiment, the cancer is one in which ERK is constitutively activated. In one embodiment, the cancer is such that if ERK is inhibited, then the cancer growth is inhibited. In one embodiment, the compound does not compete with ATP binding of the ERK. In one embodiment, upon administering the compound to a subject, the compound or metabolite thereof binds to ERK and inhibits the promotion of cancer, or inhibits or reduces the growth rate of cancer cells, or stops the growth completely or substantially completely. In one embodiment, upon administering the compound to a subject, the compound or metabolite thereof binds to ERK and induces apoptosis in a cancer cell or cell. In one embodiment, the subject does not develop drug resistance to the compound. The attending physician can readily determine when a subject develops drug resistance.

In one embodiment, the ERK pathway is adenosine triphosphate (ATP) independent.

In one embodiment, the cancer is associated with receptor tyrosine kinase (EGFR, HER2) overexpression.

In one embodiment, the cancer is associated with a Ras or BRaf mutation.

In one embodiment, the cancer is carcinoma, breast cancer, pancreatic cancer, non-small cell lung carcinoma, thyroid cancer, melanoma, seminoma, bladder cancer, liver cancer, kidney cancer, myelodysplastic syndrome, acute myelogenous leukemia, colorectal cancer, or a combination thereof.

One embodiment provides a method, comprising treating at least one cancer selected from the group consisting of carcinoma, breast cancer, pancreatic cancer, non-small cell lung carcinoma, thyroid cancer, melanoma, seminoma, bladder cancer, liver cancer, kidney cancer, myelodysplastic syndrome, acute myelogenous leukemia, colorectal cancer, or a combination thereof, by administering to a subject in need thereof one or more of subject compounds, prodrug thereof, salt thereof, or a combination thereof, optionally in contact with a pharmaceutically acceptable carrier or excipient.

One embodiment provides a method, comprising preventing at least one cancer selected from the group consisting of carcinoma, breast cancer, pancreatic cancer, non-small cell lung carcinoma, thyroid cancer, melanoma, seminoma, bladder cancer, liver cancer, kidney cancer, myelodysplastic syndrome, acute myelogenous leukemia, colorectal cancer, or a combination thereof, by administering to a subject in need thereof one or more of the subject compounds, prodrug thereof, salt thereof, or a combination thereof, optionally in contact with a pharmaceutically acceptable carrier or excipient.

EXAMPLES

The examples described herein are provided for purposes of illustration and are not intended to be limiting.

Example 1

Computer aided drug design (CADD) was used to identify small molecular weight compounds that inhibit ERK1/2-mediated phosphorylation of substrate proteins in an ATP-independent manner and inhibit cancer cell proliferation in in vitro and in vivo models. This approach targeted the DRS region of ERK2, such that the identified inhibitors containing a thiazolidinedione scaffold that may selectively regulate distinct ERK2 signaling functions. From those efforts, several compounds were identified that inhibit phosphorylation of selected ERK1/2 substrates, including D-domain containing substrates RSK-1 and caspase-9, and selectively inhibit cancer cell lines containing constitutively active ERK1/2 signaling.

The present inventors have identified a class of small molecules, based on a thienyl benzenesulfonate scaffold, which are putative inhibitors of substrates that interact with ERK1/2 through the FRS. The compounds were initially identified using virtual database screening followed by experimental assays. Validation of the scaffold was then achieved by designing analogs using the Site-Identification by Ligand Competitive Saturation (SILCS) approach, chemical synthesis and experimental evidence demonstrating inhibition of F-site containing proteins that comprise the activator protein-1 (AP-1) transcription factor complex. Correspondingly, melanoma cells containing mutated BRaf and active ERK1/2 signaling were selectively inhibited by the new compounds. These results provide further support for the feasibility of developing low-molecular weight compounds that can disrupt ERK1/2 substrate docking domains, thereby specifically inhibiting the functions of select substrate proteins that drive the proliferation and survival of cancer cells containing constitutively active ERK1/2 signaling.

Materials.

Test compounds were obtained from Chembridge Corporation (San Diego, Calif.). Test compound analogs were synthesized using reagent grade chemicals and solvents purchased from Sigma-Aldrich (St. Louis, Mo.), Alfa Aesar (Ward Hill, Mass.), Oakwood Chemicals (West Columbia, S.C.), and TCI America (Portland, Oreg.). 1H and 13C NMR spectra were recorded on Varian INOVA 400 MHz and Varian INOVA 500 MHz NMR spectrometers at 25° C. Chemical shifts are reported in parts per million (ppm). The residual solvent peak was used as an internal reference. The mass spectra were obtained on an Electrospray TOF (ESI-TOF) mass spectrometer (Bruker amaZon X). Prior to biological testing, final compounds were confirmed to be >95% pure by HPLC chromatography.

MEK1/2 inhibitor (U0126) was purchased from EMD Millipore (Billerica, Mass.), and the ATP-dependent pyrazolylpyrrole ERK2 inhibitor was purchased from Santa Cruz Biotechnology (Santa Cruz, Calif.). Unless indicated, all other chemicals listed below were purchased from Sigma Aldrich and/or Fisher Scientific. HeLa cervical carcinoma cells, Jurkat T-cell leukemia cells, A375 melanoma, and mutated BRaf inhibitor-resistant RPMI7951 cells were purchased from American Type Culture Collection (Manassas, Va.). Additional details are provided in the supplementary methods. Antibodies recognizing total c-Fos, FosB, Fra1, and c-Jun were purchased from Cell Signaling Technology (Beverly, Mass.). The phospho-specific ERK1/2 (pThr183/pTyr185) and α-tubulin antibodies were purchased from Sigma. Phosphorylation-specific antibodies against RSK-1 (pThr573, pSer380), MEK1/2 (pSer217/pSer221), EGFR (pTyr1068), or Elk-1 (pSer383) were purchased from Cell Signaling (Beverly, Mass.). Antibodies against total RSK-1, ERK2 and MEK1 were purchased from Santa Cruz Biotechnology.

Protein Expression and Purification.

(His)$_6$-tagged ERK2 wild type was expressed in *E. coli* and purified as described previously. See Supplementary Methods for more details.

Immunoblotting.

Analysis of protein expression levels, activity, and cell proliferation were done as previously described. Cells were washed with cold phosphate buffered saline (PBS, pH 7.2; Invitrogen) and protein lysates were collected with SDS-PAGE sample buffer (4% SDS, 5.7M α-mercaptoethanol, 0.2M Tris pH 6.8, 20% glycerol, 5 mM EDTA) or cold tissue lysis buffer (TLB; 20 mM Tris-HCl pH 7.4, 137 mM NaCl, 2 mM EDTA, 1% Triton X-100, 0.1% SDS, 25 mM (3-glycerophosphate, 2 mM sodium pyrophosphate, 10% glycerol, 1 mM sodium orthovanadate, 1 mM phenylmethylsulfonyl fluoride, 1 mM benzamidine). Lysates collected in TLB were centrifuged at 20,000 (xg) to remove insoluble material and then diluted with an equal volume of 2×SDS-sample buffer. Proteins were separated by SDS-PAGE, analyzed by immunoblotting, and detected using enhanced chemiluminescence (ECL, GE Healthcare, United Kingdom).

Cell Proliferation and Apoptosis Assays.

Cells were seeded at 25,000 cells/well in 96-well plate and cultured overnight. Cells were treated for 24 hours with various concentrations of compounds and cell viability or caspase 3/7 activity were measured according to manufacturer's instructions using the fluorescent Cell Titer Blue Assay (Promega) or luminescent Caspase 3/7 Glo Assay (Promega).

AP-1/SRE Promoter Luciferase Assays.

HeLa cells were seeded in 24-well plates (40,000 cells/well) and incubated 18 hours to achieve ~60-70% confluent. Cells were transfected with activator protein-1 (pAP1(PMA)-TA-Luc; Clontech) or the serum response element (pGL4.33-SRE; Promega) luciferase reporter plasmids (250 ng/well) using Lipofectamine™ (Invitrogen). After 16 hours, cells were pre-treated with varying amounts of compounds as indicated for 20 minutes, followed by stimulation with EGF (25 ng/mL) for 4.5 hr. In some experiments, cells transfected with the pAP1(PMA)-TA-Luc promoter and a constitutively active MEK1 mutant cDNA were treated with varying amounts of compounds during the last 4 hours of incubation. The luciferase activity in the cell extracts was determined with a Dual Luciferase Assay System (Promega) according to the manufacturer's instructions. Luciferase activities were monitored with a Lumat LB 9507 luminometer (Berthold Technology) and data were normalized to the amount of protein in each sample.

Computational Methods.

MD simulations were performed using the programs CHARMM and NAMD with the CHARMM22/CMAP additive force field with the TIP3P water model. Simulations initiated with the 3D structures of ERK2 in both the phosphorylated (active) (PDB ID 2ERK) and unphosphorylated (inactive) (PDB ID 1ERK) states. Site Identification by Ligand Competitive Saturation (SILCS) simulations for the FRS (site 5) of ERK2 were initiated the unphosphorylated ERK2 structure and included 1 M benzene and 1 M propane, as previously described. Diverse conformations for binding site identification and for database screening were performed via clustering was based on the root-mean-square differences of atomic positions (RMSD). Binding sites were identified in regions of the vicinity of sites 2, 3, 4 and FRS using the binding response method. Database screening used the program Dock against a virtual database of more than 1.5 million low-molecular weight commercially available compounds against each of the putative binding sites. Screenings involved a primary screen from which 50,000 compounds were selected followed by a secondary screen, which involved additional ligand relaxation and protein conformations, from which 1000 compounds were selected. Final selection of compounds for experimental assay involved maximizing chemical and structural diversity of the compounds, via fingerprint based clustering with the program MOE (Chemical Computing Group Inc.) as well as considering their physicochemical properties with respect to bioavailability. Each search resulted in approximately 150 compounds selected for each site of which a subset was obtained for experimental assay. The purity of compounds shown to have biological activity was verified by mass spectrometry.

Figure 4:
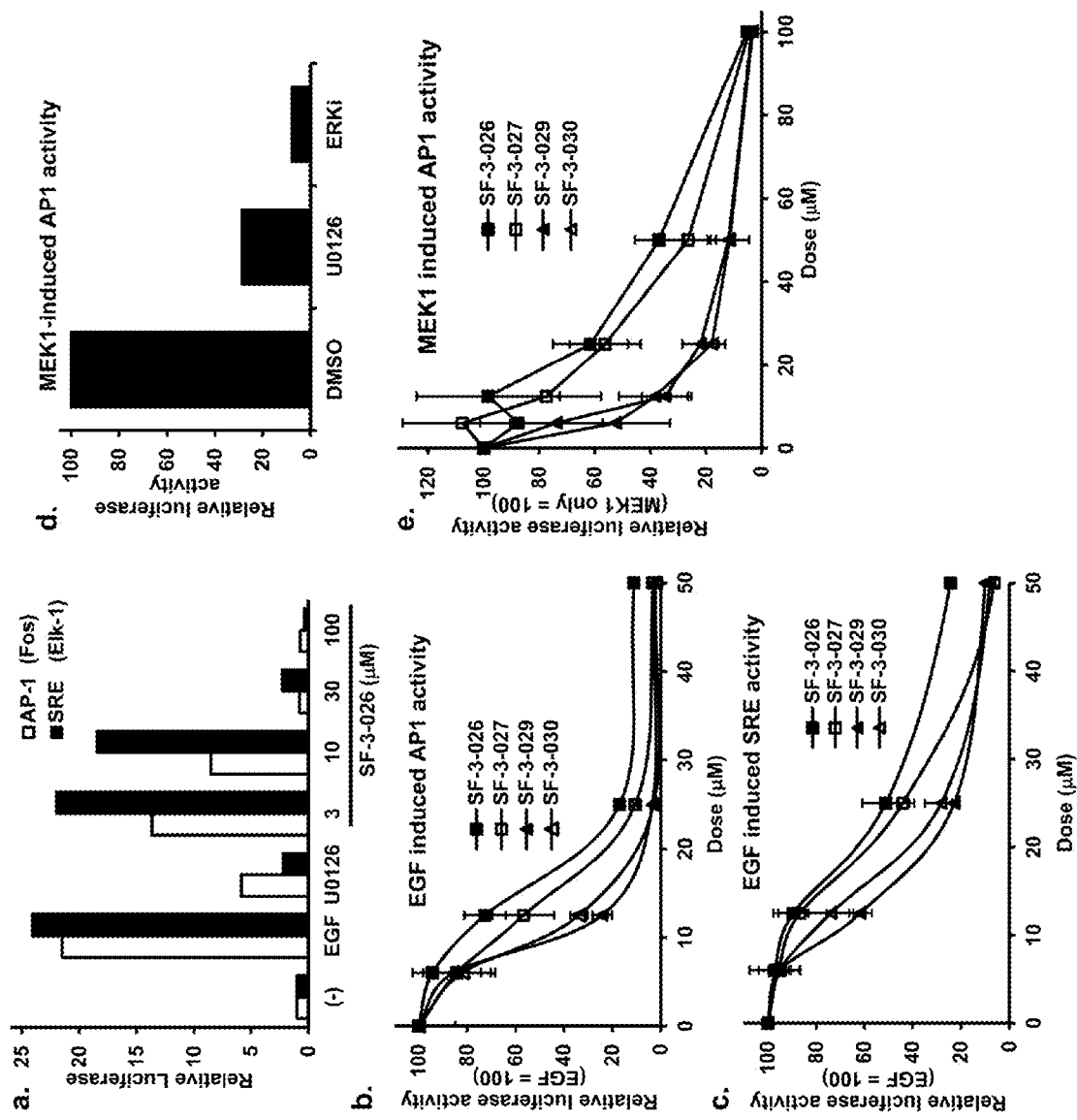
FIG. 4. Compound SF-3-026 and analogs inhibit SRE and AP-1 transcription factor function. (a) HeLa cells were transfected with constructs containing SRE or AP-1 promoters driving luciferase expression and then stimulated with EGF in the presence or absence of SF-3-026 for 4 hours followed by measurements of luciferase activity. Cells treated with U0126 were used as a positive inhibitor control. (b and c) HeLa cells were prepared and treated as in (a) with the indicated concentrations of SF-3-026 or analogs for 4 hours followed by the measurement of luciferase activity regulated by the SRE (b) or AP-1 (c) promoters. Data in (b and c) were normalized to EGF-only treatment and represent the mean and standard deviation from three independent experiments. (d) Compound SF-3-026 and analogs inhibit MEK1-induced AP-1 transcription factor function. HeLa cells were transfected with the AP-1 promoter construct and a constitutively active MEK1 mutant in the presence (10 μM) or absence of the MEK1/2 inhibitor (U0126) or an ATP-competitive ERK inhibitor (ERKi) for 4 hours followed by measurements of luciferase activity. (e) Cells expressing the AP-1 promoter and an active MEK-1 construct were treated with the indicated concentrations of SF-3-026 or analogs for 4 hours followed by the measurement of luciferase activity. Data in (e) were normalized to active MEK1-only treatment and represent the mean and standard deviation from three independent experiments.
Figure 5:
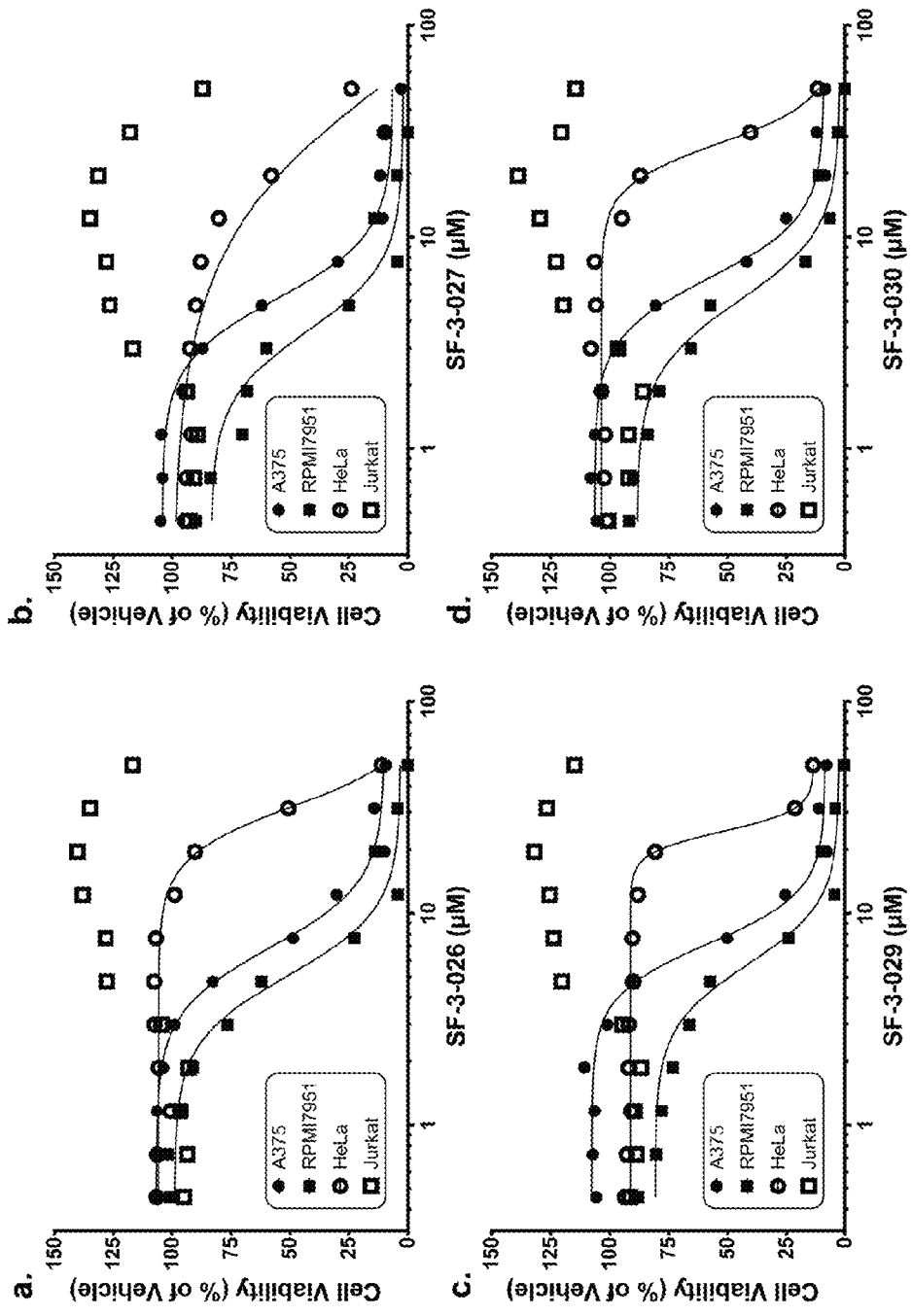
FIG. 5. Dose dependent inhibition of cancer cell proliferation in vitro by SF-3-026 and analogs. A375 (closes circles), RPM17951 (closed squares), HeLa (open circles), or Jurkat (open squares) cells were treated for 48 hours with indicated concentration of (a) SF-3-026, (b) SF-2-027, (c) SF-2-029, or (d) SF-2-030 and cell proliferation was assessed by the fluorescent Cell Titer Blue Assay. The corresponding $GI_{50}$ values are shown in Table 5. The data were reproduced in 3 separate experiments.

Prediction of ligand modifications were performed using ligand grid free energy scores (LGFE) based on the SILCS methodology. SILCS simulations were initiated from the 2.3.2-ERK2 crystal structure determined in the present work. Visualization of the SILCS Fragmaps (FIG. 2a) identified the region beyond the benzene ring of 2.3.2 as suitable for non-polar moieties. Subsequently, the analogs of 2.3.2 shown in FIG. 4 were modeled onto ERK2 starting from the 2.3.2-ERK2 crystal structure. Relative LGFE with respect to 2.3.2 were then determined and are presented in FIG. 2. Additional details of all the computational methods are included in Example 2.

In silico modeling and experimental assays have been utilized to identify small molecular weight compounds that selectively inhibit ERK2 interactions with substrate proteins by targeting unique docking sites and do not interfere with ATP binding. Computational approaches were applied to identify putative small molecule binding sites located on regions in the C terminus of ERK2 previously implicated via mutagenesis studies to be important for substrate binding. The 5 sites targeted, with the residues shown on the structure of ERK2 include the DRS, which was previously targeted in our laboratory, the FRS known to be involved in interactions with ERK1/2 substrates containing the F-site or DEF motifs and the focus of the current studies, and three putative sites that span the region between the DRS and FRS (Table 1).

Selection of ERK2 Docking Sites.

Putative inhibitor binding sites on the docking domain were identified using standard MD simulations of phosphorylated and unphosphorylated ERK2 and SILCS simulations, which includes propane and benzene along with water to facilitate the identification of concealed binding sites, to generate multiple conformations of ERK2. Clustering based on atomic spatial positions of the protein conformations generated in the simulations was performed to obtain multiple diverse conformations of the protein for both binding site identification and docking. Putative low molecular weight inhibitor binding sites were identified using the binding response (BR) algorithm. Presented in Table 2 are all sites identified at least once on both phosphorylated and unphosphorylated ERK2 for sites 2-4, along with the times each site was identified and the average BR score. Supplementary data in Table S3 presents the BR scores for the FRS analysis.

In the active conformation of ERK2 showing residues identifying the 2, 3, 4, DRS and FRS sites, activation lip residues, and the ATP binding site, the putative binding sites span a large portion of the C-terminal domain of ERK2, consistent with the range of residues indicated to be involved in ERK2-substrate proteins via mutational analysis (Table 1). Notable is the use of multiple conformations of ERK2 to identify the binding pockets and for use in screening (see below), thereby partially including protein flexibility in binding site identification and database screening. Accounting for protein flexibility is important when identifying inhibitors of protein-protein interactions as inhibitor-binding sites may not be present in the crystal structure but may occur during normal conformational fluctuations of the protein as sampled in the MD simulations. In the case of the FRS, the SILCS simulations facilitated sampling of conformations allowing for putative binding sites in that region to be identified.

Database Screening.

Primary database screening targeted 8 conformations for putative docking sites 2, 3 and 4, while 9 conformations were used for the FRS screen (Tables 2 and S3). Each ligand was individually docked against each conformation based on the total interaction energy, with scoring based on the most favorable normalized vdW attractive energy among all the protein conformations. Use of the vdW attractive energy eliminates compounds with favorable interaction energies dominated by electrostatic interactions but lacking sufficient steric complementarity with the protein. Normalization accounts for the upshift in the molecular weight (MW) of selected compounds when scoring is based on interaction energies. Normalization factors (Table 4) were selected to yield a median MW of the selected compounds closest to a target MW of 300 Da. The normalization factors are summarized in Table 4. The selection of low MW compounds is advantageous as such compounds should have improved bioavailability and will allow the introduction of functional groups to enhance biological activity during future optimization. From this procedure, the top 50,000 compounds were selected for each site and used in secondary screening.

Secondary screening involved more rigorous ligand optimization during docking and additional protein conformations were included to better account for protein flexibility. Each compound was again docked individually against each protein conformation with the most favorable energy over all the conformations taken as the score for each compound. Scoring was based on the normalized total ligand-protein interaction energies (Table 4). With the FRS, a large number of compounds with negatively charged groups were present in the top 1,000 compounds selected based on the normalized total interaction energy. Thus, the normalized vdW attractive energy was used for scoring. For each site the top 1000 compounds were selected.

Final compound selection emphasized chemical and structural diversity to maximize the identification of active compounds. Diversity was attained using fingerprint-based similarity clustering to group compounds into structurally similar clusters from which individual molecules were selected. This selection process also included bioavailability considerations.

Experimental Evaluation of Compounds and Effects on ERK1/2 Signaling.

From the in silico screen, potential ERK1/2 targeting compounds were evaluated for effects on ERK1/2-mediated phosphorylation events. One group of 7 structurally diverse compounds (FIG. 1a) were tested in EGF treated HeLa cells and identified compound 2.3.2 to inhibit ERK1/2-mediated phosphorylation of the transcription factor Elk-1, which contains both a D-domain and an F-site (FIG. 1b). Compounds 2.3.3, 2.3.4, and 2.3.5 also inhibited Elk-1 phosphorylation but to a lesser extent (FIG. 1b). Importantly, none of the compounds caused a corresponding inhibition of ERK1/2 activation, as measured by phosphorylation of the activation site residues, suggesting the compound's mechanism of action involved targeting ERK1/2 regulation of downstream events. While 2.3.2 inhibited ERK1/2-mediated Elk-1 phosphorylation, it appeared to be less potent for inhibiting ERK1/2-mediated phosphorylation of the D-domain containing substrate RSK-1 (FIG. 1c). Further support that 2.3.2 was acting on ERK1/2-mediated events was demonstrated by the lack of effects on ERK1/2 phosphorylation by MEK1/2 proteins, which interact with ERK1/2 through their D-domains, or autophosphorylation of the EGF receptor (FIG. 1c).

To provide additional evidence for the binding site of 2.3.2, crystallographic studies were undertaken and crystals of 2.3.2 bound to the inactive form of ERK2 were obtained (deposited in Protein Data Bank PDB ID: 3QYI). Upon inspection of the model that included protein and 46 water molecules, additional density was identified in a pocket vacated by Phe181/Leu182 located below the activation loop that includes residues Thr183 and Tyr185. Given that the densities of these two residues are well resolved, it was predicted that the elongated density filling this region was representative of 2.3.2. The irregular shape of the electron density fragment was accounted for by assuming that 2.3.2 binds in at least two orientations. In one of the modeled conformations, 2.3.2 appears to make hydrogen bonds to the backbone amides of Phe181 and Leu182; however, this should be taken with caution given the disordered and partially occupied nature of the ligand in the binding site. Thus, the data suggest that 2.3.2 is the first molecule identified to interact with ERK2 in the FRS region involved with regulating interactions with substrates containing an F-site. While the role of the FRS region in coordinating protein-protein interactions may be unique to ERK2, it is possible that in other kinases targeting of this site may result in inhibition of kinase activity. We have analyzed 2,314 structures from the Protein Data Bank that were identified by sequence alignment using E=10 as the threshold. Several structures were identified with non-trivial ligands (i.e. not components of the crystallization cocktail) overlapping somewhat with the area where 2.3.2 binds to ERK2. These include potential allosteric inhibitors of p38α and JNK. However none of these MAP kinases are known to harbor comparable FRS regions, although the potential for allosteric regulation of kinase activity via this site might be a common structural feature. A recent structure for the kinase domain of ERK5 indicates an FRS domain that is similar in sequence and structure to the ERK2 FRS.

It has to be emphasized that the observed difference omit electron density (i.e. $F_o-F_c$ map calculated in the absence of ligand) is by itself not conclusive of 2.3.2 binding to the FRS region of ERK2. However, the additional density observed with 2.3.2 was not observed for the ERK2 crystals obtained without ligand soaking. This indicates that the electron density is likely originating from 2.3.2 binding and not that of other components of the crystallization buffer (e.g. NDSB-256). Furthermore, it is clearly possible to place other molecules that were present in crystallization buffer (including NDSB-256) into the rather featureless electron density. Additional complication arises from the proximity of the crystal contact to the putative binding site, which may result in a binding mode that is somewhat distorted compared to what happens in solution. Thus, the crystallographic evidence presented can only suggest the possibility of the 2.3.2 binding in the detected location on the protein surface, and does not unequivocally prove it. Therefore, additional support for 2.3.2 and chemically related analogs regulating ERK1/2 functions through the FRS comes from further computational and biochemical studies in the following sections.

Further validation of 2.3.2 as a viable compound for future optimization involved the design and synthesis of chemically similar analogs using Site Identification by Ligand Competitive Saturation (SILCS) methodology. SILCS 3D FragMaps obtained from SILCS simulations initiated from the putative 2.3.2-ERK2 crystal structure are shown overlaid on the crystal structure obtained (FIG. 2a). The FragMaps represent the regions to which different type of functional groups bind, and include contributions from protein flexibility, desolvation and functional-group protein interactions. Visual analysis reveals the overlap of the aliphatic and aromatic SILCS FragMaps with the phenyl moiety of 2.3.2, with those FragMaps extending beyond the crystallographic position of the phenyl ring. This indicates that the addition of nonpolar moieties to this phenyl ring may improve affinity. Accordingly, synthetically-accessible chemical modifications of the phenyl ring were identified, modeled onto 2.3.2 bound to ERK2, and the relative SILCS ligand grid free energy (LGFE) scores were calculated and presented as a change in ligand grid free energy scores ($\Delta$LGFE) relative to 2.3.2 (FIG. 2b). As shown, hydrophobic modifications are indicated to increase activity (FIG. 2b). Accordingly, the p-CH3, biphenyl and napthyl analogs were synthesized and, along with 2.3.2, which is from now on referred to as SF-3-026, tested in biological assays.

ERK1/2 phosphorylation of Elk-1 regulates the serum response element that drives the transcription of c-Fos, another F-site containing ERK1/2 substrate. Therefore, initial testing of SF-3-026 and analogs evaluated the effects on growth factor-mediated expression of c-Fos and Fra1, another F-site containing member of the Fos family of proteins that form AP-1 transcription factor complexes. As shown in FIG. 2c, ERK1/2-mediated phosphorylation of c-Fos and Fra1 was decreased in EGF-treated HeLa cells that were pretreated with compounds and this correlated with a loss of total c-Fos and Fra1 protein. Both c-Fos and Fra1 showed a characteristic electrophoretic mobility shift, which has been attributed to phosphorylation by RSK1 and ERK1/2 proteins. These data are consistent with the role for ERK1/2 proteins in regulating the expression, stability, and transcription factor functions of Fos-family proteins. In support of the SILCS predictions, the compounds with the largest $\Delta$LGFE were the most effective at inhibiting the Fos family of proteins (FIG. 2c). For comparison, all compounds showed more potent inhibition of ERK1/2-mediated phosphorylation of Elk-1 as compared to the D-domain substrate RSK-1 and phosphorylation of ERK1/2 or MEK1/2 proteins was not affected at the dose tested (FIG. 2d).

Figure 2:
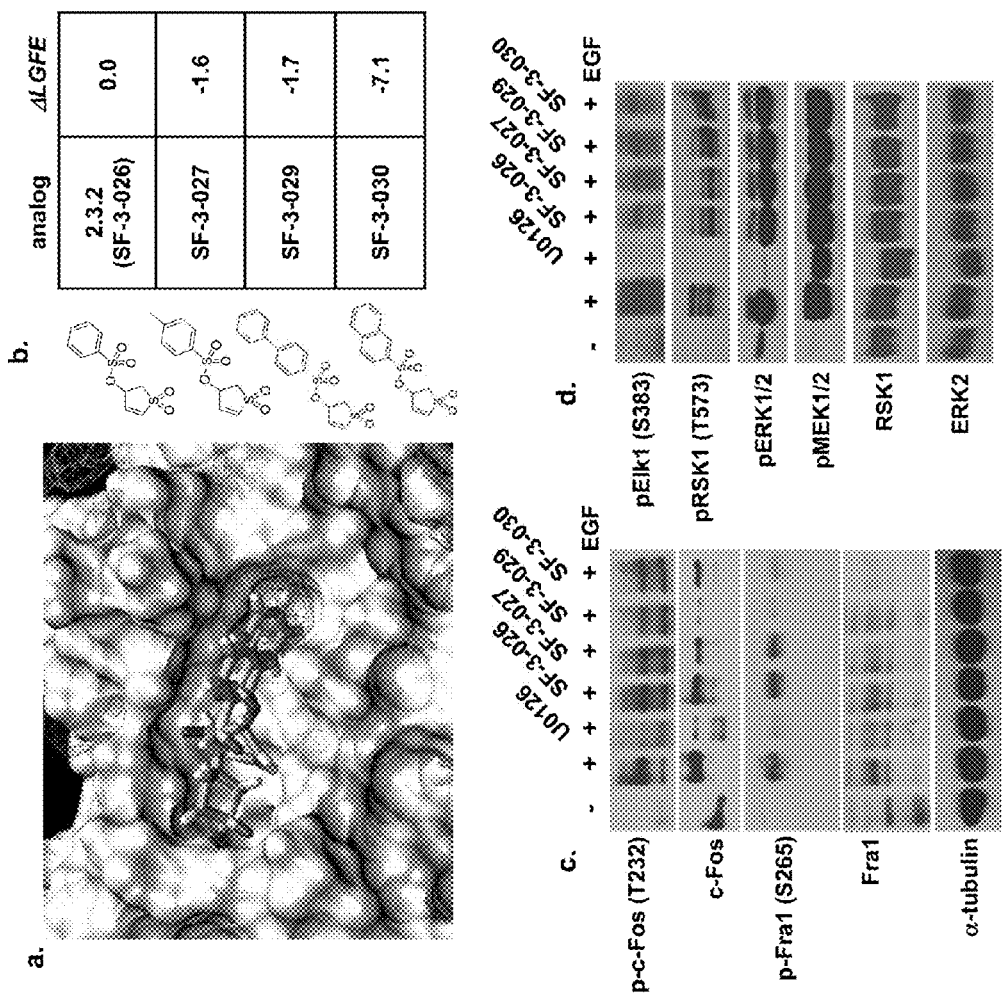
FIG. 2. SILCS identified analogs of 2.3.2 inhibit Elk-1 and c-Fos phosphorylation. (a) SILCS FragMaps overlaid onto the 2.3.2-ERK2 crystallographic structure. 3D probability distributions are shown for aliphatic and aromatic functional groups. (b) The structures and change in ligand grid free energy scores (ΔLGFE) for 2.3.2 (SF-3-026) and analogs (SF-2-027, SF-2-029, SF-2-030. (c) SF-3-026 and related compounds selectively inhibit F-site containing substrates. HeLa cells were pretreated with 50 μM of SF-3-026 and analogs followed by stimulation with EGF as in FIG. 1b. Cell lysates were immunoblotted for total and phosphorylated c-Fos (p-c-Fos T232) or Fra1 (p-Fra1 S265). α-tubulin expression was used as a protein loading control. (d) Lysates from cells treated as in FIG. 2c were immunoblotted for phosphorylated Elk1, RSK1, ERK1/2 and MEK1/2. Total RSK1 and ERK2 are shown as a protein loading control. Data are representative of three independent experiments.
Figure 3:
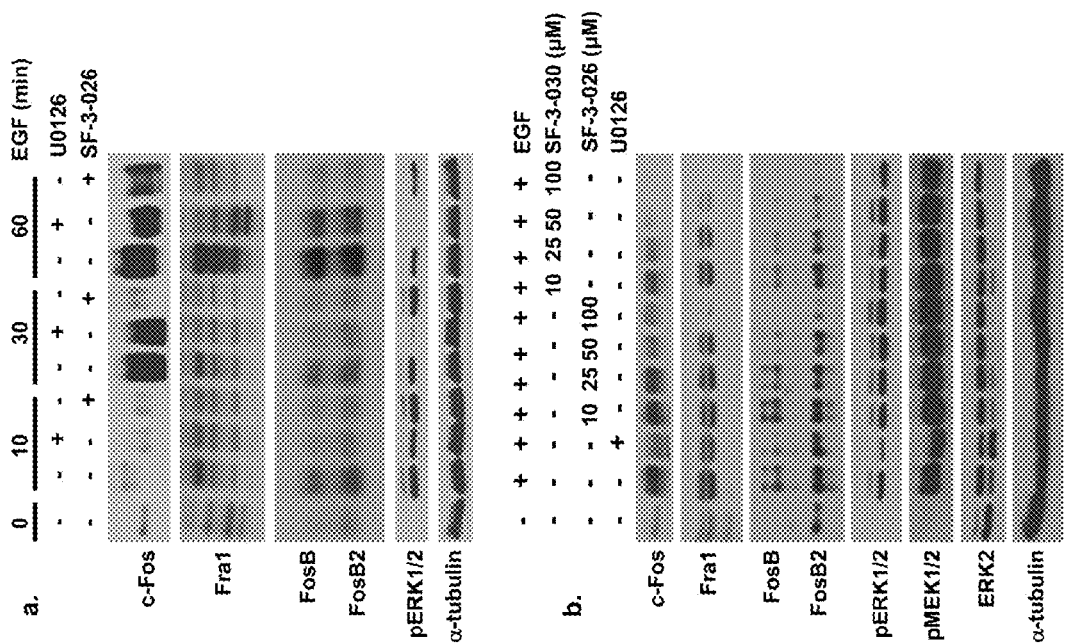
FIG. 3. EGF-mediated induction of AP-1 proteins is inhibited by SF-3-026 and SF-3-030. (a) HeLa cells were treated for 10, 30, or 60 min. with EGF (25 ng/mL) in the presence of 50 μM SF-3-026 or 10 μM U0126. Protein lysates were immunoblotted for c-Fos, Fra1, FosB and FosB2. Phosphorylated ERK1/2 is not affected by SF-3-026 and α-tubulin expression is shown for a protein loading control. (b) Protein lysates from HeLa cells treated for 30 min. with EGF in the absence or presence of 10, 25, 50, or 100 μM of SF-3-026 or SF-3-030 were immunoblotted for c-Fos, Fra1, FosB, FosB2, as well as phosphorylated ERK1/2 and MEK1/2. Total ERK2 and α-tubulin expression are shown for protein loading controls. Data are representative of three independent experiments.

The reported half-life for c-Fos is ~10 minutes and growth factor-mediated stabilization of c-Fos protein expression can be observed within 30-60 minutes, whereas stabilization of Fra1 protein is delayed due to AP-1 regulation of the Fra1 promoter. Thus, growth factor-mediated induction of c-Fos, Fra1, and FosB expression was evaluated following treatment with SF-3-026. First, the kinetics of c-Fos, Fra1, and FosB expression in the context of HeLa cells pretreated with SF-3-026 and the treated for 10-60 minutes with EGF showed a robust expression of c-Fos after 30 minutes exposure to EGF, whereas the Fra1 and FosB expression was observed after 60 minutes (FIG. 3a). Pre-treatment of HeLa cells with SF-3-026 caused a dramatic inhibition of EGF-induced c-Fos, Fra1, and FosB expression (FIG. 3a). Next, the dose-response effects of SF-3-026 on AP-1 proteins were compared to SF-3-030 in HeLa cells treated with EGF for 30 minutes when c-Fos levels are elevated. Both compounds showed a dosed dependent inhibition of c-Fos, Fra1, and FosB expression with SF-3-030 showing higher potency (FIG. 3b). Similar to FIGS. 1 and 2, phosphorylation of ERK1/2 and MEK1/2 was largely unaffected suggesting the compounds were acting downstream of these signaling proteins.

To test whether inhibition of the Fos family of proteins by SF-3-026 and its analogs correlated with inhibition of transcription factor functions, HeLa cells expressing luciferase constructs driven by the activator protein-1 (AP-1) or serum response element (SRE) promoters, which are regulated by Fos family or Elk-1 proteins, respectively, were treated with the test compounds in the context of EGF stimulation. As shown in FIG. 4a, SF-3-026 inhibited promoter activity in a dose-dependent manner with selectivity towards the AP-1 promoter. Similarly, the SF-3-026 and analogs showed a dose dependent and selective inhibition of AP-1 versus the SRE promoter with SF-3-029 and SF-3-030 showing the most potent inhibition of the AP-1 promoter with $IC_{50}$ values of less than 10 $\mu$M (FIGS. 4b and c). To further demonstrate the targeting of ERK1/2-mediated transcription, AP-1 promoter activity was measured in HeLa cells expressing an active MEK1 mutant, which only activates ERK1/2. As shown in FIG. 4d, MEK1-induced AP-1 promoter activity could be inhibited with the MEK1/2 inhibitor, U0126, or a previously reported ATP-competitive pyrazolylpyrrole ERK inhibitor. Similarly, SF-3-026 and its analogs caused dose-dependent inhibition of AP-1 promoter activity with SF-3-029 and SF-3-030 showing $IC_{50}$ values around 5-10 $\mu$M as compared to SF-3-026 and SF-3-027 with $IC_{50}$ values of ~40 $\mu$M (FIG. 4e). These data provide further support for the SILCS predicted modifications to improve potency. In addition, the selectivity towards AP-1 mediated transcription indicates the compounds may directly target the inhibition of Fos family proteins.

It was next determined whether inhibition of AP-1 proteins by SF-3-026 and analogs affected the proliferation of cancer cells driven by mutations that constitutively activate the ERK1/2 pathway. For these experiments, A375 and RPMI7951 melanoma cells, which have a valine to glutamate mutation on residue 600 in BRaf that causes constitutive ERK1/2 activation, were chosen. Moreover, RPMI7951 cells are resistant to clinically used BRaf inhibitors due to overexpression of MAP3K8 (the gene encoding COT/Tp12) that re-activates ERK1/2 signaling. Both melanoma cells lines were treated with varying doses of SF-3-026 or analogs and cell viability was compared to HeLa cervical carcinoma and Jurkat T-cell leukemia cells, which are p53 defective but contain no known activating mutations in the ERK1/2 pathway. Compound SF-3-026 and the analogs showed a dose-dependent inhibition of each cell line; however the A375 and RPMI7951 melanoma cells were more sensitive to the test compounds with $GI_{50}$ values in the low $\mu$M range and several fold lower than the HeLa or Jurkat cells even when adjusted for individual cell growth rates (FIG. 5a-d, Table 5).

TABLE 5

| $GI_{50}$ values ($\mu$M) for SF-3-026 and analogs in cancer cell lines. | | | | |
| --- | --- | --- | --- | --- |
| $GI_{50}$ | A375 | RPMI7951 | HeLa | Jurkat |
| SF-3-026 | 7.8 | 5.1 | 32 | >50 |
| SF-3-027 | 5.5 | 3.1 | 22 | >50 |
| SF-3-029 | 7.9 | 4.9 | 25 | >50 |
| SF-3-030 | 7.1 | 4.6 | 29 | >50 |

Figure 6:
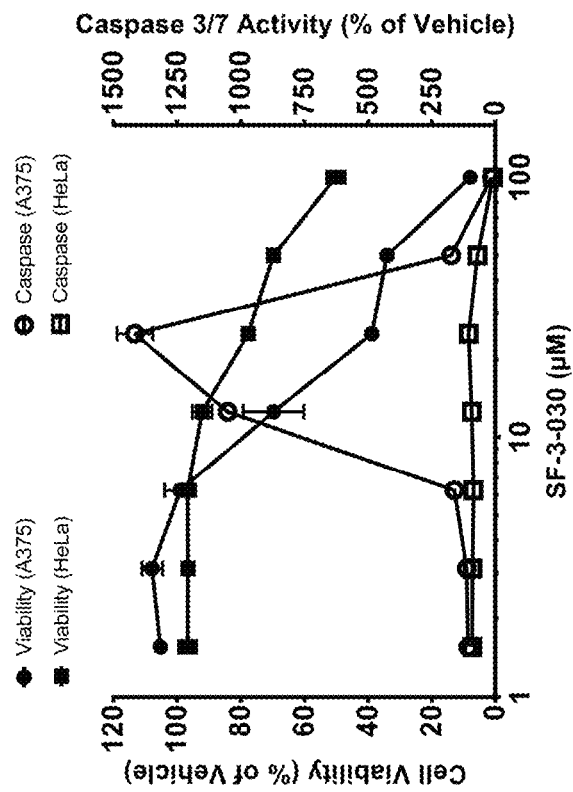
FIG. 6. SF-3-030 induces growth inhibition and apoptosis in A375 melanoma cells. A375 were seeded in a 96-well plate and incubated for 18-20 hours. Cells were treated with varying concentrations of SF-3-030 and allowed to incubate for an additional 24 hours. Cell viability was measured using the fluorescent Cell Titer Blue Assay and caspase 3/7 activity was measured using the luminescent Caspase 3/7 Glo Assay. Data represent the average of two experiments performed in duplicate.

To test whether the inhibition of cell proliferation was due to an apoptotic response, A375 and HeLa cells were treated with varying doses of SF-3-030 and cell viability along with caspase 3/7 activity was measured. Treatment with SF-3-030 caused a dose dependent increase in caspase 3/7 activity in A375 cells that correlated with decreased viability (FIG. 6). However, HeLa cells did not show increased caspase 3/7 activity and growth inhibition of these cells, as well as the A375 cells, at higher doses (>25 $\mu$M) may be due to non-specific toxicity of the compounds (FIG. 6).

Figure 7:
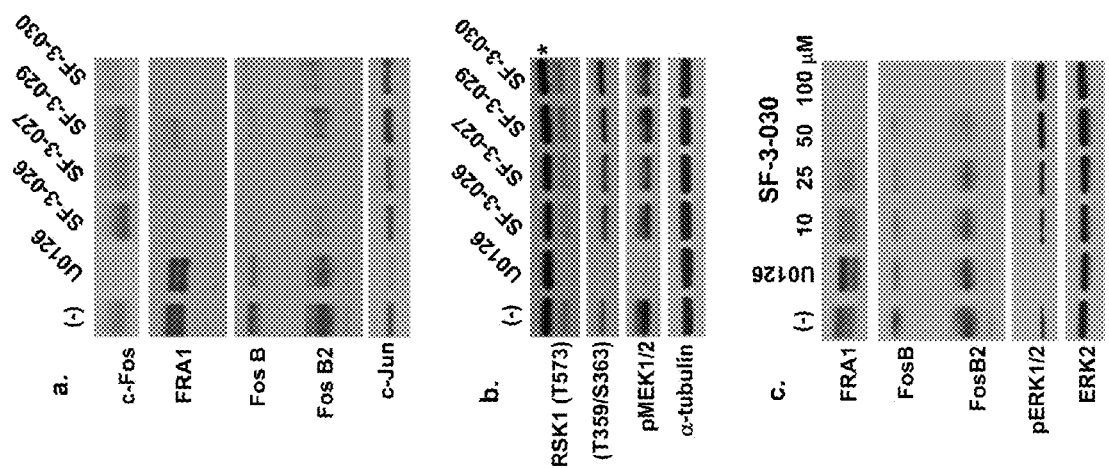
FIG. 7. SF-3-026 and analogs inhibit Fos family proteins in melanoma cells. (a) A375 cells treated with 10 μM U0126 or 100 μM of SF-3-026 and analogs were immunoblotted for c-Fos, Fra1, FosB, FosB2, or c-Jun. (b) A375 protein lysates treated as in (a) were immunoblotted for phosphorylated Elk1, RSK1, ERK1/2, or MEK1/2. *indicates a non-specific reactive band. (c) Dose dependent inhibition of AP-1 proteins in A375 cells treated for 1 hour with SF-0-026 or SF-3-030. Phosphorylated and total ERK2 are shown for reference.

Consistent with a role for AP-1 in promoting A375 cell proliferation, reduced expression of c-Fos, Fra1, FosB, and FosB2 proteins was observed in A375 cells treated for 1 hour with a single dose of the SF-3-026 analogs (FIG. 7a). Noteworthy is the significant inhibition of all Fos family proteins in cells treated with SF-3-030 and, and unlike the MEK1/2 inhibitor, none of the compounds affected the levels of c-Jun expression (FIG. 7a). The AP-1 complex partner c-Jun is known to contain only a D-domain for mediating interactions with MAP kinases. Similarly, SF-3-026 or the analogs had no effect on the phosphorylation of RSK-1, a D-domain containing ERK1/2 substrate, or MEK1/2 (FIG. 7b). Thus, these findings suggest that the compounds selectively inhibit F-site containing Fos family proteins in cells with activated ERK1/2 signaling. In addition, compound SF-3-030 caused a dose-dependent inhibition of Fra1, FosB, and FosB2 expression in A375 cells with no inhibitory effect on ERK1/2 phosphorylation (FIG. 7c). The inhibition of the AP-1 proteins with 10 μM of SF-3-030 correlated with the increase in caspase 3/7 activity suggesting that partial loss of Fos proteins is sufficient to sensitize mutated BRaf-driven melanoma cells to undergo apoptosis.

Figure 8:
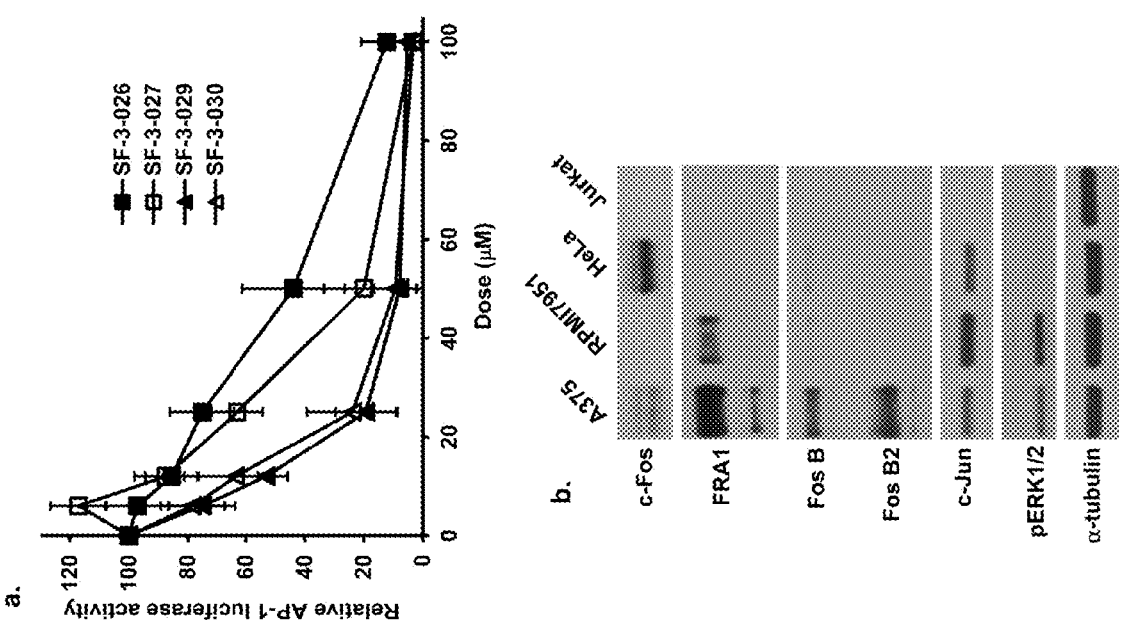
FIG. 8. SF-3-026 analogs inhibit AP-1 mediated transcription in melanoma cells. (a) A375 cells expressing the AP-1 promoter construct were treated with 6.25, 12.5, 25, 50 or 100 μM of SF-3-026 analogs for 4 hours followed by measurements of luciferase activity. (b) Relative expression levels of AP-1 proteins in cancer cell lines. Protein lysates from A375, RPMI7951, HeLa, or Jurkat cells were immunoblotted for c-Fos, Fra1, FosB, FosB2, c-Jun, or phosphorylated ERK1/2 (pERK1/2). α-tubulin expression is shown for a protein loading control.

As would be expected with loss of Fos family proteins, AP-1 mediated transcription in A375 cells was also inhibited in a dose-dependent manner by the SF-3-026 analogs (FIG. 8a). To evaluate whether targeting AP-1 proteins could explain the difference in sensitivity between the melanoma cells and the HeLa or Jurkat cells, we evaluated the basal expression of AP-1 proteins in the four cell lines evaluated in Table 5. When normalized to α-tubulin expression, all AP-1 proteins evaluated were expressed in A375 cells, which also contained the highest basal expression of Fra1 and FosB proteins as compared to the other cells (FIG. 8b). Fra1 expression was also found in RPMI7951 cells but not in HeLa or Jurkat cells. As expected, ERK1/2 phosphorylation was elevated in the BRaf mutated melanoma cells and highest in the drug resistant RPMI7951 cells (FIG. 8b). Interestingly, HeLa cells showed the highest level of basal c-Fos expression, which could explain their increased sensitivity to growth inhibition when treated with the compounds compared to the Jurkat cells that have undetectable levels of the AP-1 proteins when normalized to α-tubulin expression (FIG. 8b). However, given the lack of expression of Fra1 in the HeLa cells, these data indicate that targeted inhibition of AP-1 complex proteins, in particular Fra1, using SF-3-026 and related compounds will sensitize melanoma cells containing mutated BRaf to growth inhibition and apoptosis.

The current findings provide evidence that compounds containing a thienyl benzenesulfonate scaffold can target ERK1/2 signaling and selectively inhibit the expression of Fos family proteins involved in AP-1 regulated transcription. A variety of cancer types have been associated with dysregulated AP-1 transcription factor components. Thus, targeted inhibition of AP-1 functions may sensitize cancer cells with activated ERK1/2 signaling to growth inhibition and be used to augment the effects of anti-cancer drugs. Targeted inhibition of the ERK1/2 signaling has received much attention given the presence of activating mutations in receptor tyrosine kinases, Ras G-proteins, and BRaf. However, therapies targeting mutated BRaf or MEK1/2 proteins invariably lead to drug resistance due to alternative mechanisms to activate ERK1/2 and recent efforts to directly inhibit ERK1/2 proteins are being tested. Current small molecule kinase inhibitors being used or evaluated in the clinic act by competing with ATP binding or affect allosteric sites in the catalytic domain that causes complete kinase inhibition. A frequent cause of resistance to kinase inhibitors is the development of mutations in the ATP binding and catalytic site, which subsequently reduce inhibitor interactions and efficacy.

Alternatively, the current studies have identified a new class of compounds that selectively inhibit ERK1/2 signaling functions through F-site containing substrates, such as Fos proteins, but have limited effects on D-domain containing substrates, such as c-Jun or RSK1. Stabilization of the c-Jun through ERK1/2-mediated phosphorylation has been reported to promote proliferation of melanoma cells. However, in the current studies, inhibition of F-site containing Fos proteins and their functions in AP-1 transcription appears to be sufficient to sensitize melanoma cells, whose proliferation and survival depend upon on mutated BRaf and activated ERK1/2, to growth inhibition and cell death. It should be noted that the compounds mechanism of action may be different with different types of melanoma. As shown in Table 5, the $GI_{50}$, for the compounds are similar for A375 and RPMI7951 cells, despite varying expression levels for AP-1 proteins (FIG. 8b). Nonetheless, common to both melanoma cell lines is the expression of Fra1, whose inhibition may be sufficient to sensitize these cells to growth inhibition. Given that the compounds show selective inhibition of ERK1/2 substrates, we propose that targeting specific ERK1/2 signaling functions represents a more subtle approach to inhibiting cancer cell proliferation with reduced development of drug resistance and off-target toxicity.

There are a limited number of studies reporting the discovery of small molecule inhibitors of MAP kinase substrate docking sites. An earlier report described the identification of substrate selective inhibitors of the p38α MAP kinase as a potential approach to improve selectivity in regulating inflammatory responses. These studies found, by using deuterium exchange mass spectrometry, that the inhibitor targeted the active site of p38α MAP kinase and caused perturbations in residues that made up the DRS region on this kinase, which allowed the inhibitor to discriminate between the D-domain containing substrates MK2 and ATF2. A recent study has reported a natural product, zuonin A, targets the DRS on JNK MAP kinase and inhibits phosphorylation of c-Jun. Similarly, BI-78D3 was a small molecule identified to compete with a D-domain containing peptide found on the JNK interacting protein-1 (JIP1) and interactions with JNK1. Other screening approaches have identified novel compounds that bind to exposed allosteric sites on the JNK or p38 MAP kinase's surface and are ATP independent. While it is not known whether these compounds have differential effects on substrate proteins, this represents an alternative approach for identifying novel kinase inhibitors with improved selectivity over inhibitors that target highly conserved ATP binding sites.

While the present results indicate selective inhibition of the phosphorylation of substrate proteins by the studied inhibitors, selectivity is not absolute. This is evident in the substrate phosphorylation results showing inhibition of the D-domain substrate at higher concentrations of test compound (FIGS. 1 and 2). In addition, partial specificity was previously demonstrated by DRS targeted inhibitors, which inhibit ERK-mediated caspase-9 and RSK-1 phosphorylation and sensitize transformed cells to undergo apoptosis. Two factors may contribute to this lack of absolute specificity. First, the interaction between ERK2 and substrate may involve a relatively large portion of the docking domain such that interactions with more than one of the spatially adjacent sites may occur. While the structure of a full substrate protein bound to ERK2 is not available, structures of D-domain peptides from hematopoietic protein tyrosine phosphatase (PDB ID: 2GPH) and MAP kinase phosphatase-3 (PDB ID: 2FYS and 1HZM) are available. These peptides bind primarily to the DRS, though the C-terminal regions of the peptides extend towards other putative binding sites. Such additional interactions may be anticipated to lead to compounds binding to a given site on the docking domains to partially block interactions of substrate proteins not primarily interacting with those sites.

In the context of substrate interactions with the FRS on ERK, conformational changes associated with the active phosphorylated form of ERK2 were reported to promote interactions with F-site substrates. Recently, studies using D-domain or F-site specific peptides reported that there was little communication between the DRS and FRS on ERK2 when one site was occupied with a peptide. Nonetheless, occupancy at either site with a substrate protein may lead to conformational perturbations on either the structural and/or dynamical levels that regulate the formation of signaling complexes.

In summary, a combination of computational and experimental methods has been used to identify a class of low-molecular weight compounds that regulate the expression and function of F-site containing ERK1/2 substrates involved in regulating transcription and promoting cancer cell proliferation. The availability of these compounds will facilitate investigations into the biological function of ERK1/2-mediated signaling using chemical biology and potentially lead to the development of novel therapeutic agents. In addition, the successful identification of ATP-independent substrate-specific inhibitors of ERK1/2 is anticipated to open the door for similar ligand design strategies targeting protein-protein interactions in systems where a given protein has multiple interacting partners.

Example 2

Materials. Test compounds were solubilized in spectrophotometric grade dimethyl sulfoxide (DMSO) and stored as 25 mM stocks at −20° C. Unless indicated, all chemicals were purchased from Sigma Aldrich (St. Louis, Mo.) and/or Fisher Scientific. All cell lines were purchased from American Type Culture Collection (ATCC, Manassas, Va.) and maintained in complete medium consisting of Dulbecco's modified Eagle medium (DMEM) plus 10% fetal bovine serum (FBS, Atlanta Biologicals, Lawrenceville, Ga.) and antibiotics (penicillin, 100 U/ml; streptomycin, 100 µg/ml) (Invitrogen, Carlsbad, Calif.). Epidermal growth factor (EGF) was purchased from Sigma (St. Louis, Mo.) and used at final concentrations of 25 ng/ml. U0126 (Calbiochem) or the ATP-competitive pyrazolylpyrrole ERK inhibitor (Santa Cruz Biotech.) were used at final concentrations of 10 µM.

Protein Expression and Purification.

ERK2 transformed cells were grown in LB medium with 100 mg/ml ampicillin and protein expression was induced by 0.5 mM isopropyl-B-D-thiogalactoside (IPTG) for 4 hours. Protein purification was performed on ice or at 4° C. The cells were harvested by centrifugation and resuspended in lysis buffer (50 mM sodium phosphate, 300 mM NaCl, 10% glycerol, pH 7.8) supplemented with protease inhibitors phenylmethylsulfonylfluoride (PMSF, 1 mM) and benzamidine (10 mM). Lysozyme was added and the mixture sonicated followed by centrifugation at 10,000 rpm for 45 minutes. The cleared lysate was loaded onto a $Co^{2+}$ charged resin (Talon, Clontech) and the bound protein washed with 50 mM sodium phosphate, 300 mM NaCl, 10% glycerol, 20 mM imidazole (pH 7.8) and eluted with increasing concentrations of imidazole. Protein-containing fractions and purity of the fractions were determined by SDS-PAGE electrophoresis, concentrated and dialyzed. Protein concentration was determined by UV and/or Bradford method.

Crystallization, Data Collection and Model Refinement.

Crystallization was performed with the sitting-drop vapor-diffusion method. The initial condition was obtained from the Classics II Suite (Qiagen, Valencia, Calif.) containing polyethylene glycol (PEG) 3350 (w/v, 25%) in a BIS-TRIS buffer (100 mM, pH 6.5). Subsequent screening against Additive Screen (Hampton Research, Aliso Viejo, Calif.) showed that incorporation of 100 mM Sodium Malonate and 100 mM NDSB-256 into this precipitant could significantly improve the quality of crystals. In the final crystallization experiment, 25 mM compound 2.3.2 dissolved in DMSO was diluted by 100 fold in $H_2O$, equal volume of protein and diluted ligand was mixed, following which 71% volume of protein-ligand mixture was mixed with 29% volume of precipitant (BIS-TRIS, 100 mM, pH 6.5; PEG 3350, 25%; sodium malonate, 100 mM, pH7.0, and 100 mM NDSB-256) and equilibrated against the reservoir (70 µL). Crystals grew within 10 days at 22 C. Crystals were harvested, cryo-protected with the precipitant supplemented with 0.25 mM ligand and flash cooled in liquid nitrogen before data collection. X-ray diffraction data were collected at Stanford Synchrotron Radiation Lightsource (beamline 7-1). Diffraction images were processed using DENZO/SCALEPACK. The structure of ERK2/2.3.2 complex was solved by molecular replacement using PHASER with the structure of the unliganded protein as starting model (PDB ID 1ERK). This was followed by iterative manual model rebuilding using COOT and model refinement using REFMAC.

Computational Methods

MD Simulations.

Simulations were initiated with the 3D structures of ERK2 in both the phosphorylated (active) (PDB ID 2ERK) and unphosphorylated (inactive) (PDB ID 1ERK) states retrieved from the Protein Data Bank. The program Reduce was used to add hydrogen atoms and optimize the orientations of the sidechain OH, SH, $NH_3^+$, —S—$CH_3$, and amide moieties, as well as the imidazole rings of the histidines. To obtain multiple conformations of the putative binding sites in ERK2 suitable for database screening MD simulations were performed with the programs CHARMM and NAMD. Calculations used the CHARMM22 all-atom protein force field including the CMAP backbone energy correction. Simulations for sites 2, 3 and 4 were based on a truncated octahedron periodic system (112 Å edge length) run in CHARMM while those for site 5 were based on a cubic system (98 Å edge length) run in NAMD. Preparation for the MD simulations involved overlaying the structures of phosphorylated and unphosphorylated ERK2 with pre-equilibrated truncated octahedron or cubic boxes of TIP3P water that contained 150 mM NaCl. Solvent molecules with non-hydrogen atoms within 2.8 Å of protein non-hydrogen atoms were deleted. Each system was minimized and heated to 298K at a rate of 10K/ps and equilibrated in the NPT ensemble (1 atm, 298K) for 5 ns. Simulations were performed with a 2 fs integration timestep using the SHAKE algorithm to constrain covalent bonds to hydrogens. Electrostatic forces were calculated with the particle mesh Ewald (PME) method using a real space cutoff of 12 Å with a kappa value of 0.4 $Å^{-1}$ and a 4th order spline interpolation. Lennard-Jones (LJ) forces were truncated with a cutoff distance of 12 Å with smoothing performed using a force switching function starting at 10 Å. Production MD simulations were performed in the NPT (1 atm, 298K) ensemble for 30 ns, with time frames saved every 1 ps for analysis. Simulations in the presence of the 2.3.2 were performed following the same protocol where orientation 1 of the inhibitor along with the remainder of the crystal structure was used to initiate the simulation, with the inhibitor being modeled using the CHARMM General Force Field.

In addition, Site Identification by Ligand Competitive Saturation (SILCS) simulations for the FRS (site 5) of ERK2 were performed using the unphosphorylated ERK2 structure to obtain additional conformations. A box containing an aqueous solution of benzene and propane was prepared by placing TIP3P water on a 105 Å cubic grid with 3 Å spacing, and replacing TIP3P with propane and benzene molecules on every third grid point, from which either propane or benzene were randomly deleted, yielding ten distinct solutions of TIP3P, ~1 M propane, and ~1 M benzene. Ten ERK2-solution systems were generated by overlaying the structure of unphosphorylated ERK2 with the ten boxes of aqueous propane-benzene solution, removing overlapping propane, benzene, and water molecules with a non-hydrogen atom within 2 Å from protein non-hydrogen atoms, and replacing three randomly selected water molecules with sodium ions to neutralize the system. The final systems were 88×63×63 Å rectangular boxes to accommodate the protein, which has maximum dimensions of 77×51×46 Å. Minimization was then performed for 500 steepest descent steps with all protein atoms harmonically restrained with a force constant of 1 kcal/molÅ$^2$ followed by heating to 298K at a rate of 25K/ps and equilibration in the NPT ensemble (1 atm, 298K) for 20 ps with a 2 fs integration timestep using the SHAKE algorithm to constrain covalent bonds to hydrogen atoms. In the production phase, much weaker harmonic positional restraints were applied only on Cα atoms with a force constant of 0.01 kcal/molÅ$^2$ to prevent rotation of the protein in the primary simulation box. Production MD simulations were performed in the NPT ensemble (1 atm, 298K) for 20 ns, yielding a total of 200 ns of simulation time with time frames saved every 2 ps. Electrostatic forces were calculated using PME with a real space cutoff of 8 Å with a kappa value of 0.32 Å$^{-1}$ and a 6th order spline interpolation. LJ forces were truncated with a cutoff distance of 8 Å with smoothing performed using a force switching function starting at 5 Å.

Selection of Conformationally Diverse Structures.

To identify unique conformations of ERK2 for the identification of putative binding sites on the docking domain, conformations from the 30 ns MD simulations of phosphorylated and unphosphorylated ERK2 were subjected to Cartesian clustering. Clustering was based on the root-mean-square differences (RMSD) of all non-hydrogen atoms, yielding 10 and 9 distinct clusters for phosphorylated and unphosphorylated ERK2, respectively, using a RMS clustering radius of 0.5 Å. Representative conformations were selected from each cluster. These conformations as well as the X-ray crystallographic structures of phosphorylated and unphosphorylated ERK2 yielded 21 conformations that were initially used to identify putative docking domain binding pockets. Of the selected conformations eight conformations with maximal RMSD with respect to each other (four from phosphorylated and unphosphorylated ERK2) were used for the primary database screens with all conformations used for the secondary screen.

In the case of the FRS/site 5, clustering was performed based on the spatial position of non-hydrogen atoms defining that site (Leu198, His230, Tyr231, Leu232, Leu235, and Tyr261). RMSD based clustering, using the neural network based ART-2 algorithm, showed the presence of 6, 5 and 6 clusters from the phosphorylated ERK2 and unphosphorylated ERK2 MD simulations and the SILCS simulations based on RMS radii of 0.8 Å, 0.96 Å, and 0.8 Å, respectively. Representative structures were taken from each cluster, yielding a total of 18 conformations to be used for additional binding site analysis focused on site 5 and database screening. For primary screening the nine most diverse conformations, based on RMS differences, were selected individually from the phosphorylated and unphosphorylated ERK2 MD simulations and the SILCS simulations with all 18 conformations used for secondary screening.

Identification of Putative Binding Sites.

Putative binding sites were identified using the binding response method. To prepare the structures for binding pocket identification as well as docking, AMBER99 atomic partial charges were assigned using the program Molecular Operating Environment (MOE) (Chemical Computing Group Inc.). Initial identification of the binding sites was based on sphere sets obtained with the program SPHGEN within the DOCK package. For SPHGEN the solvent accessible surface was calculated with the program DMS using surface density of 2.76 vertex points per Å$^2$ and a probe radius of 1.4 Å. These sphere sets were subsequently used for database screening. A set of 1000 structurally diverse test compounds were then docked into each putative binding site (see following section) using DOCK4. The docked ligands were then used to calculate the binding response (BR) score, which is based on a combination of energetic and geometric criteria.

In Silico Database Screening.

A virtual database of more than 1.5 million low-molecular weight commercially available compounds was used for the virtual screening. The database has been created in our laboratory by converting files obtained from the vendors in the 2D SDF format to the 3D MOL2 format through a procedure that included addition of hydrogen, assignment of protonation state, geometry optimization with MMFF94 force field using the programs MOE (Chemical Computing Group Inc.), and assignment of atomic partial charges based on CM2 charge model at the semi-empirical quantum chemical AM 1 level using the program AMSOL. The compounds that were screened had 10 or fewer rotatable bonds and between 10 and 40 heavy atoms.

Database screening was performed using an in-house modified MPI version of the program DOCK4. During docking the protein structure was fixed with ligand flexibility treated using the anchored search method, with selected conformations eliminated based on energetic criteria, ensuring conformational diversity and energetically favorable conformations. Energy minimization was performed after building the entire molecule, with the ligand orientation with the most favorable interaction energy for all the protein conformations selected for each molecule. The GRID method implemented in DOCK was used to approximate the ligand-protein interaction energies during ligand placement as a sum of electrostatics and vdW energy components. The GRID box dimensions were 35.7 Å×35.9 Å×35.7 Å, centered on the sphere set to ensure that docked molecules were within the grid.

Scoring of compounds from the primary docking was performed using the vdW attractive interaction energy (IE) to evaluate the shape complementarity between ligands and the protein binding sites. Due to the contribution of the molecular size to the energy score, compound selection favoring higher molecular weight (MW) compounds, the vdW attractive IE was normalized based on the number of non-hydrogen atoms N raised to a power x. Normalization based on vdW attractive IE was performed with x=m/12, where m ranges from 0 to 12. The selected value of x for each screen was that corresponding to a median MW of the selected compounds closest to 300 daltons.

The top 50,000 compounds obtained from the primary database screen were subjected to a more rigorous and computationally demanding docking procedure, referred to as secondary docking. The procedure described for primary docking was followed with the additional step of simultaneous energy minimization of all rotatable bonds that connect anchor fragments during the stepwise building of the molecule. Receptor flexibility was taken into account by using all representative conformations of ERK2 obtained from the MD simulations. Each compound was docked individually to each conformation, from which one with the most favorable total interaction energy was chosen as the energy score of the compound. The total ligand-receptor IEs were then normalized and used to select the top 1000 compounds for each site. In the case of the FRS/5 site, compound scoring based on the normalized IE yielded a large number of charged compounds. Accordingly, the normalized vdW attractive energy was used for compound scoring and selection.

Final selection of compounds for experimental assay involved maximizing chemical and structural diversity of the compounds as well as considering their physicochemical properties with respect to bioavailability. The top 1,000 compounds identified in secondary database screening were subjected to chemical clustering. The Jarvis-Patrick algorithm implemented in MOE (Chemical Computing Group Inc.) was used to identify dissimilar clusters of compounds using the BIT-packed version of MACCS structural key (BIT-MACCS) fingerprints with the Tanimoto coefficient (TC) as the similarity index as previously described. Compounds for experimental assay were then manually selected from the clusters, with priority given to those compounds with drug-like properties with respect to bioavailability criteria as defined by Lipinski's rule of 5. It should be noted that a significant number of clusters only contained a single compound and only a small number of those compounds were selected for biological assays. Each search resulted in approximately 150 compounds selected for each site of which a subset was obtained for experimental assay. The purity of compounds shown to have biological activity was verified by mass spectrometry.

SILCS simulations to identify modifications of 2.3.2 with improved activity involved benzene and propane in aqueous solution, initiated from the holo conformation of ERK2 in complex with 2.3.2 obtained in the present study, with the ligand removed. 10 SILCS trajectories of 10 ns, initiated with different solvent box configurations overlaid on the protein, resulted in a cumulative sampling of 100 ns. The 3D probabilities of benzene and propane carbon atoms and water hydrogen and oxygen atoms were normalized with respect to the respective probabilities in solution and Boltzmann transformed to yield FragMaps in the grid free energy (GFE) representation, allowing for the calculation of ligand GFE (LGFE) values for the ligands. In order to obtain an estimate of the relative binding LGFE of modifications of 2.3.2, the following procedure was adopted. Starting from the ERK2-2.3.2 complex crystal conformation, using 2.3.2 orientation A, the structure was minimized with restraints on protein Cα atoms to remove bad contacts, using the steepest descent (SD) algorithm in CHARMM. Discovery Studio (Accelrys) was used to generate the structures of the analogs using 2.3.2 as the parent scaffold. The automated CGenFF program was used to generate the topology and parameters for the molecules in the context of the CHARMM General Force Field. To obtain the conformation of the analogs in complex with ERK2, each ligand was docked to the site by overlaying atoms common with 2.3.2 and was subject to 500 steps of SD minimization using CHARMM. To calculate the LGFE values each classified ligand atom was assigned a GFE value based on their 3D coordinates in the minimized conformation and their chemical type, which defines each atom as being in one of the four FragMap types. Only aromatic/aliphatic atoms closer than 5 Å and hydrogen bond donor/acceptor atoms closer than 2.5 Å to any protein atom in the minimized ligand conformation were used in the scoring scheme so as to capture direct interaction with the protein. The LGFE value for each ligand was the sum of GFEs over all classified atoms in each ligand. The relative LGFE values, ΔLGFE, of the analogs and 2.3.2 is thus expected to be indicative of their relative binding free energy with respect to the parent compound.

Table 1.

Residues on the ERK2 C-terminal domain known to impact substrate interactions. The residues are partitioned into the 5 individual sites considered in the present study.

TABLE 1

Binding Site Residues

1) Common docking (CD)/ED; DRS Thr157, Thr158, Asp316, Asp319
2) Leu114, Ser151, Trp190, Tyr191, Glu218, Asn222, Pro224
3) Ser221, Arg223, His237, Arg275
4) Ser244, Leu265, Pro266
5) F-recruitment site (FRS) Leu198, His230, Tyr231, Leu232, Leu235, Tyr261

Table 2.

Binding sites found in common to both 1ERK and 2ERK in at least one of their conformations tested. The average Binding Response (Avg. BR) score and the residues that form the sites are given. The maximum possible BR score is 1.0 and # of hits indicates the number of times each site was identified of the number of conformational analyzed.

TABLE 2

| Site # | ID # | Structure | Residues | # of hits | Avg. BR |
|---|---|---|---|---|---|
| 2 | A | 1ERK | GLU 69, HIS 145, ASP 165 | 8/10 | 0.95 |
|  | B | 1ERK | TYR 191, SER 151, GLU 218 | 10/10 | 0.89 |
|  | C | 1ERK | ASP 104, MET 106, ASP 109 | 10/10 | 0.96 |
| 3 | D | 1ERK | SER 221, ARG 223 | 7/10 | 0.92 |
|  | E | 1ERK | ILE 82, LEU 161 | 6/10 | 0.95 |
|  | F | 1ERK | LEU 119, MET 219, LEU 220 | 8/10 | 0.95 |
|  | G | 1ERK | SER 120, ASN 156 | 1/10 | 0.93 |
| 4 | H | 1ERK | SER 244, LEU 265, PRO 266 | 7/10 | 0.91 |
|  | I | 1ERK | GLY 243, LYS 270, ASP 289 | 7/10 | 0.95 |
| 2 | A | 2ERK | GLU 69, HIS 145, ASP 165 | 8/11 | 0.96 |
|  | B | 2ERK | TYR 191, SER 151, GLU 218 | 10/11 | 0.90 |
|  | C | 2ERK | ASP 104, MET 106, ASP 109 | 9/11 | 0.97 |
| 3 | D | 2ERK | SER 221, ARG 223 | 10/11 | 0.93 |
|  | E | 2ERK | ILE 82, LEU 161 | 6/11 | 0.92 |
|  | F | 2ERK | LEU 119, MET 219, LEU 220 | 3/11 | 0.81 |
|  | G | 2ERK | SER 120, ASN 156 | 6/11 | 0.93 |
| 4 | H | 2ERK | SER 244, LEU 265, PRO 266 | 7/11 | 0.93 |
|  | I | 2ERK | GLY 243, LYS 270, ASP 289 | 9/11 | 0.94 |

TABLE 3

Table 3. Binding sites found in the FRS docking site identified by the Binding Response (BR) calculation. Residues defining the sites are presented along with the BR score. The maximum possible BR score is 1.0

| Structures | ID# | Residues | BR score |
|---|---|---|---|
| 1ERK | c1 | L182, T183, E184, I196, M197, H230, Y231, L232 | 0.88 |
| 1ERK | c3 | L182, E184, Y231, L232 | 0.95 |
| 1ERK | c4 | L182, T183, E184, I196, M197, Y231, L232 | 0.85 |
| 1ERK | c5 | H230, L232, D233, N236, Y261, L265 | 0.83 |
| 1ERK | c6 | L182, T183, E184, H230, Y231, L232 | 0.78 |
| 2ERK | c1 | L198, Y231, L232, L235, N255, K257, A258, Y261 | 0.95 |
| 2ERK | c2 | M197, L198, S200, Y231, L232, L235, A258 | 0.94 |
| 2ERK | c3 | K257, Y261 | 0.84 |
| 2ERK | c4 | M197, L198, Y231, L232, L235, Y261 | 0.87 |
| 2ERK | c5 | I196, N199, S200, K201 | 0.89 |
| 2ERK | c6 | M197, L198, N199, S200, Y231, L235 | 0.74 |
| SILCS | c1 | H230, L232, D233, L235, N236, Y261, L265, P266 | 0.72 |

TABLE 3-continued

Table 3. Binding sites found in the FRS docking site identified by the Binding Response (BR) calculation. Residues defining the sites are presented along with the BR score. The maximum possible BR score is 1.0

| Structures | ID# | Residues | BR score |
|---|---|---|---|
| SILCS | c2 | H230, L232, D233, N236, L265, P266 | 0.84 |
| SILCS | c3 | K229, L232, D233, N236 | 0.86 |
| SILCS | c4 | H230, L232, D233, L235, N236, L239, Y261, L265 | 0.78 |
| SILCS | c5 | K229, L232, D233 | 0.91 |
| SILCS | c7 | L182, M197, L198, L235 | 0.86 |

TABLE 4

Table 4. Types of normalized energies and normalization factors used in two levels of database screening. VdWAE is the vdW attractive interaction energy and IE is the total interaction energy between ligand and protein, and N is number of non-hydrogen atoms in each ligand. Normalization factors used are shown in parentheses, and selected to have median MW closest to the target MW of 300 Da. In the case of sites 2, 3 and 4, the normalization was performed independently for the phosphorylated and unphosphorylated forms of ERK2.

| Target site | Primary screening | Secondary screening |
|---|---|---|
| Site2 (phosphorylated) | vdWAE/N^(1/2) | IE/N^(3/5) |
| Site2 (unphosphorylated) | vdWAE/N^(3/5) | IE/N^(3/5) |
| Site3 (phosphorylated) | vdWAE/N^(2/5) | IE/N^(3/5) |
| Site3 (unphosphorylated) | vdWAE/N^(1/2) | IE/N^(3/5) |
| Site4 (phosphorylated) | vdWAE/N^(3/5) | IE/N^(2/3) |
| Site4 (unphosphorylated) | vdWAE/N^(3/5) | IE/N^(2/3) |
| Site 5/FRS | vdWAE/N^(5/12) | vdWAE/N^(5/12) |

Crystal structure of the ERK2-2.3.2 complex (data not shown) shows the putative 2.3.2 binding site formed by the following 16 residues, as determined by those with one or more atoms within 4 Å of ligand in 2.3.2-ERK2 crystal structure: His178, Thr179, Gly180, Phe181, Leu182, Ile196, Met197, Leu198, Asn199, Ser200, Tyr203, Tyr231, Asn255, Lys257, Ala258, and Tyr261, 11 of which were also identified by the CADD binding site prediction (Table 3). Consistent with this, 2.3.2 has significant overlap with the putative binding site identified for the FRS based on the BR analysis; the sphere set corresponds to set c1 on 2ERK (Table 3). However, it should be noted that 2.3.2 was predicted to bind to site 2 in the database screen, indicating the fortuitous nature of the discovery of this inhibitor. While efforts were made to generate a range of protein conformations for screening, the local conformational change occurring upon binding of 2.3.2 was not sampled in the MD simulations such that the binding of 2.3.2 to its actual binding site was not observed. Thus, while the docking studies predicted 2.3.2 to interact in the region of site 2, the experimental studies showed it to bind the FRS, thereby supporting its ability to inhibit substrates containing the F-sites. Binding of 2.3.2 to ERK2 leads to significant changes in the conformation of the activation loop, although the overall structure of the protein is not significantly altered. Based on the estimated overall coordinate uncertainty in these crystal structures (Cruickshank DPI), the activation loop residues are expected to exhibit shifts in atomic positions that are ~0.4 Å. As indicated by percentile-based spread (p.b.s.). However, larger differences (0.95 Å) are observed between backbone atoms of active and inactive ERK2 (PDB entries 2ERK and 1ERK, respectively). Based on p.b.s., it appears as if the ERK2-2.3.2 complex is somewhat closer to both inactive (0.64 Å) and active ERK2 (0.67 Å). Inspection of the structural differences for individual residues reveals that most of the structural shifts are within expected range, while larger changes are observed for four stretches of the sequence that form a continuous epitope surrounding and including the activation loop. The data shows the superposition of the three structures and highlights the conformational change. The 2.3.2 binding site in inactive ERK2 is occupied by Phe181/Leu182; curiously, these residues shift away upon ERK2 activation as well, opening up the binding site. While conformations of the activation loop and surrounding region of the protein surface in active and 2.3.2-bound ERK2 are not exactly identical, there are significant general similarities in the conformational change upon 2.3.2 binding and upon activation. This suggests that the ligand may bind to the activated ERK2 in a similar but not identical fashion.

Example 3

CADD and biological testing to identify compounds that interact with novel ERK substrate docking sites. The known ERK2 docking sites include the DRS (site 1) and FRS (site 5) regions, whereas predicted docking sites are labeled sites 2-4 (Table 6). One compound, 76, that targets the DRS is being marketed by Calbiochem/EMD Biosciences (Cat#328006) as an ERK inhibitor. Successful inhibitor identification to date has been based on a combination of fluorescence quenching (FQ) of ERK2 wild type and docking site mutants in the presence of test compound. We currently have 14 mutations in ERK2 that cover residues in sites 1-5 (Table 6) and have used these mutants in FQ assays to evaluate regions that may be targeted by putative inhibitors identified by CADD (Table 7). This approach in combination with CADD predictions were able to identify 2 compounds that appear to target ERK2 on the putative substrate docking sites 2 (2.14) or 4 (4.57).

Tables 6 and 7

TABLE 1

ERK2 docking site mutations.

| Site | Mutation |
|---|---|
| 1 | T157A |
| | D319N |
| | T157A/D319N |
| 2 | L114A |
| | Y191A |
| | W190F |
| 3 | R275A |
| 4 | L265A |
| 5 | L198A |
| | L235A |
| | L232A |
| | L198A/L232A |
| | L198A/L235A |
| 1/5 | T157A/L189A/L235A |

TABLE 2

Binding affinity of select lead compounds to ERK2 wild type (WT) of ERK2 containing the indicated mutations at known (sites 1 and 5) or predicted (sites 2, 3, 4) amino acids involved in substrate interactions. Fluorescence quenching of ERK2 in the presence of 1 nM to 20 μM of test compound N = 3-4.

| $K_D$ (μM) compound | ERK2 WT | T157A | Site1 D319N | T157A/D319N |
|---|---|---|---|---|
| 76 | 5.0 ± 0.3 | 6.1 ± 0.6 | 7.0 ± 1.0 | 6.4 ± 0.3 |
| 76.2 | 3.3 ± 0.2 | 2.4 ± 0.4 | 1.9 ± 0.3 | 4.0 ± 0.6 |
| 76.3 | 1.5 ± 0.1 | 8.1 ± 0.8 | 13.4 ± 0.6 | >20 |
| 76.4 | 2.4 ± 0.9 | 3.0 ± 1.0 | 18.0 ± 2.0 | >20 |

| | | Site 2 | | Site 3 | Site 4 |
|---|---|---|---|---|---|
| compound | WT | L114A | Y191A | R275A | L265A |
| 2.14 | 1.13 ± 0.17 | >20 | >20 | 1.4 | 0.64 |
| 2.3.2 | 0.13 ± 0.02 | 0.027 ± 0.01 | 0.13 | 0.24 | 0.28 |
| 3.15 | 0.018 ± 0.006 | 0.016 ± 0.004 | 0.018 ± 0.003 | 0.042 ± 0.02 | 0.016 ± 0.002 |
| 4.57 | 0.60 ± 0.15 | 0.4 | 1.2 | 0.08 | >20 |

| | | | Site 5 | | |
|---|---|---|---|---|---|
| compound | WT | L232A | L235A | L198A/L232A | L198A/L235A |
| 2.14 | 1.13 ± 0.17 | ND | 0.92 | 1.25 | 0.45 |
| 2.3.2 | 0.13 ± 0.02 | 0.13 | 0.09 ± 0.02 | 0.14 ± 0.02 | >20 |
| 3.15 | 0.018 ± 0.006 | 0.048 ± 0.001 | 0.167 ± 0.020 | 0.014 ± 0.001 | >20 |
| 4.57 | 0.60 ± 0.15 | 0.67 | ND | 0.08 | 1.12 |

CADD studies supported by data in Table 7 (marked as Table 2) predict 76 analogs to bind a polar groove located within the ERK2 DRS, including residues D316/D319, and be involved in a cation-pi interaction between R133 and the phenyl ring of 76, both the primary amino and aromatic moieties will be considered for modification. Furthermore, the primary amine and the adjacent methylene group are likely sites of metabolism. Recent changes to the 4-ethoxyphenyl group of 76 and its alkenyl linkage to the thiazolidin-2,4-dione (TZD) core will also guide synthesis. These studies indicated the importance of the aromatic group, but only two modifications of the ethylamino group were done. Thus, the phenyl ring may be varied, and the ethylamino group functionalized, to investigate the significance of the TZD core as outlined in FIG. 9A.

Figure 9:
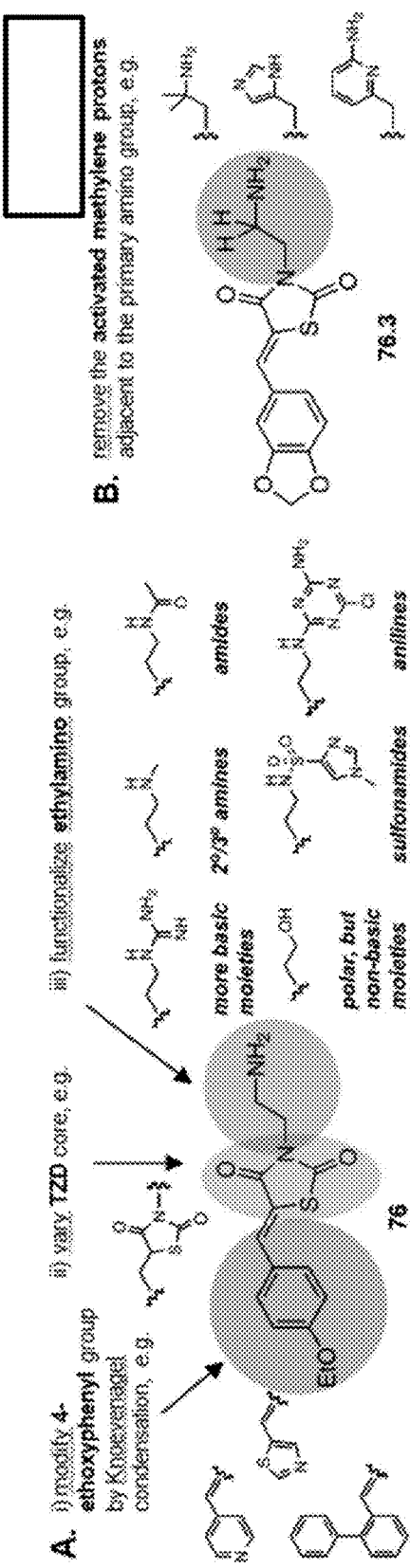
FIG. 9. Scheme for modifying the TZD compound.

The introduction of the 4-ethoxyphenyl group is achieved by a Knoevenagel condensation reaction between 4-ethoxybenzaldehyde and TZD, and can thus be readily varied. The primary amine can be functionalized furnishing secondary and tertiary amines, amides, sulfonamides and anilines. As the amino group may be involved in ionic interactions, several of the modifications will maintain and even enhance the basicity of the amine. Concerning metabolic stability (eg. towards mono-oxygenases, monoamine oxidases and P450 enzymes) the amine functionality will be replaced with basic (primary) aromatic amines. These have the advantage of having no α-hydrogens, thereby avoiding deamination. In addition, the α-hydrogens will be replaced with alkyl groups (FIG. 9B).

Applying the strategy outlined above, several analogs of 76 have been synthesized and tested, and we found that the pharmacophore of 76 is the TZD core with a short (C2 or C3) hydrocarbon chain linking the core imide-type nitrogen to a basic, primary amino group, while the other face of the TZD core requires a cis double bond linking the core to a para-alkoxy-substituted phenyl ring. Interestingly, replacement of the ethylamine moiety with non-basic benzylic and aniline groups improved potency and selectivity of compounds targeting site 1 on ERK2 (FIG. 10). We examined the effects of these compounds on proliferation of A375 melanoma cells with BRaf mutations that require ERK activation for survival. Notably more potent than the parent compound is SF-2-054, which has high nM affinity and selective inhibition of A375 cells (FIG. 10).

Combined CADD/experimental studies led to the identification of 2.3.2 (Table 7 above and Scheme 1 below), that interacts with ERK2 at sub μM binding affinity, $K_D$=0.13±0.02, 0.3 and 0.5 μM as determined by FQ (Table 2), SPR, and ITC, respectively. In cells, 2.3.2 preferentially inhibited ERK-mediated phosphorylation of the F-site containing substrate Elk-1 as compared to RSK-1, which interacts with ERK through a D-domain (FIG. 6A/B). In addition, 2.3.2 showed ~150 fold selectivity for ERK2 as compared to the structurally related p38α MAP kinase (FIG. 6). Consistent with the inhibition of Elk-1 phosphorylation was the lack of 2.3.2 (up to 20 μM) binding to ERK2 mutated at L198 and L235 (Table 2) and X-ray analysis showed 2.3.2 to bind to the FRS and directly interact with M197, L198, Y231, and Y261 (FIG. 7, PDB ID:3QYI), residues implicated in mediating ERK interactions with F-site containing substrates. Thus, 2.3.2 is the first molecule identified to interact with ERK2 in the region involved in interactions with F-site substrates and will be the initial target for CADD-direct optimization.

Shown in FIG. 11A is the 2.3.2-ERK2 crystal structure along with the SILCS 3D FragMaps (not to be confused with electron density). The overlap of the aliphatic and aromatic SILCS maps with the phenyl moiety of 2.3.2 is evident as is an aliphatic region adjacent to the sulfone ring. The presence of these maps along with the space around both the benzene and sulfone rings suggests that the addition of nonpolar moieties at both sites may improve affinity. To test this, four synthetically-accessible chemical modifications of the phenyl ring were identified (FIG. 11B) and the changes in the Ligand GFE for the modifications relative to 2.3.2 calculated (GFE values in FIG. 11B).

The methyl modification is predicted to be slightly unfavorable with the polar nitro moiety predicted to significantly decrease binding; both the biphenyl and napthyl moieties are predicted to improve activity. It should be noted that the LGFE calculations take only seconds to perform for each modification as they are based on precomputed SILCS GFEs particular addressing the issue of why the methyl group was predicted to lead to decreased binding based on the GFEs although qualitative analysis of the SILCS fragmaps (FIG. 11A) suggested that nonpolar moieties would improve binding.

Figure 11:
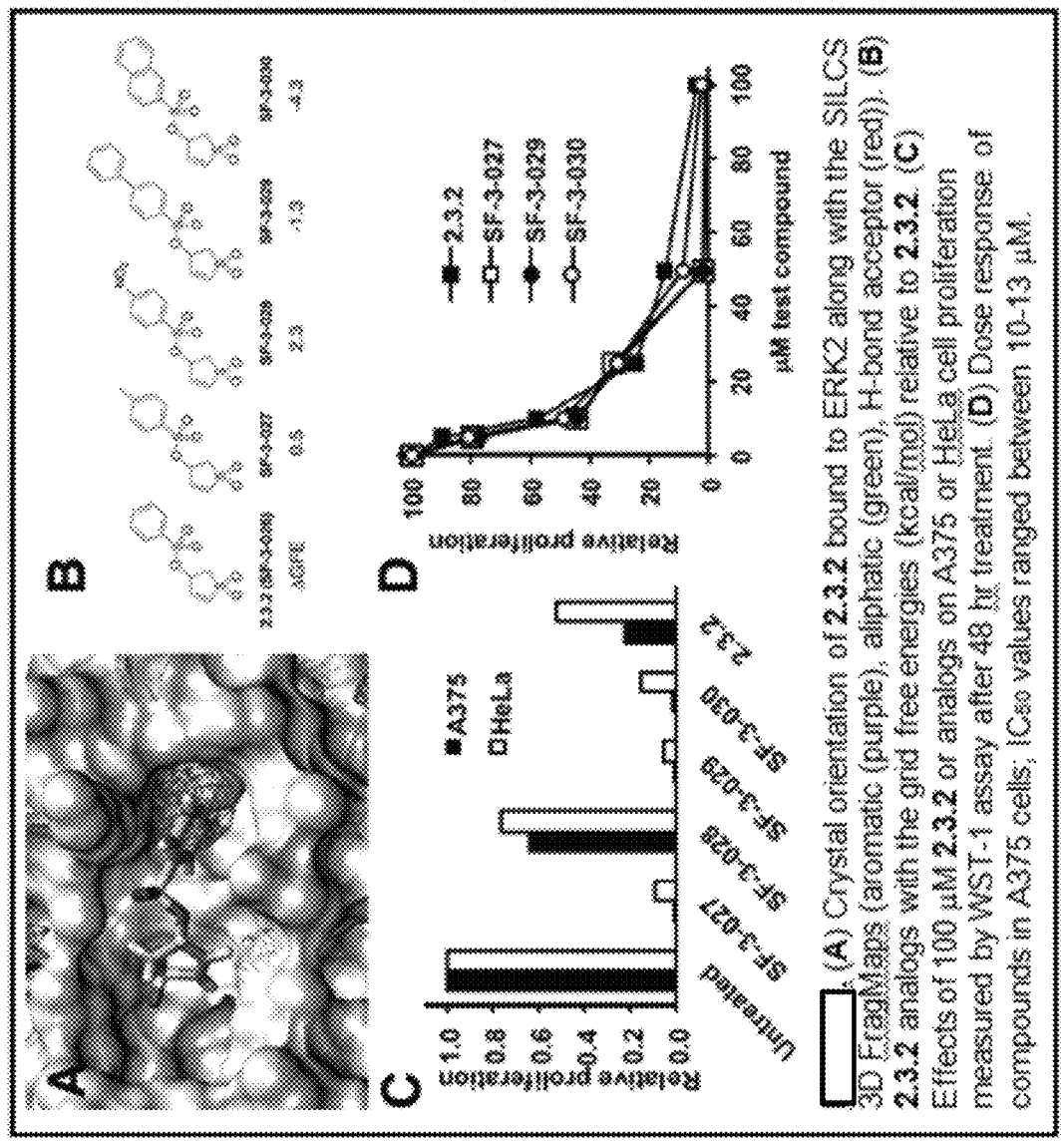
FIG. 11. Crystal orientation of 2.3.2. bound to ERK2 along with the SILCS 3D FragMap.

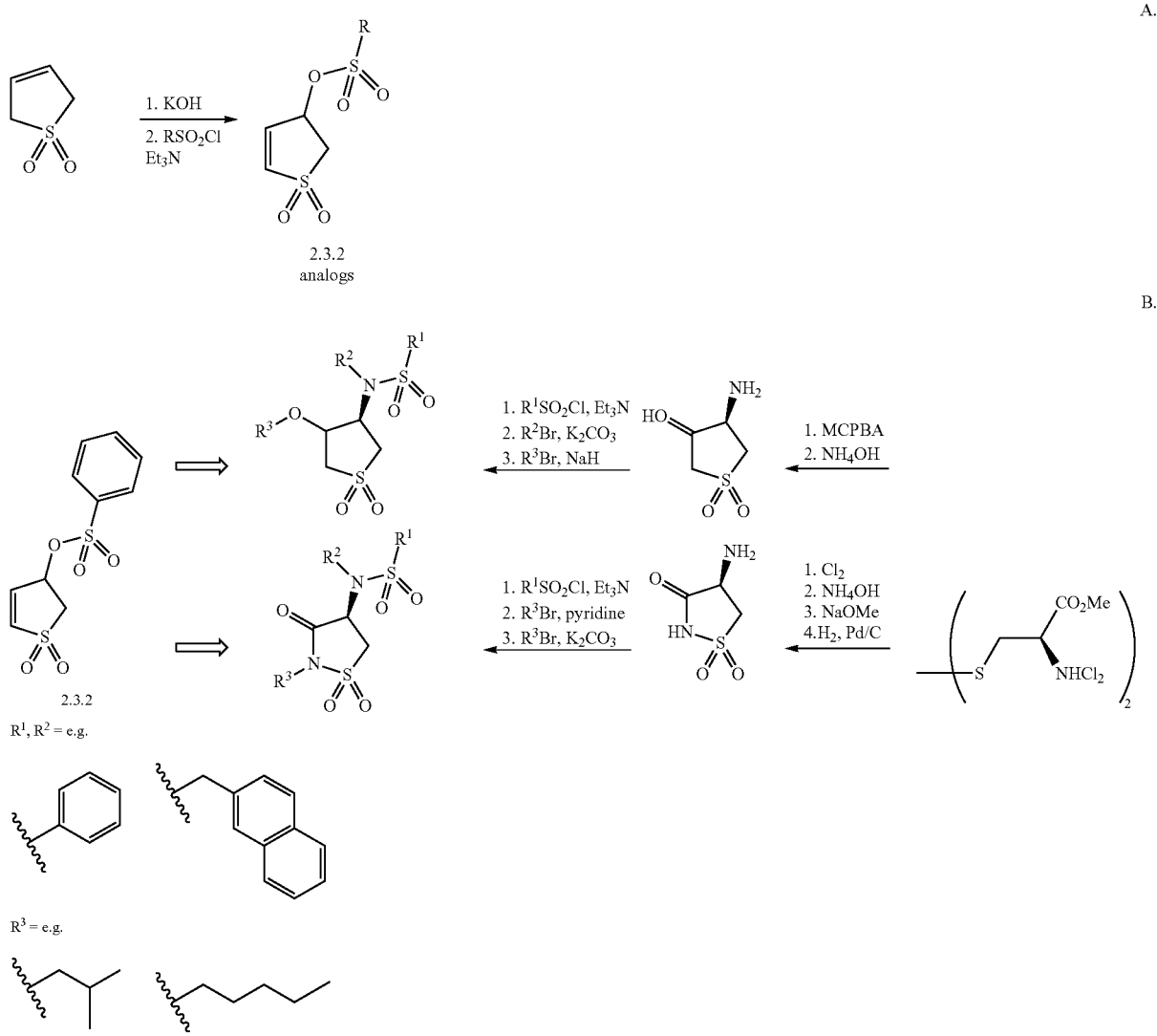

described above; inclusion of the nitro moiety was done in anticipation that it would make an unfavorable contribution to binding due to its polar nature. The analogs were then synthesized (Scheme 1A) and tested for inhibition of A375 and HeLa cell proliferation. All hydrophobic modifications inhibited A375 proliferation to a similar degree; however addition of a polar nitro group largely abolished the inhibitory effect (FIG. 11C/D). These data demonstrate that the CADD approach can predict modifications to improve activity. In the proposed study we will extend the SILCS methodology to include a wider range of chemical fragments to more rigorously inform the chemical optimization process. We will also continue our efforts in developing the SILCS methodology, in Ligand optimization via a CADD/medicinal chemistry approach to improve affinity will initially target 2.3.2 using the crystal structure in combination with the SILCS methodology. SILCS can direct ligand design qualitatively based on visual inspection of the FragMaps (FIG. 11A) as well as quantitatively using GFE that are based on conversion of SILCS 3D probability distributions to free energies based on a Boltzmann distribution. It should be emphasized that the GFE scores represent true free energies in the Gibbs ensemble that take into account desolvation and protein flexibility, a significant improvement over current database screening scoring methods. As discussed above (FIG. 11A), the SILCS 3D maps suggested modifications to 2.3.2 that were shown to improve binding. Another issue that will be addressed is the potential for 2.3.2 to operate as an alkylating agent by: (1) Michael addition to the conjugated C=C double bond and (2) substitution of the leaving group PhSO$_2$O$^-$ either directly (S$_N$2) or indirectly (S$_N$2') by initial attack at the C=C functionality. To limit these potentials we propose in Scheme 1B to (a) reduce the C=C double bond so that this functionality can no longer participate in reactions, and (b) replace the oxygen atom connecting the PhSO$_2$ group to the 2,3-dihydrothiophene moiety with NH or NR groups, converting the labile PhSO$_2$O group into non-labile PhSO$_2$NH or PhSO$_2$NR$^2$ groups. The chemistry for the upper class of molecules is routine, for the lower class there are reported procedures to access the cyclic N-acyl sulfonamide. As shown above (FIG. 11) more hydrophobic groups at the R$^1$ and R$^2$ positions in 2.3.2 enhance binding; additional analogs will pursue this avenue of modification. Concerning R$^3$, analysis of the SILCS maps (FIG. 11A) indicate that aliphatic substitutions at this position will improve activity; GFE scores of the O-methyl, O-ethyl and O-propyl substitutions versus 2.3.2 were 0.3, −1.4 and −2.2 kcal/mol, respectively, predicting that the larger aliphatic groups will lead to enhanced activity. This strategy combining CADD and synthetic considerations combined with experimental assays will be used to drive ligand design for 2.3.2 as well as other compounds when crystal structures of those ligands become available.

Figure 12:
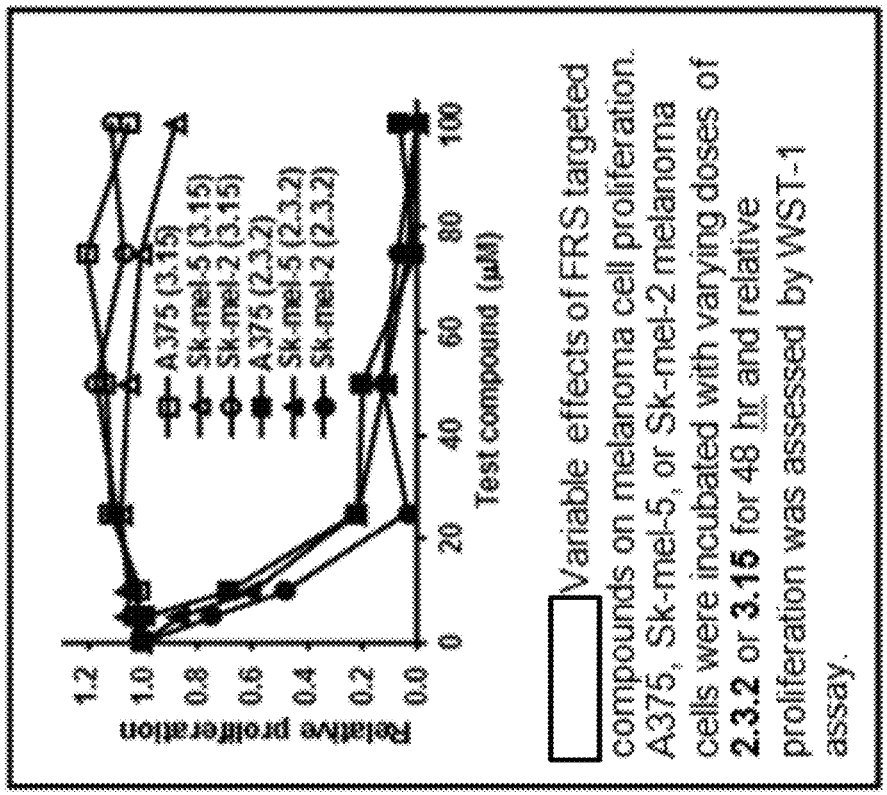
FIG. 12. Variable effects of FRS targeted compounds on melanoma cell proliferation.

Substrate profiling using ERK2 pull down and quantitative MS analysis is used to assess proteins that are differentially regulated by DRS or FRS targeted compounds. As shown in FIG. 12, FRS targeted compounds 2.3.2 have surprisingly variable effects on proliferation of melanoma cell lines. These findings reinforce the concept that inhibitors may be developed to differentiate between distinct FRS targeted substrates.

Figure 13:
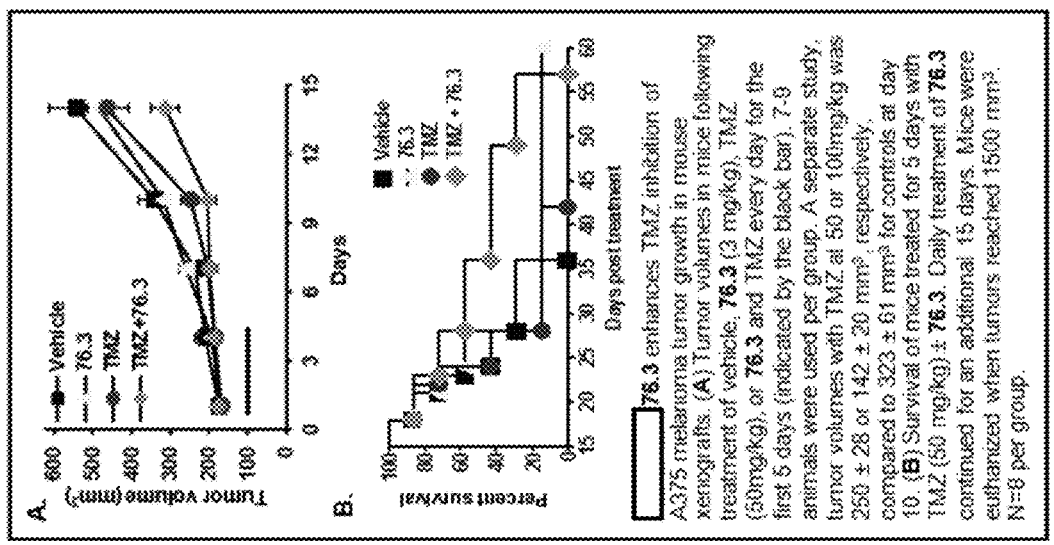
FIG. 13. 76.3 enhances TMZ inhibition of A375 melanoma growth in mouse xenographs.

We have tested the DRS compound 76.3, which showed selective ERK interactions but, as a single agent, had little effect on A375 cell proliferation. However, in combination with temozolomide (TMZ), an anti-cancer drug being tested in combination with targeted agents to treat melanoma, 76.3 enhanced TMZ reduction of A375 tumor growth in immune-compromised nu/nu mice (FIG. 13A). Moreover, 76.3 and TMZ also appeared to delay tumor growth in mice harboring A375 tumors indicative of prolonged survival (FIG. 13B). Importantly, no overt toxicity or weight loss was observed in the treated mice as compared to controls in these studies (data not shown) or in previously described in vivo studies testing our ERK-targeted compounds. These findings and the cell-based studies demonstrate that compounds targeting ERK substrate docking sites may be useful tools to enhance the efficacy of anti-cancer drugs relevant to cancers with active ERK signaling.

Example 4

We have successfully used computer-aided drug design (CADD) to search for low-molecular-weight docking domain inhibitors of ERK. One of the compounds, identified as 76, binds ERK2 with a K$_d$ value of 5 μM and blocks phosphorylation of the downstream ERK targets RSK-1 and Elk-1. Moreover, 76 inhibited growth of HeLa cervical carcinoma and A549 lung carcinoma cells as assessed by colony formation assay in a dose dependent manner with IC$_{50}$ values of ~20 μM. The structure of compound 76 is shown below:

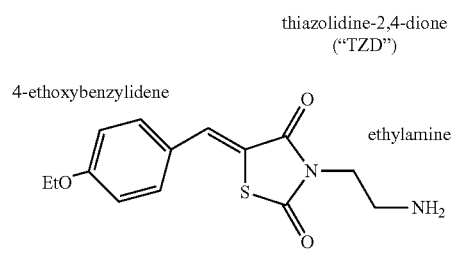

Compound 76 was selected targeting a polar cleft within the D-recruitment site (DRS), which facilitates ERK interactions with substrates containing D domains (also referred to as the DEJL motif or Docking site for ERK or JNK, LXL). The DRS consists of aspartate residues that form the common docking (CD) and threonine residues in ED docking sites. It was predicted that the primary amino group of 76 is engaged in salt bridge interactions with Asp316 and Asp319 of the CD site and was within 5-7 Å of Thr157 and Thr158 of the ED site. In addition, commercially available analogues of 76 obtained from a structure-based similarity search showed activity in preliminary experiments (not shown) indicating the compound to be a suitable lead for additional optimization. To determine the pharmacophore of 76, which would help direct future optimization efforts, we embarked on a structure-activity relationship (SAR) study. Comprised of three distinct fragments—a 4-ethoxybenzylidene group, a thiazolidine-2,4-dione ("TZD") core and an ethylamine tail—compound 76 can be synthesized in just three linear steps (Scheme 1). Briefly, a Knoevenagel condensation of thiazolidine-2,4-dione (1) with 4-ethoxybenzaldehyde afforded benzylidene 2. Alkylation of the acidic imide NH of 2 was next accomplished via Mitsunobu conditions with N-trityl-ethanolamine to give 3, which, upon brief treatment with TFA, furnished the compound 76.

Scheme 2:

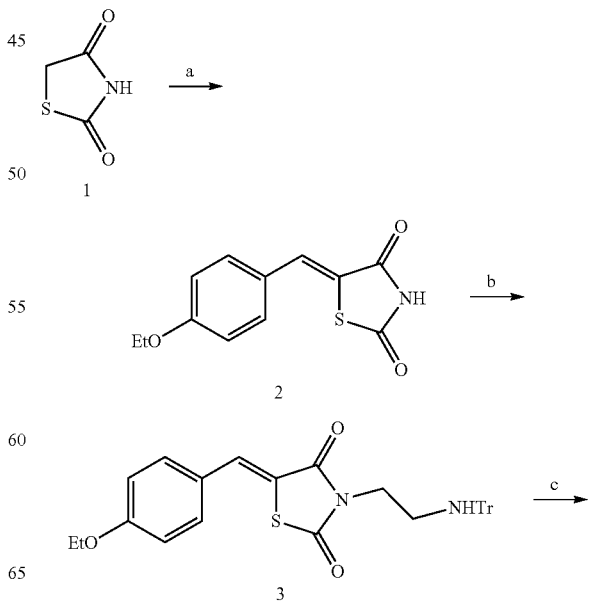

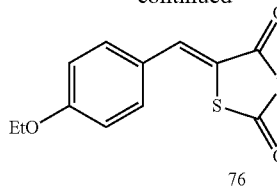

76

(a) 4-ethoxybenzaldehyde, cat. piperidine, EtOH, reflux, 16 h, 77%; (b) HOCH₂CH₂NHTr, PPh3, DIAD, THF, rt, 16 h, 75%; (c) TFA—CH₂Cl₂, 1:1, rt, 30 min, 99%.

In a recent SAR analysis of the 4-ethoxyphenyl moiety of 76, it was found that shifting the 4-ethoxy group to the 2-position of the phenyl ring led to increased inhibition of human leukemia U937 cell proliferation. In a subsequent study, removal of the 4-ethoxy group and extension of the benzylidene moiety to a 3-phenylpropylidene moiety furnished a dual inhibitor of the Raf/MEK/ERK and PI3K/Akt signaling pathways. In the present work, a cell-based SAR analysis of 76 focused on the thiazolidine-2,4-dione component and ethylamine moiety, in which cancer cells with activated ERK signaling were employed. Additionally, further novel analogs that explored the SAR of the 4-ethoxyphenyl group were also prepared, directly complementing the aforementioned studies.

Thiazolidine-2,4-dione ("TZD") SAR.

In order to determine the contribution of the TZD portion of 76 to the inhibition of ERK, we prepared all of the TZD analogues depicted in Scheme 3. First, to examine its role, the benzylidene C=C double bond of 76 was chemoselectively reduced with LiBH₄ as shown in Scheme 3A to deliver compound 4, the imide nitrogen of which was alkylated with N-Boc-2-bromethylamine to give 5, and then TFA-mediated removal of the Boc group furnished target molecule 6. In order to generate the rhodanine analogue (9) of 76, the chemistry carried out was the same as that set forth in Scheme 2, substituting 2,4-thiazolidinedione (1) for rhodanine (7). For the cyclic imide derivative 13, reaction of maleimide (10) with triphenylphosphine (PPh₃) afforded the stabilized phosphorane 11, which underwent a Wittig reaction with 4-ethoxybenzaldehyde to furnish benzylidene 12. N-Alkylation of 12 with N-Boc-2-bromoethylamine, and subsequent removal of the Boc group gave the imide-functionalized product 13. Acetylation of pyrrolidin-2-one (14), followed by a modified Knoevenagel condensation reaction with 4-ethoxybenzaldehyde yielded benzylidene 16. In this case, the amide NH of 16 was insufficiently acidic to undergo the Mitsunobu reaction with N-trityl-ethanolamine (5); instead, N-trityl-ethanolamine was first activated as its 0-mesylate and then conjugated to the amide anion of 16. Deprotection of the Tr group by treatment with TFA afforded the target molecule 17. Finally, to investigate the importance of the cyclic nature of the 2,4-thiazolidinedione ring of 76, we constructed the acyclic analog 20. Once more, a Knoevenagel condensation played a key role in the synthesis, conjugating malonic acid (18) to 4-ethoxybenzaldehye to furnish the cinnaminic acid derivative 19, which was then coupled to N-Boc-ethylenediamine and subsequently deprotected to give acrylamide derivative 20.

Scheme 3:

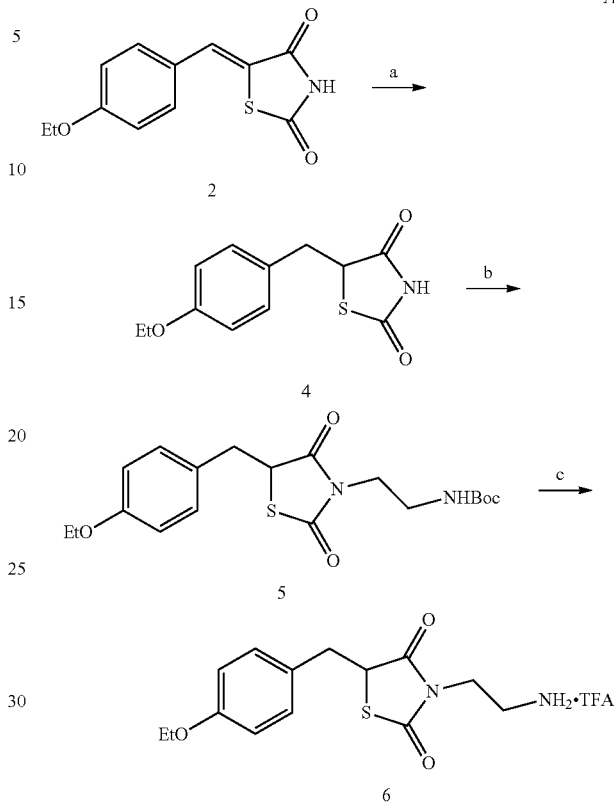

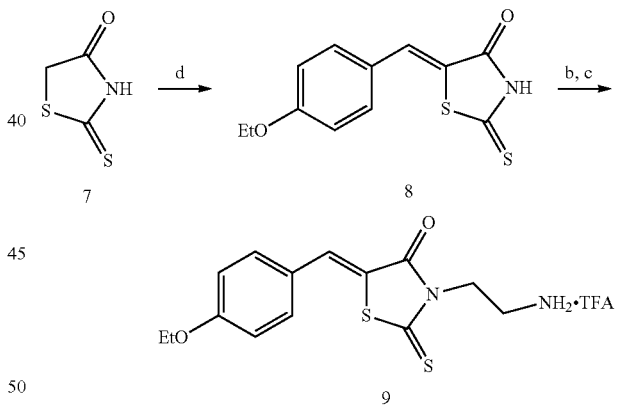

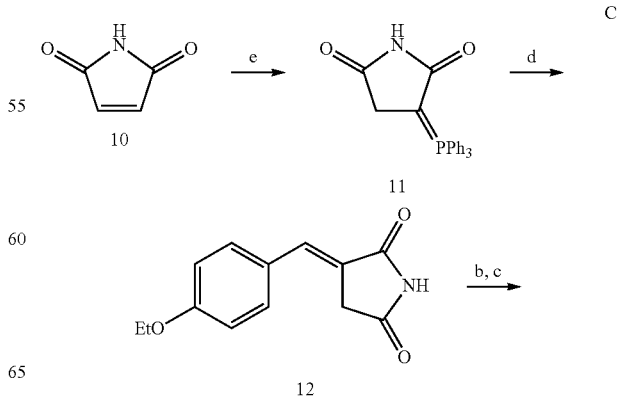

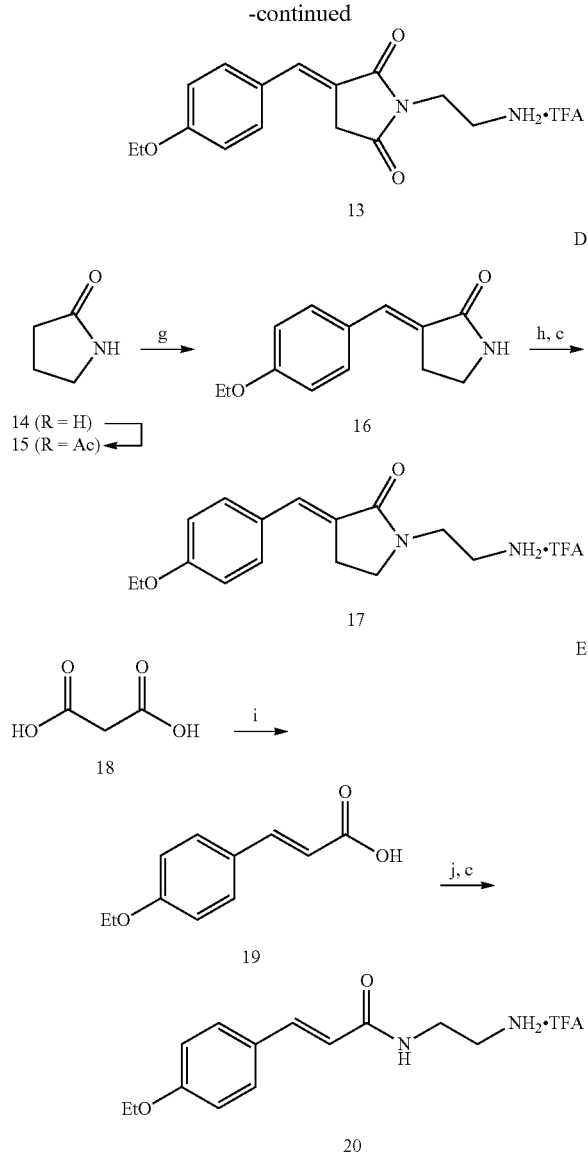

(a) LiBH₄, THF-pyridine, 80° C., 12 h, 77%;
(b) BrCH₂CH₂NHBoc, K₂CO₃, DMF, rt, 16 h, 43-53%;
(c) TFA/CH₂Cl₂, 1:1, rt, 1 h, 43-99%;
(d) 4-ethoxybenzaldehyde, cat. piperidine, EtOH, reflux, 1-16 h, 77-93%;
(e) PPh₃, acetone, reflux, 1 h, 83%;
(f) Ac₂O, THF, reflux, 2 h, 77%;
(g) 4-ethoxybenzaldehyde, NaOᵗBu, 0° C., THF, 1 h, 45%;
(h) MsOCH₂CH₂NHTr, NaH, rt, DMF, 16 h, 58%;
(i) 4-ethoxybenzaldehyde, piperidine, pyridine, 120° C., 4 h, 99%;
(j) BOcNHCH₂CH₂NH₂, HBTU, DIPEA, DMF, rt, 3 h, 99%.

Ethylamine SAR.

The ethylamine group of 76 was modulated to a variety of alternative groups; these can be divided into three categories: alkylamino substitutions, N-functionalized ethylamino substitutions, which may be further sub-divided into basic and non-basic substitutions, and, finally, alkyl and benzylic substitutions. For the alkylamino substitutions, which were designed to investigate the optimal spacer between the thiazolidinedione ring and the basic amino group, as well as the identity of the basic group, benzylidene 2 was prepared as earlier described. The imide NH of 2 was next alkylated via classical conditions or the Mitsunobu reaction with the appropriate bromide or alcohol, respectively, to afford N-Boc or N-Tr intermediates 21, as shown in Scheme 3, which were then deprotected under acidic conditions to deliver the final products 22 as their TFA salts. For the basic N-functionalized ethylamino substitutions, 76 was converted to secondary amines 23a-e either through mono-reductive amination conditions or de novo syntheses, and tertiary amines 24a-c through one-pot double-reductive aminations (Scheme 4). In the course of our work, we discovered that the neutral N-Boc-protected derivative of 76 exhibited some activity in the cellular assays. Presumably, this molecule exhibits a different binding mode to the parent compound that carries a basic, primary amine. Nonetheless, we elected to investigate further substitutions of this ethylamino group that included additional non-basic derivatives. Compound 76 was thus subjected to a variety of acylations, alkoxycarbonylations and sulfonylations to furnish the corresponding amides (25a-d), carbamates (26a-e) and sulfonamides (27a-c), respectively, according to standard techniques outlined in Scheme 4. Finally, for the non-amino-based alkyl and benzylic substitutions, the imide NH of 3 was functionalized using classical conditions with K₂CO₃ and the appropriate alkyl or benzylic bromide or chloride at room temperature, 60° C. or 100° C., depending on the reactivity of the halide, to afford compounds 28a-s (Scheme 6).

Scheme 4.

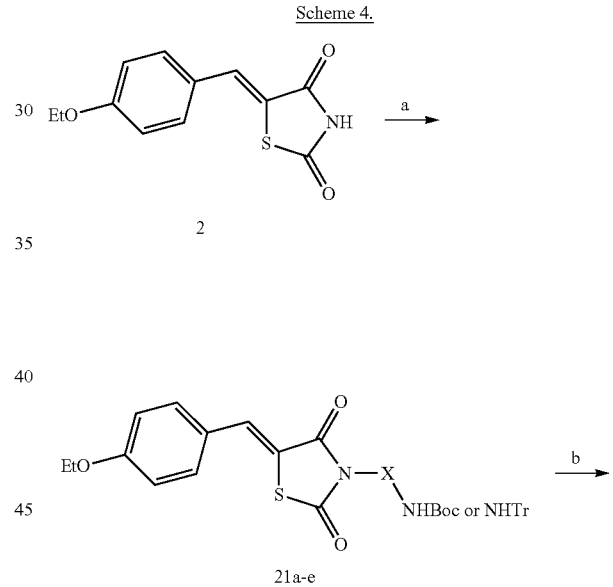

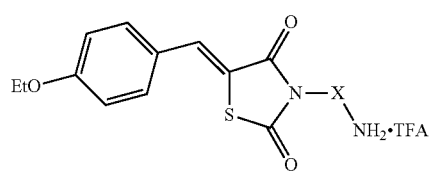 [SMILES: CCOc1ccc(/C=C2\CC(=O)N(CCN)C2=O)cc1]

(a) Br—X—NHBoc, K₂CO₃, DMF, rt, 3 h, 16-79% or HO—X—NHTr, PPh₃, DIAD, THF, 45° C., 16 h, 99%; TFA—CH₂Cl₂, 1:1, rt, 1 h, 36-97%.

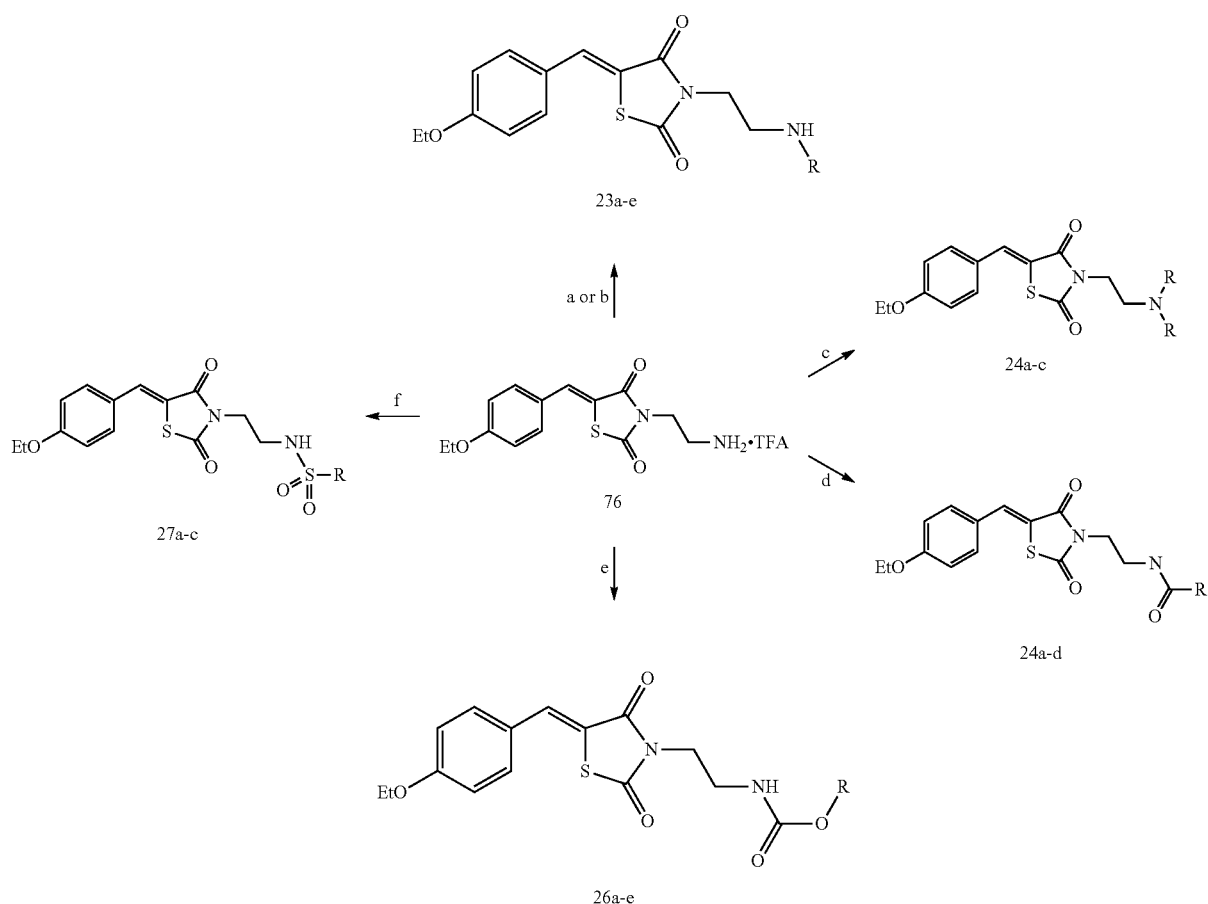

(a) R²CHO, NaBH(OAc)₃, CH₂ClCH₂Cl, rt, 16 h, 38-69%;
(b) 1. HOCH₂CH₂N(R)Tr, PPh₃, DIAD, THF, rt, 16 h; 2. TFA—CH₂Cl₂, rt, 30 min, 28-37% (two steps);
(c) excess R²CHO, NaBH(OAc)₃, CH₂ClCH₂Cl, rt, 16 h, 69-93%;
(d) (RCO)2O, CH₂Cl₂, DIPEA, rt, 16 h, 81-92% or 4-cyanobenzoic acid, HBTU, DIPEA, DMF, rt, 16 h, 92%
(e) ROCOCl, DIPEA, CH₂Cl₂, rt, 16 h, 96-98%
(f) RSO₂Cl, DIPEA, CH₂Cl₂, rt, 16 h, 92-98%;

4-Ethoxyphenyl SAR.

Variation of the 4-ethoxyphenyl component of 76 was accomplished with ease via the chemistry described in Scheme 5. After a Mitsunobu reaction of 1 with N-trityl-ethanolamine, resulting compound 29 was subjected to Konevenagel condensations with a variety of aldehydes, and then subsequently deprotected under acidic conditions to furnish the final molecules 30a-l.

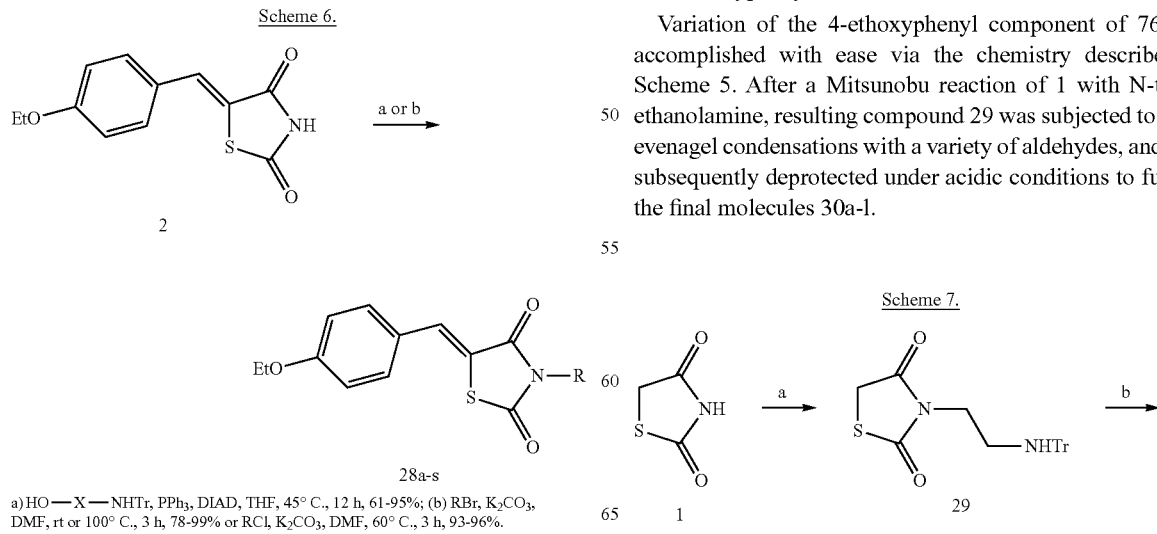

a) HO—X—NHTr, PPh₃, DIAD, THF, 45° C., 12 h, 61-95%; (b) RBr, K₂CO₃, DMF, rt or 100° C., 3 h, 78-99% or RCl, K₂CO₃, DMF, 60° C., 3 h, 93-96%.

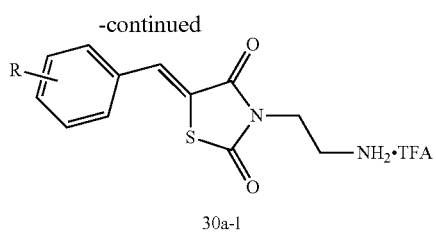

30a-1

(a) HOCH$_2$CH$_2$NHTr, PPh$_3$, DIAD, THF, rt, 16 h, 75%; (b) 1. R'CHO, cat. piperidine, EtOH, reflux, 16 h; 2. RBr or RI, K$_2$CO$_3$, DMF, 70° C., 12 h; 3. TFA—CH$_2$Cl$_2$, 1:1, rt, 30 min, 20-73% (two or three steps).

Biology.

For initial phenotypic screening, we evaluated the activity of 76 analogues on proliferation of A375 and SK-MEL-28 melanoma cell lines, which have constitutively active ERK1/2 due to a homozygous mutation in BRaf that drives proliferation and survival. In addition, compounds were tested in RPMI-7951 cells, which also contain mutated BRaf and are resistant to BRaf inhibitors due to the overexpression of MAP3K8 (the gene encoding COT/Tp12) that provides an alternative mechanism to indirectly or directly activate ERK proteins. We also studied the compounds' effects on HL-60 leukemic cells that are p53 defective and have an activating mutation in N-Ras, and, therefore, also demonstrate upregulation of ERK1/2. For comparison, HeLa cervical carcinoma and Jurkat T-cell leukemia cells, which are p53 defective cancer cell lines but contain no known activating mutations in the ERK pathway, were studied. All compounds were initially tested at 100 µM for their abilities to inhibit cell proliferation, and data are presented as a percentage of the vehicle-treated control (100%). Table 1 shows the cell data for analogues of 76 in which the TZD core was varied. As compared to the parent compound 76, which showed selective inhibition of melanoma cells, reduction of the benzylidene double bond (compound 6) led to almost complete loss of growth inhibition activity in all cell lines, indicating this double bond plays either a structural role to maintain 76 in a β-strand-like structure and/or is functionally significant as a Michael acceptor. That is, the biological activity of 76 may derive, in part, from its ability to act as an irreversible inhibitor through covalent alkylation of amino acid side chains, particularly cysteines, on the surface of the ERK1/2 proteins. The isosteric replacement of the 2-carbonyl oxygen with a sulfur atom (compound 9) resulted both in a reduction of inhibitory activity and a reduction in selectivity for melanoma cells. The endocyclic sulfur appears to be important, since its replacement with an isosteric methylene group (compound 13) resulted in a less potent and selective inhibitor of cells containing BRaf or N-Ras mutations compared to the parent compound 76, indicating the sulfur atom may function as a hydrogen bond acceptor. Removal of the carbonyl group of 13 that is juxtaposed to the endocyclic sulfur in 76 resulted in compound 17 that was almost completely bereft of inhibitory activity (Table 1). Furthermore, deletion of the two endocyclic methylene groups of 17 afforded the non-cyclic compound 20, which exhibited little inhibition of any of the cells. Taken together, these data confirm the importance of the benzylidene double bond and the TZD core towards effective inhibition of cell lines harboring constitutive ERK activation.

TABLE 8

| Cell proliferation SAR of thiazolidine-2,5-dione (TZD) ring of 76. | | | | | | | |
|---|---|---|---|---|---|---|---|
| Compound Number | Structure | Cell Viability (% of Vehicle) | | | | | |
| | | SK-MEL-28 | A375 | RPMI-7951 | HL-60 | HeLa | Jurkat |
| 76 | | 11 ± 7 | 2.1 ± 2 | 0.3 ± 0.02 | 4.4 ± 1 | 53 ± 3 | 59 ± 5 |
| 6 | | 88 ± 3 | 92 ± 6 | 70 ± 5 | 41 ± 17 | 90 ± 4 | 108 ± 10 |
| 9 | | 45 ± 7 | 21 ± 10 | 3.3 ± 2 | 7.9 ± 3 | 26 ± 6 | 52 ± 4 |
| 13 | | 65 ± 4 | 29 ± 3 | 19 ± 5 | 58 ± 28 | 75 ± 2 | 100 ± 10 |

TABLE 8-continued

Cell proliferation SAR of thiazolidine-2,5-dione (TZD) ring of 76.

| Compound Number | Structure | Cell Viability (% of Vehicle) | | | | | |
|---|---|---|---|---|---|---|---|
| | | SK-MEL-28 | A375 | RPMI-7951 | HL-60 | HeLa | Jurkat |
| 17 | (EtO-phenyl-CH= pyrrolidinone N-CH2CH2NH2) | 79 ± 6 | 95 ± 2 | 96 ± 3 | 73 ± 9 | 89 ± 4 | 92 ± 2 |
| 20 | (EtO-phenyl-CH=CH-C(O)-NH-CH2CH2NH2) | 83 ± 4 | 81 ± 5 | 93 ± 9 | 59 ± 25 | 94 ± 5 | 89 ± 7 |

Excepting the longer 3-propylamine derivative 22a, modification of the ethyl portion of the ethylamine tail of 76 led to either a reduction in activity and/or selectivity against melanoma cells (compare data for 76 with that for 22a-e). Alkylation of the primary amino group of 76 to afford secondary amines resulted in a drop in inhibitory activity with small groups (e.g. methyl, 23a) that could be recovered with bulkier groups (e.g. isobutyl, 23c; phenyl, 23d). However selective inhibition of cell lines containing activating BRaf or N-Ras mutations was largely lost. These findings reveal the significance of the primary amino group of 76, suggesting it may engage in multiple hydrogen bonds. The corresponding tertiary amines 24a-c exhibited no inhibition of any of the cell lines. Similarly, little inhibition of cell proliferation was observed upon replacement of the ethylamine group ($pK_a$~10) with the less basic imidazole derivative 28a ($pK_a$~7) or the 2-aminopyridine derivative 28b ($pK_a$~6), the latter of which could be envisaged to engage in hydrogen-bonded chelates with Asp316 or Asp319 through its tautomeric pyridin-2(1H)-imine. However, growth inhibitory activity was observed with the considerably more basic ($pK_a$~12) guanidine derivative 28c, although there was no apparent selectivity for the melanoma cells over HL-60, HeLa or Jurkat cells. A finely-tuned basic group, therefore, is required at the terminus of the ethyl group of 76 to confer both potency and selectivity against cells with constitutive ERK activation.

TABLE 9

Cell proliferation SAR of basic replacements of ethylamine tail of 76.

| Compound Number | R | Cell Viability (% of Vehicle) | | | | | |
|---|---|---|---|---|---|---|---|
| | | SK-MEL-28 | A375 | RPMI-7951 | HL-60 | HeLa | Jurkat |
| 76 | -CH2CH2NH2 | 11 ± 7 | 2.1 ± 2 | 0.3 ± 0.02 | 4.4 ± 1 | 53 ± 3 | 59 ± 5 |
| 22a | -CH2CH2CH2NH2 | 0.5 ± 0.01 | 0.7 ± 0.1 | 0.6 ± 0.1 | 8.0 ± 72 | 12 ± 2 | 9.0 ± 2 |
| 22b | -CH2CH(CH3)NH2 | 32 ± 4 | 25 ± 4 | 16 ± 1 | 7.3 ± 3 | 49 ± 7 | 58 ± 10 |
| 22c | -CH(CH3)CH2NH2 | 28 ± 4 | 13 ± 2 | 22 ± 3 | 8.1 ± 3 | 45 ± 7 | 54 ± 10 |

TABLE 9-continued

Cell proliferation SAR of basic replacements of ethylamine tail of 76.

| Compound Number | R | Cell Viability (% of Vehicle), | | | | | |
|---|---|---|---|---|---|---|---|
| | | SK-MEL-28 | A375 | RPMI-7951 | HL-60 | HeLa | Jurkat |
| 22d | –CH(CO₂Me)CH₂–NH₂ | 33 ± 9 | 41 ± 11 | 1.8 ± 0.1 | 25 ± 5 | 87 ± 4 | 100 ± 5 |
| 22e | –CH(CH₂NH₂)₂ | 32 ± 2 | 19 ± 4 | 25 ± 3 | 11 ± 4 | 62 ± 2 | 81 ± 9 |
| 23a | –(CH₂)₂NHMe | 91 ± 1 | 95 ± 2 | 54 ± 7 | 17 ± 11 | 85 ± 4 | 83 ± 6 |
| 23b | –(CH₂)₂NHEt | 63 ± 10 | 51 ± 4 | 60 ± 4 | 14 ± 4 | 81 ± 2 | 69 ± 10 |
| 23c | –(CH₂)₂NH-iBu | 1.3 ± 0.1 | 1.0 ± 0.1 | 1.0 ± 0.1 | 10 ± 4 | 3.7 ± 0.4 | 2.5 ± 0.1 |
| 23d | –(CH₂)₂NHCH₂Ph | 25 ± 6 | 13 ± 1 | 2.5 ± 0.3 | 5.0 ± 2 | 37 ± 1 | 89 ± 4 |
| 23e | –(CH₂)₂NHCH₂(4-CN-C₆H₄) | 96 ± 6 | 89 ± 3 | 96 ± 5 | 75 ± 25 | 88 ± 2 | 98 ± 5 |
| 24a | –(CH₂)₂NMe₂ | 101 ± 0.3 | 115 ± 2 | 130 ± 4 | 110 ± 14 | 90 ± 5 | 95 ± 1 |
| 24b | –(CH₂)₂N(CH₂Ph)₂ | 104 ± 4 | 122 ± 7 | 120 ± 3 | 109 ± 24 | 92 ± 9 | 104 ± 2 |

TABLE 9-continued

Cell proliferation SAR of basic replacements of ethylamine tail of 76.

| Compound Number | R | Cell Viability (% of Vehicle) | | | | | |
|---|---|---|---|---|---|---|---|
| | | SK-MEL-28 | A375 | RPMI-7951 | HL-60 | HeLa | Jurkat |
| 24c | NC-benzyl-N-benzyl-CN | 107 ± 3 | 115 ± 1 | 108 ± 9 | 108 ± 16 | 97 ± 8 | 100 ± 2 |
| 28a | imidazole | 74 ± 6 | 101 ± 2 | 70 ± 2 | 123 ± 20 | 80 ± 4 | 106 ± 6 |
| 28b | 2-aminopyridine | 86 ± 3 | 111 ± 1 | 101 ± 4 | 107 ± 26 | 87 ± 6 | 105 ± 5 |
| 28c | guanidine | 55 ± 6 | 31 ± 4 | 42 ± 6 | 20 ± 6 | 17 ± 2 | 6.5 ± 0.5 |

In general, data in Table 10 demonstrate that blockade of the amino group of 76 as neutral amides, carbamates and sulfonamides (25a-27c) afforded compounds with little to no inhibitory activity, underscoring the importance of the basic character of the primary amino group of 76, which is consistent with binding acidic residues, such as Asp316 and Asp319, in salt bridge interactions, as originally proposed. An exception is the Fmoc derivative 26e, which demonstrated selective inhibition of melanoma cells.

TABLE 10

Cell proliferation SAR of N-functionalization of ethylamine tail of 76.

| Compound Number | R | Cell Viability (% of Vehicle) | | | | | |
|---|---|---|---|---|---|---|---|
| | | SK-MEL-28 | A375 | RPMI-7951 | HL-60 | HeLa | Jurkat |
| 25a | acetyl | 105 ± 2 | 121 ± 4 | 124 ± 5 | 106 ± 23 | 100 ± 11 | 105 ± 8 |

TABLE 10-continued

Cell proliferation SAR of N-functionalization of ethylamine tail of 76.

| Compound Number | R | Cell Viability (% of Vehicle) | | | | | |
|---|---|---|---|---|---|---|---|
| | | SK-MEL-28 | A375 | RPMI-7951 | HL-60 | HeLa | Jurkat |
| 25b | -C(O)CF$_3$ | 105 ± 2 | 118 ± 4 | 127 ± 3 | 101 ± 23 | 98 ± 11 | 103 ± 6 |
| 25c | -C(O)C(CH$_3$)$_3$ | 73 ± 1 | 84 ± 2 | 62 ± 7 | 31 ± 5 | 81 ± 1 | 92 ± 7 |
| 25d | -C(O)-C$_6$H$_4$-CN | 103 ± 2 | 118 ± 3 | 122 ± 10 | 101 ± 12 | 99 ± 9 | 102 ± 7 |
| 26a | -C(O)OCH$_3$ | 88 ± 3 | 96 ± 4 | 102 ± 4 | 104 ± 31 | 84 ± 4 | 97 ± 7 |
| 26b | -C(O)OC(CH$_3$)$_3$ | 83 ± 5 | 88 ± 3 | 67 ± 4 | 95 ± 21 | 88 ± 5 | 111 ± 9 |
| 26c | -C(O)OCH$_2$CH(CH$_3$)$_2$ | 94 ± 1 | 102 ± 4 | 75 ± 12 | 80 ± 28 | 95 ± 3 | 110 ± 4 |
| 26d | -C(O)OCH$_2$C$_6$H$_5$ | 97 ± 1 | 103 ± 3 | 54 ± 6 | 85 ± 27 | 98 ± 6 | 112 ± 5 |
| 26e | -C(O)O-Fmoc | 29 ± 7 | 43 ± 3 | 27 ± 3 | 103 ± 13 | 85 ± 4 | 139 ± 14 |
| 27a | -S(O)$_2$CH$_3$ | 87 ± 2 | 94 ± 2 | 68 ± 3 | 82 ± 44 | 82 ± 1 | 85 ± 3 |

TABLE 10-continued

Cell proliferation SAR of N-functionalization of ethylamine tail of 76.

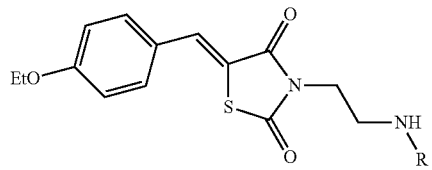

| Compound Number | R | Cell Viability (% of Vehicle) | | | | | |
|---|---|---|---|---|---|---|---|
| | | SK-MEL-28 | A375 | RPMI-7951 | HL-60 | HeLa | Jurkat |
| 27b | (sulfonyl-phenyl-CN) | 95 ± 3 | 109 ± 6 | 99 ± 4 | 101 ± 52 | 90 ± 4 | 103 ± 3 |
| 27c | (sulfonyl-N-methylimidazole) | 92 ± 5 | 107 ± 2 | 118 ± 6 | 51 ± 31 | 91 ± 5 | 97 ± 4 |

As shown in Table 11, removal of (3) and replacement of the ethylamine moiety with non-basic groups (28d-s) for the most part eliminated selectivity and potency in inhibiting melanoma cell proliferation, reinforcing the significance of this component of compound 76 that was established above (Tables 9 and 10). Particularly noteworthy is that the isosteric replacements of the primary amino group with methyl (28d), hydroxyl (28e) and chloro (28f) indicated that a polar and basic group is required at the terminus of the ethyl chain. In sharp contrast, para-substituted benzoic acid derivative 28q proved highly selective for inhibiting A375 cells but not the other melanoma cell lines with mutated BRaf suggesting this compound may have other cellular targets. Furthermore, we discovered that the location of the carboxylic acid function of 28q was significant, as evidenced by the meta (28r) and ortho (28s) isomers, which had reduced inhibition of and selectivity towards A375 cells. Given its lack of basic character, 28q may also target a different binding site than the compound 76.

TABLE 11

Cell proliferation SAR of non-basic ethylamine replacements of 76.

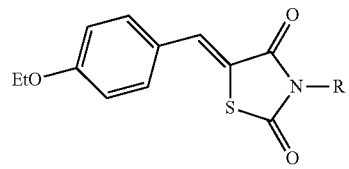

| Compound Number | R | Cell Viability (% of Vehicle) | | | | | |
|---|---|---|---|---|---|---|---|
| | | SK-MEL-28 | A375 | RPMI-7951 | HL-60 | HeLa | Jurkat |
| 2 | H | 103 ± 1 | 110 ± 10 | 144 ± 2 | 103 ± 16 | 98 ± 13 | 104 ± 4 |
| 28d | propyl | 101 ± 3 | 119 ± 5 | 116 ± 10 | 80 ± 26 | 96 ± 4 | 101 ± 5 |
| 28e | CH₂CH₂OH | 91 ± 1 | 116 ± 4 | 137 ± 8 | 91 ± 19 | 91 ± 2 | 101 ± 4 |

TABLE 11-continued
Cell proliferation SAR of non-basic ethylamine replacements of 76.
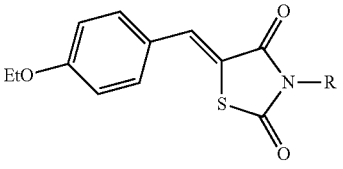
| Compound Number | R | Cell Viability (% of Vehicle) | | | | | |
|---|---|---|---|---|---|---|---|
| | | SK-MEL-28 | A375 | RPMI-7951 | HL-60 | HeLa | Jurkat |
| 28f | 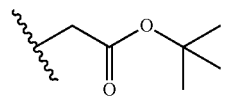 [SMILES: *CC(=O)OC(C)(C)C] | 97 ± 3 | 113 ± 9 | 128 ± 3 | 99 ± 14 | 87 ± 4 | 99 ± 5 |
| 28g | 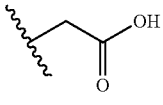 [SMILES: *CC(=O)O] | 101 ± 2 | 117 ± 7 | 110 ± 3 | 95 ± 18 | 88 ± 7 | 108 ± 3 |
| 28h | 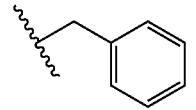 [SMILES: *Cc1ccccc1] | 106 ± 1 | 122 ± 6 | 133 ± 9 | 97 ± 27 | 104 ± 3 | 108 ± 3 |
| 28i | 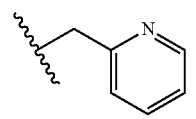 [SMILES: *Cc1ccccn1] | 90 ± 3 | 110 ± 4 | 114 ± 20 | 65 ± 1 | 95 ± 4 | 105 ± 4 |
| 28j | 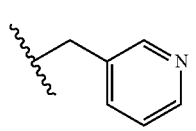 | 95 ± 3 | 124 ± 6 | 114 ± 5 | 89 ± 31 | 89 ± 5 | 101 ± 7 |
| 28k | 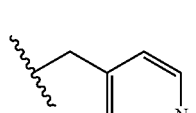 | 79 ± 4 | 105 ± 4 | 102 ± 2 | 65 ± 12 | 80 ± 2 | 98 ± 2 |
| 28l | 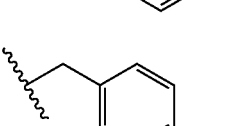 | 79 ± 3 | 105 ± 12 | 102 ± 3 | 82 ± 54 | 81 ± 5 | 96 ± 11 |
| 28m | 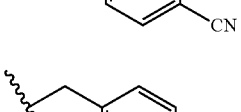 | 97 ± 7 | 108 ± 3 | 106 ± 8 | 86 ± 37 | 95 ± 3 | 103 ± 11 |
| 28n | 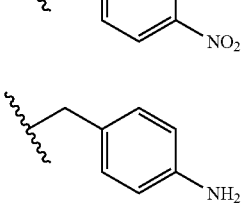 | 104 ± 3 | 117 ± 3 | 119 ± 13 | 97 ± 23 | 97 ± 9 | 101 ± 9 |
| 28o | | 94 ± 5 | 119 ± 6 | 102 ± 23 | 86 ± 21 | 89 ± 9 | 97 ± 7 |

TABLE 11-continued

Cell proliferation SAR of non-basic ethylamine replacements of 76.

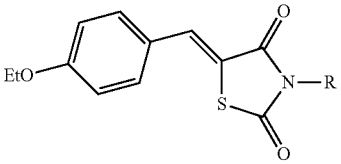

| Compound Number | R | Cell Viability (% of Vehicle) | | | | | |
|---|---|---|---|---|---|---|---|
| | | SK-MEL-28 | A375 | RPMI-7951 | HL-60 | HeLa | Jurkat |
| 28p | 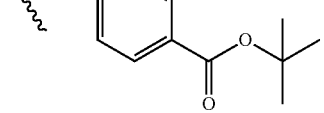 | 105 ± 3 | 119 ± 1 | 122 ± 1 | 98 ± 24 | 100 ± 6 | 101 ± 2 |
| 28q | 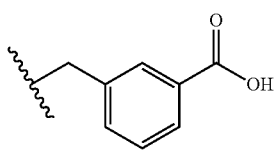 [SMILES: *Cc1cccc(C(=O)O)c1] | 59 ± 13 | 2.0 ± 0.5 | 34 ± 3 | 84 ± 37 | 64 ± 2 | 85 ± 3 |
| 28r | 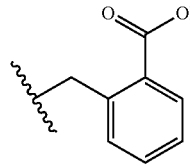 | 83 ± 7 | 59 ± 1 | 83 ± 6 | 41 ± 22 | 75 ± 4 | 80 ± 3 |
| 28s | | 49 ± 8 | 39 ± 1 | 45 ± 8 | 31 ± 15 | 61 ± 4 | 46 ± 1 |

Some of the greatest variation in inhibitory potency and selectivity was seen upon changes in the 4-ethoxyphenyl group of 76 (Table 12). First, the importance of the 4-ethoxy moiety was established by synthesizing and testing unsubstituted compound 30a, which showed some inhibition only in the HL-60 cell line. Moreover, the location of the ethoxy group proved significant, since shifting it from the para (compound 76) to the meta or ortho positions (compounds 30b and 30c, respectively) resulted in reduced growth inhibition and selectivity for melanoma cells with activating mutations in the ERK pathway, although inhibition of HL-60 cells was maintained. Comparison of the data for the para-substituted isosteres 30d and 30f reveal that a polar group at this position is preferred to deliver both potency and, particularly, selectivity for inhibiting melanoma and HL-60 cells. This is supported by comparing the data for the isosteres 76 and 30e, wherein the latter, although a potent inhibitor of the melanoma cell proliferation, exhibits 10 fold less selectivity for HL-60 cells, which must be attributed to the replacement of the para-oxygen with a para-methylene group. The addition of further hydrophobicity to the para-hydroxyl of 30f also generated potent and selective inhibitors with para-benzyloxy and para-isobutoxy derivatives 30g and 30h, respectively, completely inhibiting proliferation of melanoma and HL-60 cells and demonstrating excellent selectivity over HeLa and Jurkat cell lines. Given that Li et al. had discovered substitution at the ortho position of the phenyl ring of 76 resulted in compounds with potent activity against the proliferation of human leukemia U937 cells, we prepared the focused set of ortho-functionalized congeners 30j-l. Indeed, this led to a series of highly cytotoxic compounds. However, at the same time, selectivity at 100 μM for the ERK-dependent melanoma cell lines appeared to be lost. These data indicate that the pharmacophore of 76 requires a 4-alkoxyphenyl group connected to a TZD ring by virtue of a cis-double bond, along with an ethyl linker connecting a primary amine to the imide nitrogen of the TZD ring. Whilst the endocyclic sulfur appears to be important, the cis-double bond is not. Functionalization of the primary amino group of 76 was detrimental to its biological activity, suggesting its basicity and capacity to engage in several hydrogen bonding interactions are important for inhibitory activity.

TABLE 12
Cell proliferation SAR of 4-ethoxyphenyl moiety of 76.
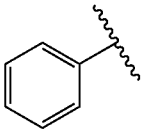 [SMILES: *c1ccccc1]
| Compound Number | R | Cell Viability (% of Vehicle) | | | | | |
|---|---|---|---|---|---|---|---|
| | | SK-MEL-28 | A375 | RPMI-7951 | HL-60 | HeLa | Jurkat |
| 30a | 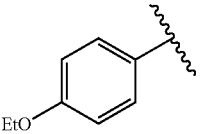 [SMILES: *c1ccc(OCC)cc1] | 88 ± 7 | 82 ± 9 | 89 ± 17 | 28 ± 20 | 82 ± 10 | 88 ± 4 |
| 76 | 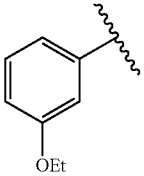 [SMILES: *c1cccc(OCC)c1] | 11 ± 7 | 2.1 ± 2 | 0.3 ± 0.02 | 4.4 ± 1 | 53 ± 3 | 59 ± 5 |
| 30b | 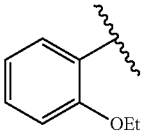 [SMILES: *c1ccccc1OCC] | 36 ± 6 | 19 ± 3 | 30 ± 2 | 4.8 ± 2 | 40 ± 1 | 54 ± 5 |
| 30c | 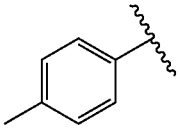 [SMILES: *c1ccc(C)cc1] | 52 ± 11 | 22 ± 9 | 45 ± 2 | 8.9 ± 4 | 39 ± 3 | 66 ± 5 |
| 30d | 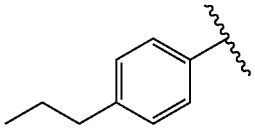 [SMILES: *c1ccc(CCC)cc1] | 31 ± 7 | 23 ± 6 | 23 ± 1 | 4.8 ± 2 | 54 ± 3 | 71 ± 6 |
| 30e | 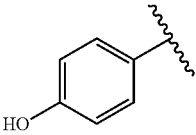 [SMILES: *c1ccc(O)cc1] | 0.6 ± 0.4 | 0.6 ± 0.1 | 0.7 ± 0.1 | 5.9 ± 2 | 11 ± 2 | 16 ± 8 |
| 30f | 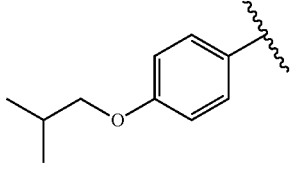 [SMILES: *c1ccc(OCC(C)C)cc1] | 38 ± 3 | 8.8 ± 2 | 24 ± 5 | 17 ± 12 | 63 ± 10 | 96 ± 3 |
| 30g | | 0.8 ± 0.2 | 1.8 ± 0.5 | 0.3 ± 0.04 | 5.0 ± 2 | 48 ± 3 | 91 ± 8 |

TABLE 12-continued

Cell proliferation SAR of 4-ethoxyphenyl moiety of 76.

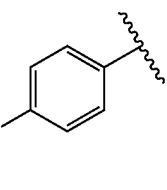

| Compound Number | R | Cell Viability (% of Vehicle) | | | | | |
|---|---|---|---|---|---|---|---|
| | | SK-MEL-28 | A375 | RPMI-7951 | HL-60 | HeLa | Jurkat |
| 30h | 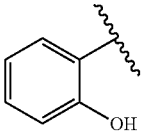 [SMILES: *c1ccccc1O] | 1.0 ± 1 | 0.6 ± 0.4 | 0.2 ± 0.04 | 5.2 ± 2 | 59 ± 3 | 87 ± 5 |
| 30i | 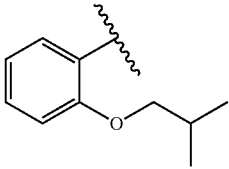 [SMILES: *c1ccccc1OCC(C)C] | 85 ± 9 | 78 ± 3 | 102 ± 10 | 24 ± 8 | 68 ± 3 | 99 ± 5 |
| 30j | 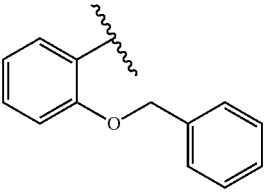 [SMILES: *c1ccccc1OCc1ccccc1] | 1.0 ± 0.1 | 0.8 ± 0.02 | 1.0 ± 0.04 | 9.5 ± 3.4 | 0.8 ± 0.1 | 1.8 ± 0.1 |
| 30k | 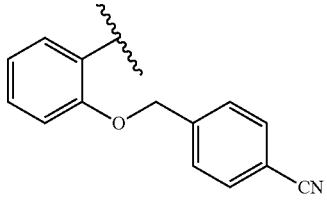 [SMILES: *c1ccccc1OCc1ccc(C#N)cc1] | 0.6 ± 0.04 | 0.6 ± 0.03 | 0.9 ± 0.1 | 8.3 ± 3.4 | 0.6 ± 0.1 | 1.5 ± 0.1 |
| 30l |  | 0.5 ± 0.01 | 0.5 ± 0.04 | 0.6 ± 0.03 | 5.7 ± 2 | 8.0 ± 2 | 6.7 ± 1 |

Figure 14:
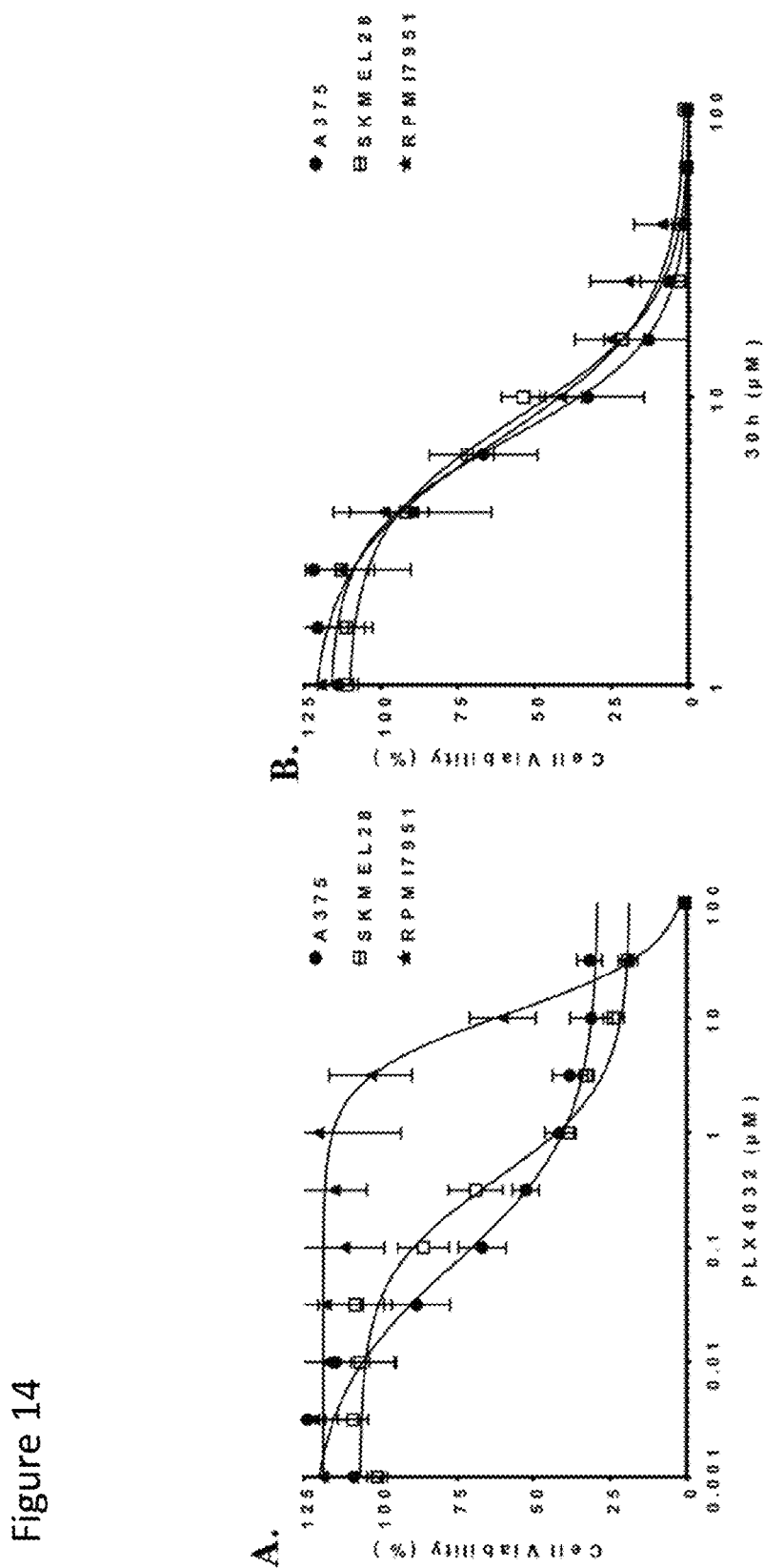
FIG. 14. Melanoma cell growth inhibition dose response curves for PLX4032 and compound 30h.

The initial screening of compounds suggested several new compounds that were selective inhibitors of cancer cell lines with activated ERK signaling. To further examine the effects of potential compounds, we performed dose-response assays to determine $GI_{50}$ values on a select number of compounds that showed selectivity for inhibiting proliferation of cells with activated ERK signaling. An example of the dose response curve for compound 30h and the BRaf inhibitor PLX4032 for inhibiting the growth of melanoma cell lines is shown in FIG. 14. Importantly, these data demonstrate that 30h is equally effective at inhibiting melanoma cells that have become resistant to PLX4032 as it is against PLX4032-sensitive cells. A summary of $GI_{50}$ values for select compounds along with comparisons to know ERK pathway inhibitors in various cell lines is shown in Table 13. These data highlight several key points of these structure activity relationship studies. First, thiazolidinedione compounds have been identified to be selective inhibitors of cancer cell lines containing activated ERK signaling. Second, changes in the 4-ethoxyphenyl component of the parent compound 76 improve selectivity and potency for inhibiting melanoma cell growth. Third, compound 30h is a potent inhibitor of melanoma cell lines that have become resistant to the clinically relevant BRaf and MEK inhibitors. As shown in Table 13, 30h is about three times as potent as the MEK inhibitor, AZD6244, in preventing growth of the drug-resistant RPMI7951 melanoma cell line. Lastly, 30h is as potent as the ATP-competitive pyrazolopyridazinamine ERK inhibitor (FR180204) in preventing melanoma cell proliferation and provides an alternative non-ATP-dependent approach to target cancer cells that are dependent on active ERK signaling.

FIG. 14 shows melanoma cell growth inhibition dose response curves for PLX4032 and compound 30h. Melanoma cells (A375, SK-MEL-28, and RPMI7951) were seeded at a density of 5,000 per well in 96-well plate. After overnight incubation, cells were treated with varying doses of PLX4032 (A) or 31h (B) for two days. Cell viability was determined by the addition of Cell Titer-Blue Reagent (20 μL/well) followed by 2 hours of incubation at 37° C. after which fluorescence was recorded (555/585 nm). Cell viability was expressed as percentage of vehicle control and data represent the average of three individual experiments.

TABLE 13

GI$_{50}$ values (μM) of select compounds.

| Compound | A375 | SK-MEL-28 | RPMI7951 | HeLa | Jurkat |
|---|---|---|---|---|---|
| 76 | 29 | 34 | 46 | >100 | >100 |
| 22a | 24 | 46 | 17 | ND | ND |
| 30g | 22 | 36 | 11 | ~100 | >100 |
| 30h | 7.0 | 9.0 | 7.0 | >100 | >100 |
| PLX4032 | 0.07 | 0.38 | 11 | >10 | >10 |
| AZD6244 | 0.03 | 0.17 | 20 | >10 | >10 |
| FR180204 | 5.0 | 4.0 | 11 | >10 | >10 |

ND = not determined.

To further demonstrate that the test compounds were targeting the ERK signaling pathway, we examined the activity of the activator protein-1 (AP-1) promoter and the serum response element (SRE), which are regulated by the ERK substrates c-Fos and Elk-1, respectively. Compounds 76 and 30g were both potent inhibitors of AP-1 and SRE promoter activity with estimated IC$_{50}$ values around 5 μM or less (FIG. 3A/B). Interestingly, 30h also inhibited ERK-mediated AP-1 and SRE promoter activity but was less potent than compounds 76 and 30g at lower concentrations. This suggests differences in how these compounds inhibit ERK signaling functions, which is further supported by the selective inhibition of the SRE promoter activity by compound 22a (FIG. 3B).

Conclusions.

The current study provides a comprehensive structure-function analysis of thiazolidinedione based compounds and their ability to inhibit the proliferation of cancer cells containing activated ERK signaling. These compounds support the utility of developing novel thiazolidinedione compounds that have been recognized to have potential applications for treating cancers such as melanoma. We have identified several chemical features on compounds such as 30h that promote selective and potent inhibition of cancer cells lines containing active ERK signaling as a result of BRaf or N-Ras mutations. Essential for activity is a TZD core, the imide nitrogen of which should be functionalized with an ethyl moiety terminating in a primary amino group. Furthermore, the acidic methylene of the TZD must be linked to a para-alkoxy-substituted phenyl ring through a cis-double bond. Given that other transformed cell lines are not affected by the compounds, our findings suggests that their mechanism of action involves inhibition of ERK signaling and not general toxicity. Moreover, these compounds are potent inhibitors of ERK-regulated transcription and further support ERK as the molecular target. Of particular importance is the ability for several compounds to inhibit melanoma cell lines that have become resistant to clinically relevant BRaf inhibitors. Recent studies support the use of ERK-targeted compounds to overcome alternative signaling pathways that contribute to drug resistance. Future studies will be important to provide a more comprehensive biological characterization of the compounds identified in these studies and the ERK substrates they affect.

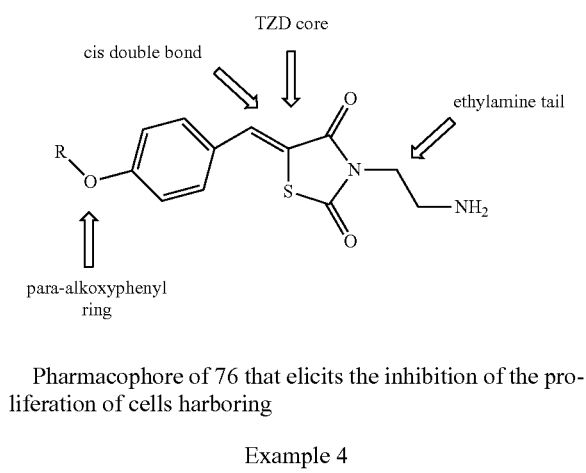

31

Pharmacophore of 76 that elicits the inhibition of the proliferation of cells harboring Example 4

General

Unless otherwise stated, all reactions were performed under an inert (N$_2$) atmosphere. Reagents and solvents were reagent grade and purchased from Sigma-Aldrich, Alfa Aesar, Oakwood and TCI America. $^1$H and $^{13}$C NMR spectra were recorded on Varian INOVA 400 MHz and Varian INOVA 500 MHz NMR spectrometers at 25° C. Chemical shifts are reported in parts per million (ppm). The residual solvent peak was used as an internal reference. The mass spectra were obtained on an Electrospray TOF (ESI-TOF) mass spectrometer (Bruker amaZon X). Prior to biological testing, final compounds were determined to be >95% pure by HPLC chromatography using a Waters 1525 fitted with a C18 reversed-phase column (length mm×4.6 mm, 5 m, 100 Å) according to the following conditions with solvents (A) H$_2$O/ 0.1% TFA, (B) CH$_3$CN/H$_2$O, 9:1 with 0.1% TFA, (C) H$_2$O, (D) CH$_3$CN/H$_2$O, 9:1, (E) H$_2$O/0.1% NH$_4$OH, (F) CH$_3$CN/ H$_2$O, 9:1 with 0.1% NH$_4$OH at 1 ml/min: (I) a gradient of 75% A to 100% B over 32 min, Atlantis); (II) a gradient of 50% A to 100% B over 22 min, Symmetry); (III) a gradient of 75% A to 100% B over 62 min, Atlantis); (IV) a gradient of 100% A to 100% B over 30 min, Atlantis; (V) a gradient of 75% A to 100% B over 52 min, Atlantis; (VI) a gradient of 50% A to 100% B over 30 min, Atlantis; (VII) a gradient of 100% A to 100% B over 52 min, Atlantis; (VIII) a gradient of 50% A to 100% B over 52 min, Atlantis; (IX) a gradient of 100% A to 100% B over 22 min, Symmetry; (X) a gradient of 50% C to 100% D, X-Bridge; (XI) a gradient of 100% E to 100% F over 22 min, X-Bridge; (XII) a gradient of 25% E to 100% F over 22 min, X-Bridge; (XIII) an isocratic gradient of 100% F for 5 min followed by a gradient of 100% E to 100% F over 22 min, X-Bridge.

(Z)-5-(4-ethoxybenzylidene)thiazolidine-2,4-dione
(2)

4-Ethoxybenzaldehyde (2.78 mL, 20.0 mmol) and 2,4-thiazolidinedione 1 (3.75 g, 32.0 mmol) were dissolved in 80 mL of anhydrous ethanol at room temperature and piperidine (0.60 mL, 6.0 mmol) was added to the reaction flask. The reaction mixture was stirred at 75° C. for 1 day and then allowed to cool down to room temperature until a yellow crystalline precipitate formed, collected by filtration, washed with water and dried to afford compound 3 in 77.0% (3.84 g) yield as a yellow solid.

(Z)-3-(2-aminoethyl)-5-(4-ethoxybenzylidene)thiazolidine-2,4-dione (3)

Compound 2 (1.26 g, 5.08 mmol), 2-(tritylamino)ethanol (2.00 g, 6.60 mmol) and triphenylphosphine (1.80 g, 6.86 mmol) were dissolved in 51 mL of anhydrous THF, and stirred at room temperature for 5 min. DIAD (1.3 mL, 6.60 mmol) was added to the reaction mixture and then stirred overnight at 45° C. The reaction mixture was diluted with ethyl acetate and washed with sat'd $NH_4Cl$ aqueous solution. The organic layer was collected, dried over anhydrous $Na_2SO_4$, filtered, concentrated and purified by silica column chromatography (30% ethyl acetate in hexanes) to afford 3 (75.0%, 2.71 g) as a white solid.

(Z)-3-(2-aminoethyl)-5-(4-ethoxybenzylidene)thiazolidine-2,4-dione (76)

The title compound 76 was prepared from 3 (1.43 g, 2.68 mmol) in a manner to that described for 6 in 72.0% (1.09 g) as a white solid.

5-(4-ethoxybenzyl)thiazolidine-2,4-dione (4)

To a suspension of lithium borohydride (0.22 g, 10.04 mmol) in 40 mL of THF-pyridine (ratio 1:1), compound 3 (1.00 g, 4.02 mmol) was added at 0° C. The reaction mixture was stirred at 80° C. for 12 h and then cooled to 0° C. 21 mL of 4 N HCl aqueous solution was added carefully and the resulting suspension was stirred at 0° C. for 10 min, and refluxed for 1 h. After cooling down at room temperature, the solvent was removed by evaporation. The residue was dissolved in ethyl acetate and washed with water. The organic layer was collected, dried over anhydrous $Na_2SO_4$, filtered, concentrated and purified by silica column chromatography (50% ethyl acetate in hexanes) to afford compound 4 in 76.6% (0.77 g) yield as a colorless oil.

tert-butyl (2-(5-(4-ethoxybenzyl)-2,4-dioxothiazolidin-3-yl)ethyl)carbamate (5)

Potassium carbonate (1.40 g, 9.68 mmol) was added to a solution of compound 4 (303 mg, 1.21 mmol) in 4 mL of anhydrous DMF at 0° C. After stifling the reaction mixture for 20 min, a solution of tert-butyl (2-bromoethyl)carbamate (268 mg, 1.21 mmol) in anhydrous DMF (2 mL) was added and then the reaction mixture was stirred at room temperature for 3 h. The reaction was quenched by adding water and then extracted with ethyl acetate. The ethyl acetate layer was washed with 10% $NH_4Cl$ aqueous solution followed by water and dried over anhydrous $Na_2SO_4$, filtered, concentrated and purified by silica column chromatography (20% ethyl acetate in hexanes) to afford compound 5 in 53.1% (253 mg) as a colorless oil.

3-(2-aminoethyl)-5-(4-ethoxybenzyl)thiazolidine-2,4-dione (6)

Compound 5 (80 mg, 0.20 mmol) was dissolved in 50% TFA in dichloromethane (2 mL) and then stirred at room temperature for 1 h. The solvent was removed by evaporation and the residue was dissolved in dioxane (2 mL), and evaporated again. The solid was collected by filtration, washed with ethyl ether, and dried to afford compound 6 in 58.5% (48 mg) yield as a white solid.

(Z)-5-(4-ethoxybenzylidene)-2-thioxothiazolidin-4-one (8)

4-Ethoxybenzaldehyde (2.78 mL, 20.00 mmol) and rhodanine 7 (3.75 g, 32.0 mmol) were dissolved in 80 mL of anhydrous ethanol at room temperature, and piperidine (0.60 mL, 6.0 mmol) was added to the reaction flask. The reaction mixture was stirred at 75° C. for 1 day and then allowed to cool down to room temperature until a yellow crystalline precipitate formed, and the solid was collected by filtration, washed with water and ethyl acetate, and dried to afford compound 8 in 80.0% (2.99 g) yield as a yellow solid.

(Z)-3-(2-aminoethyl)-5-(4-ethoxybenzylidene)-2-thioxothiazolidin-4-one (9)

To compound 8 (50 mg, 0.18 mmol), $HOCH_2CH_2NHTr$ (54 mg, 0.18 mmol) and triphenylphosphine (73 mg, 0.28 mmol) dissolved in 15 mL of anhydrous THF was added DIAD (55 µL, 0.28 mmol) and stirred for 12 h. Reaction was reduced in vacuo and purified by column chromatography (10% ethyl acetate in hexanes) to give 67 mg (67.7%) of a yellow oil. Deprotection following the procedure of compound 6 gave the title compound 9 as a yellow solid (53%, 40 mg).

3-(triphenylphosphoranylidene)pyrrolidine-2,5-dione (11)

Maleimide (0.60 g, 6.05 mmol) and triphenylphosphine (1.57 g, 5.97 mmol) were dissolved in 40 mL of acetone and the reaction mixture was stirred at 65° C. for 1 h. After cooling down to room temperature, the solid was collected by filtration, washed with acetone, and dried to afford compound 11 in 82.5% (1.77 g) yield as a white solid.

(E)-3-(4-ethoxybenzylidene)pyrrolidine-2,5-dione (12)

The title compound 12 was prepared from 4-ethoxybenzaldehyde (0.22 mL, 1.60 mmol) and compound 11 (1.03 g, 2.88 mmol) in a manner similar to that described for 3 in 92.5% (342 mg) yield as a yellow solid.

(E)-1-(2-aminoethyl)-3-(4-ethoxybenzylidene)pyrrolidine-2,5-dione (13). Step 1

Potassium carbonate (180 mg, 1.30 mmol) was added to a solution of compound 12 (100 mg, 0.43 mmol) in 3 mL of anhydrous DMF at 0° C. After stirring the reaction mixture for 20 min, a solution of tert-butyl (2-bromoethyl)carbamate (96 mg, 0.43 mmol) in anhydrous DMF (1 mL) was added and then the reaction mixture was stirred at room temperature for 3 h. The reaction was quenched by adding water and extracted with ethyl acetate. The ethyl acetate layer was washed with 10% $NH_4Cl$ aqueous solution followed by water and dried over anhydrous $Na_2SO_4$, filtered, concentrated and purified by silica column chromatography (20% ethyl acetate in hexanes) to afford 70 mg (43.2%) of Boc-protected 13 as a white solid.

Step 2. The title compound 13 was prepared from Boc-protected 13 (47 mg, 0.13 mmol) in a manner similar to that described for 6 in 92.0% (45 mg) yield as a white solid.

(E)-3-(4-ethoxybenzylidene)pyrrolidin-2-one (16)

4-Ethoxybenzaldehyde (633 mg, 4.22 mmol) and 15 (596 mg, 4.69 mmol) were dissolved in 6 mL of anhydrous THF, and potassium tert-butoxide (631 mg, 5.62 mmol) was added to the reaction flask. The reaction mixture was stirred at 55° C. for 1 h and then allowed to cool down to room temperature until a yellow crystalline precipitate formed, and the solid was collected by filtration, washed with water and ethyl acetate, and dried to afford compound 16 in 45.0% (411 mg) as a yellow solid.

(E)-1-(2-aminoethyl)-3-(4-ethoxybenzylidene)pyrrolidin-2-one (17)

To compound 16 (50 mg, 0.23 mmol) in 7 mL of anhydrous DMF was added sodium hydride (10 mg, 0.23 mmol) and stirred for 1 h. MsOCH$_2$CH$_2$NHTr (174 mg, 0.46 mmol) was added and stirred overnight. Reaction was reduced in vacuo and the product was purified by column chromatography (10% ethyl acetate in hexanes) to give 67 mg (58%) of clear oil. Deprotection following the procedure of compound 6 gave the title compound 17 as a yellow solid (45%, 33 mg).

(E)-3-(4-ethoxyphenyl)acrylic acid (19)

A solution of 4-ethoxybenzaldehyde (1.00 mL, 7.20 mmol) and piperidine (0.11 mL, 1.08 mmol) in 40 mL of pyridine was heated to 120° C. A solution of malonic acid (1.50 g, 14.40 mmol) in 40 mL of pyridine was added dropwise over 30 min and the reaction solution was stirred at 120° C. for 4 h. After cooling down to 0° C., excess amount of concentrated HCl was added carefully to make ~pH 1. A white crystalline precipitate formed, and the solid was collected by filtration, washed with 0.1 N HCl aqueous solution, and dried to afford compound 19 in 99.5% (1.40 g) of pure 19 as a white solid.

(E)-N-(2-aminoethyl)-3-(4-ethoxyphenyl)acrylamide (20)

Step 1. To a mixture of compound 19 (120 mg, 0.63 mmol), HBTU (360 mg, 0.94 mmol), tert-butyl (2-aminoethyl)carbamate (100 mg, 0.63 mmol) and DIPEA (163 μL, 0.94 mmol) was added 6 mL of DMF at room temperature. The reaction mixture was stirred for 3 h at room temperature and then the reaction was quenched by adding water. The white solid was collected by filtration, washed with water and ethyl ether, and dried to afford 208 mg (99.5%) of Boc-protected 20 as a white solid.

Step 2. The title compound 20 was prepared from Boc-protected 20 (60 mg, 0.18 mmol) in a manner similar to that described for 6 in 75.0% (47 mg) yield as a white solid.

(Z)-tert-butyl (3-(5-(4-ethoxybenzylidene)-2,4-dioxothiazolidin-3-yl)propyl)carbamate (21a)

Potassium carbonate (350 mg, 2.53 mmol) was added to a solution of compound 2 (210 mg, 0.84 mmol) in 4 mL of anhydrous DMF at 0° C. After stirring of reaction mixture for 20 min, a solution of tert-butyl (3-bromopropyl)carbamate (200 mg, 0.84 mmol) in anhydrous DMF (3 mL) was added and then the reaction mixture was stirred at room temperature for 3 h. The reaction was quenched by adding water and extracted with ethyl acetate. The ethyl acetate layer was washed with 10% NH$_4$Cl aqueous solution followed by water and dried over anhydrous Na$_2$SO$_4$, filtered, concentrated and purified by silica column chromatography (20% ethyl acetate in hexanes) to afford compound 21a (78.8%, 270 mg) as a white solid.

(Z)-tert-butyl (1-(5-(4-ethoxybenzylidene)-2,4-dioxothiazolidin-3-yl)propan-2-yl)carbamate (21b)

The title compound 21b was prepared from compound 2 (260 mg, 1.04 mmol) and tert-butyl (1-bromopropan-2-yl)carbamate (247 mg, 1.04 mmol) in a manner similar to that described for 21a. Yield=22.5%, 95.0 mg.

(Z)-tert-butyl (2-(5-(4-ethoxybenzylidene)-2,4-dioxothiazolidin-3-yl)propyl)carbamate (21c)

The title compound 21c was prepared from compound 2 (300 mg, 1.20 mmol) and tert-butyl (2-bromopropyl)carbamate (286 mg, 1.20 mg) in a manner similar to that described for 21a. Yield=15.4%, 75 mg.

(S,Z)-methyl 2-((tert-butoxycarbonyl)amino)-3-(5-(4-ethoxybenzylidene)-2,4-dioxothiazolidin-3-yl)propanoate (21d)

Compound 2 (285 mg, 1.15 mmol), (S)-methyl 2-((tert-butoxycarbonyl)amino)-3-hydroxypropanoate (251 mg, 1.15 mmol) and triphenylphosphine (452 mg, 1.72 mmol) were dissolved in 11 mL of anhydrous THF, and stirred at room temperature for 5 min. DIAD (338 μL, 1.72 mmol) was added to the reaction mixture and then stirred overnight at 45° C. The reaction mixture was diluted with ethyl acetate and washed with sat'd NH$_4$Cl aqueous solution. The organic layer was collected, dried over anhydrous Na$_2$SO$_4$, filtered, concentrated and purified by silica column chromatography (30% ethyl acetate in hexanes) to afford compound 21d (99.5%, 517 mg) as a white solid.

(Z)-di-tert-butyl (2-(5-(4-ethoxybenzylidene)-2,4-dioxothiazolidin-3-yl)propane-1,3-diyl)dicarbamate (21e)

The title compound 21e was prepared from compound 2 (292 mg, 1.17 mmol) and di-tert-butyl (2-bromopropane-1,3-diyl)dicarbamate (413 mg, 1.17 mg) in a manner similar to that described for 21a. Yield=23.9%, 130 mg.

(Z)-3-(3-aminopropyl)-5-(4-ethoxybenzylidene)thiazolidine-2,4-dione (22a)

The title compound 22a was prepared from compound 21a (157 mg, 0.39 mmol) in a manner similar to that described for 6 in 90.3% (148 mg) yield as a white solid.

(Z)-3-(2-aminopropyl)-5-(4-ethoxybenzylidene)thiazolidine-2,4-dione (22b)

The title compound 22b was prepared from compound 21b (57 mg, 0.14 mmol) in a manner similar to that described for 6 in 76.5% (45 mg) yield as a white solid.

(Z)-3-(1-aminopropan-2-yl)-5-(4-ethoxybenzylidene)thiazolidine-2,4-dione (22c)

The title compound 22c was prepared from compound 21c (64 mg, 0.16 mmol) in a manner similar to that described for 6 in 71.4% (48 mg) yield as a white solid.

(S,Z)-methyl 2-amino-3-(5-(4-ethoxybenzylidene)-2,4-dioxothiazolidin-3-yl)propanoate (22d)

The title compound 22d was prepared from compound 21d (120 mg, 0.27 mmol) in a manner similar to that described for 6 in 35.5% (44 mg) yield as a light-yellow solid.

(Z)-3-(1,3-diaminopropan-2-yl)-5-(4-ethoxybenzylidene)thiazolidine-2,4-dione (22e)

The title compound 22e was prepared from compound 21e (70 mg, 0.13 mmol) in a manner similar to that described for 6 in 96.7% (55 mg) yield as a light-yellow solid.

(Z)-5-(4-ethoxybenzylidene)-3-(2-(methylamino)ethyl)thiazolidine-2,4-dione (23a)

To a solution of compound 76 (122 mg, 0.30 mmol) in 4 mL of 1,2-dichloroethane was added triethylamine (84 µL, 0.60 mmol), aqueous formaldehyde (37%, 24 µL, 0.30 mmol) and sodium triacetoxyborohydride (254 mg, 1.20 mmol). The reaction mixture was allowed to stir overnight at room temperature. The reaction was quenched by adding sat'd aqueous NaHCO$_3$ and stirred at room temperature for 20 min. The reaction mixture was partitioned between ethyl acetate and sat'd aqueous NaHCO$_3$, the organic layer was washed with brine, collected, dried over anhydrous Na$_2$SO$_4$, filtered, concentrated and purified by silica column chromatography using dichloromethane/methanol/NH$_4$OH (ratio: 92/7/1) to afford compound 23a (38.1%, 35 mg) as a yellow solid.

(Z)-5-(4-ethoxybenzylidene)-3-(2-(ethylamino)ethyl)thiazolidine-2,4-dione (23b)

To compound 3 (225 mg, 0.91 mmol), HOCH$_2$CH$_2$N(Et)Tr (300 mg, 0.91 mmol) and triphenylphosphine (357 mg, 1.36 mmol) dissolved in anhydrous THF (20 mL) was added DIAD (268 µL, 1.36 mmol) and stirred for 12 h. Reaction was reduced in vacuo and column chromatography to give 276 mg of a yellow solid. Deprotection following the procedure of compound 6 gave the title compound 23b as a yellow solid (28.0%, 83 mg).

(Z)-5-(4-ethoxybenzylidene)-3-(2-(isobutylamino)ethyl)thiazolidine-2,4-dione (23c)

To compound 3 (90 mg, 0.36 mmol), HOCH$_2$CH$_2$N(iBu)Tr (130 mg, 0.36 mmol) and triphenylphosphine (142 mg, 0.54 mmol) dissolved in anhydrous THF (20 mL) was added DIAD (107 µL, 0.54 mmol) and stirred for 12 h. Reaction was reduced in vacuo and column chromatography to give 130 mg of a yellow foam. Deprotection following the procedure of compound 6 gave the title compound 23c as a yellow solid (37.1%, 46 mg).

(Z)-3-(2-(benzylamino)ethyl)-5-(4-ethoxybenzylidene)thiazolidine-2,4-dione (23d)

The title compound 23d was prepared from compound 76 (204 mg, 0.70 mmol), benzaldehyde (71 µL, 0.70 mmol) and sodium triacetoxyborohydride (445 mg, 2.10 mmol) in a manner similar to that described for 23a in 46.0% (123 mg) yield as a light-yellow solid.

(Z)-4-(((2-(5-(4-ethoxybenzylidene)-2,4-dioxothiazolidin-3-yl)ethyl)amino)methyl)benzonitrile (23e)

The title compound 23e was prepared from compound 76 (146 mg, 0.50 mmol), 4-cyanobenzaldehyde (37 µL, 0.50 mmol) and sodium triacetoxyborohydride (318 mg, 1.50 mmol) in a manner similar to that described for 23a in 69.0% (140 mg) yield as a light-yellow solid.

(Z)-3-(2-(dimethylamino)ethyl)-5-(4-ethoxybenzylidene)thiazolidine-2,4-dione (24a)

To a solution of compound 76 (122 mg, 0.30 mmol) in 4 mL of 1,2-dichloroethane was added triethylamine (84 µL, 0.60 mmol), aqueous formaldehyde (37%, 24 µL, 0.30 mmol) and sodium triacetoxyborohydride (254 mg, 1.20 mmol). The reaction mixture was allowed to stir overnight at room temperature. The reaction was quenched by adding sat'd aqueous NaHCO$_3$ and stirred at room temperature for 20 min. The reaction mixture was partitioned between ethyl acetate and sat'd aqueous NaHCO$_3$, the organic layer was washed with brine, collected, dried over anhydrous Na$_2$SO$_4$, filtered, concentrated and purified by silica column chromatography using dichloromethane/methanol/NH$_4$OH (ratio: 92/7/1) to afford compound 24a (76.2%, 73 mg) as a yellow solid.

(Z)-3-(2-(dibenzylamino)ethyl)-5-(4-ethoxybenzylidene)thiazolidine-2,4-dione (24b)

The title compound 24b was prepared from compound 76 (117 mg, 0.40 mmol), benzaldehyde (82 µL, 0.80 mmol) and sodium triacetoxyborohydride (254 mg, 1.20 mmol) in a manner similar to that described for 23a in 93.1% (176 mg) yield as a light-yellow solid.

(Z)-3-(((4-cyanobenzyl)(2-(5-(4-ethoxybenzylidene)-2,4-dioxothiazolidin-3-yl)ethyl)amino)methyl)benzonitrile (24c)

The title compound 24c was prepared from compound 76 (88 mg, 0.30 mmol), 4-cyanobenzaldehyde (79 mg, 0.60 mmol) and sodium triacetoxyborohydride (190 mg, 0.90 mmol) in a manner similar to that described for 23a in 68.5% (110 mg) yield as a yellow solid.

(Z)—N-(2-(5-(4-ethoxybenzylidene)-2,4-dioxothiazolidin-3-yl)ethyl)acetamide (25a)

To a solution of compound 76 (101 mg, 0.25 mmol) in 5 mL of dichloromethane was added triethylamine (105 µL, 0.75 mmol) and acetic anhydride (26.0 µL, 0.28 mmol). After being stirred at room temperature overnight, the reaction solution was diluted with 50 mL of dichloromethane, washed with water, collected the organic layer, dried over Na$_2$SO$_4$, filtered, concentrated and purified by silica column chromatography (33% dichloromethane in ethyl acetate) to afford 74 mg (88.6%) of the title compound 25a as a light-yellow solid.

(Z)—N-(2-(5-(4-ethoxybenzylidene)-2,4-dioxothiazolidin-3-yl)ethyl)-2,2,2-trifluoroacetamide (25b)

To a solution of compound 76 (81 mg, 0.20 mmol) in 4 mL of dichloromethane was added potassium carbonate (83 mg, 0.60 mmol) followed by trifluoroacetic anhydride (31 µL, 0.22 mmol). After being stirred at room temperature for 3 h, the reaction solution was diluted with 50 mL of dichloromethane, washed with water, collected the organic layer, dried over $Na_2SO_4$, filtered, concentrated and purified by silica column chromatography (6% ethyl acetate in dichloromethane) to afford 62 mg (81.0%) of the title compound 25b as a light-yellow solid.

(Z)-tert-butyl (2-(5-(4-ethoxybenzylidene)-2,4-dioxothiazolidin-3-yl)ethyl)carbamate (25c)

To a solution of compound 76 (101 mg, 0.25 mmol) in 3 mL of dichloromethane was added DIPEA (131 µL, 0.75 mmol) followed by pivaloyl chloride (34 µL, 0.28 mmol). After being stirred at room temperature overnight, the reaction solution was diluted with 50 mL of dichloromethane, washed with water, collected the organic layer, dried over $Na_2SO_4$, filtered, concentrated and purified by silica column chromatography (10% ethyl acetate in hexanes) to afford 89 mg (90.8%) of the title compound 25c as a yellow solid.

(Z)-4-cyano-N-(2-(5-(4-ethoxybenzylidene)-2,4-dioxothiazolidin-3-yl)ethyl)benzamide (25d)

To a solution of 4-cyanobenzoic acid (46 mg, 0.31 mmol) in 3 mL of DMF was added DIPEA (131 µL, 0.75 mmol) followed by HBTU (114 mg, 0.30 mmol). After being stirred at room temperature for 1 h, compound 76 (101 mg, 0.25 mmol) was added and then the reaction mixture was stirred at room temperature overnight. The reaction solution was diluted with 50 mL of ethyl acetate and washed with water (30 mL×5), collected the organic layer, dried over $Na_2SO_4$, filtered, concentrated and purified by silica column chromatography (15% ethyl acetate in hexanes) to afford 97 mg (92.1%) of the title compound 25d as a light-yellow solid.

(Z)-methyl (2-(5-(4-ethoxybenzylidene)-2,4-dioxothiazolidin-3-yl)ethyl)carbamate (26a)

The title compound 26a was prepared from compound 76 (101 mg, 0.25 mmol), methyl chloroformate (21 µL, 0.28 mmol) and DIPEA (131 µL, 0.75 mmol) in a manner similar to that described for 25a in 98.2% (86 mg) yield as a yellow solid.

(Z)-tert-butyl (2-(5-(4-ethoxybenzylidene)-2,4-dioxothiazolidin-3-yl)ethyl)carbamate (26b)

The title compound 26b was prepared from compound 76 (405 mg, 0.50 mmol), di-tert-butyl dicarbonate (153 mg, 0.70 mmol) and DIPEA (261 µL, 1.50 mmol) in a manner similar to that described for 25a in 97.9% (192 mg) yield as a light-yellow solid.

(Z)-isobutyl (2-(5-(4-ethoxybenzylidene)-2,4-dioxothiazolidin-3-yl)ethyl)carbamate (26c)

The title compound 26c was prepared from compound 76 (70 mg, 0.17 mmol), isobutyl chloroformate (25 µL, 0.19 mmol) and DIPEA (75 µL, 0.43 mmol) in a manner similar to that described for 25a in 96.4% (65 mg) yield as a light-yellow solid.

(Z)-benzyl (2-(5-(4-ethoxybenzylidene)-2,4-dioxothiazolidin-3-yl)ethyl)carbamate (26d)

The title compound 26d was prepared from compound 76 (70 mg, 0.17 mmol), benzyl chloroformate (27 µL, 0.19 mmol) and DIPEA (75 µL, 0.43 mmol) in a manner similar to that described for 25a in 95.5% (70 mg) yield as a light-yellow solid.

(Z)-(9H-fluoren-9-yl)methyl (2-(5-(4-ethoxybenzylidene)-2,4-dioxothiazolidin-3-yl)ethyl)carbamate (26e)

The title compound 26e was prepared from compound 76 (101 mg, 0.25 mmol), Fmoc chloride (71 mg, 0.28 mmol) and DIPEA (131 µL, 0.75 mmol) in a manner similar to that described for 25a in 96.4% (124 mg) yield as a yellow solid.

(Z)—N-(2-(5-(4-ethoxybenzylidene)-2,4-dioxothiazolidin-3-yl)ethyl)methanesulfonamide (27a)

The title compound 27a was prepared from compound 76 (101 mg, 0.25 mmol), methylsulfonyl chloride (21 µL, 028 mmol) and DIPEA (131 µL, 0.75 mmol) in a manner similar to that described for 25a in 96.2% (89 mg) yield as a yellow solid.

(Z)-4-cyano-N-(2-(5-(4-ethoxybenzylidene)-2,4-dioxothiazolidin-3-yl)ethyl)benzenesulfonamide (27b)

The title compound 27b was prepared from compound 76 (101 mg, 0.25 mmol), 4-cyano-benzenesulfonyl chloride (55 mg, 0.28 mmol) and DIPEA (131 µL, 0.75 mmol) in a manner similar to that described for 25a in 92.0% (105 mg) yield as a light-yellow solid.

(Z)—N-(2-(5-(4-ethoxybenzylidene)-2,4-dioxothiazolidin-3-yl)ethyl)-1-methyl-1H-imidazole-4-sulfonamide (27c)

The title compound 27c was prepared from compound 76 (101 mg, 0.25 mmol), 1-methylimidazole-4-sulfonyl chloride (50 mg, 0.28 mmol) and DIPEA (131 µL, 0.75 mmol) in a manner similar to that described for 25a in 98.0% (108 mg) yield as a light-yellow solid.

(Z)-3-((1H-imidazol-5-yl)methyl)-5-(4-ethoxybenzylidene)thiazolidine-2,4-dione (28a)

Step 1. To a solution of compound 2 (150 mg, 0.60 mmol) in 20 mL of anhydrous THF was added (1-trityl-1H-imidazol-5-yl)methanol (205 mg, 0.60 mmol), triphenylphosphine (237 mg, 0.90 mmol) and DIAD (178 µL, 0.90 mmol). The reaction mixture was stirred at 45° C. overnight. The solvent was removed by evaporation and the residue was dissolved in ethyl acetate, and washed with sat'd aqueous $NH_4Cl$. The organic layer was collected, dried over anhydrous $Na_2SO_4$, filtered, concentrated and purified by silica column chromatography (30% ethyl acetate in hexanes) to afford Trityl-protected 28a in 61.1% (210 mg) yield as a white solid.

Step 2 (cleavage of trityl group). The Trityl-protected 28a (90 mg, 0.16 mmol) was dissolved in 20% TFA solution in dichloromethane and the reaction mixture was stirred at room temperature for 1 h. The solvent was removed by evaporation and the precipitate was collected by filtration, washed with ethyl ether, and dried to afford 61 mg (84.8%) of pure 28a as a light-yellow solid.

(Z)-3-((6-aminopyridin-2-yl)methyl)-5-(4-ethoxybenzylidene)thiazolidine-2,4-dione (28b)

Step 1. Potassium carbonate (131 mg, 0.95 mmol) was added to a solution of compound 2 (78 mg, 0.32 mmol) in 3 mL of anhydrous DMF at 0° C. After stifling of the reaction mixture for 20 min, a solution of tert-butyl (6-(bromomethyl) pyridin-2-yl)carbamate (90 mg, 0.32 mmol) in 1 mL of anhydrous DMF was added and then the reaction mixture was stirred at room temperature for 3 h. The reaction was quenched by adding water and extracted with ethyl acetate. The ethyl acetate layer was washed with 10% $NH_4Cl$ aqueous solution followed by water and dried over anhydrous $Na_2SO_4$, filtered, concentrated and purified by silica column chromatography (20% ethyl acetate in hexanes) to afford 112 mg (78.1%) of Boc protected 28b as a yellow solid.

Step 2 (cleavage of Boc group). The title compound 28b was prepared from Boc-protected 28b (60 mg, 0.13 mmol) in a manner similar to that described for 6 in 78.0% (48 mg) yield as a yellow solid.

(Z)-1-(2-(5-(4-ethoxybenzylidene)-2,4-dioxothiazolidin-3-yl)ethyl)guanidine (28c)

The title compound 28c was prepared from compound 2 (101 mg, 0.25 mmol), N,N'-di-Boc-1H-pyrazole-1-carboxamidine (85 mg, 0.27 mmol) and DIPEA (65 μL, 0.38 mmol) in a manner similar to that described for 28b in 81.1% (108 mg) yield as a yellow solid.

(Z)-5-(4-ethoxybenzylidene)-3-propylthiazolidine-2,4-dione (28d)

Potassium carbonate (93 mg, 0.60 mmol) was added to a solution of compound 2 (75 mg, 0.30 mmol) in 3 mL of anhydrous DMF at 0° C. After stifling of the reaction mixture for 20 min, a solution of 1-bromopropane (30 μL, 0.33 mmol) in 1 mL of anhydrous DMF was added and then the reaction mixture was stirred at room temperature overnight. The reaction was quenched by adding water and extracted with ethyl acetate. The ethyl acetate layer was washed with water (4×20 mL) and dried over anhydrous $Na_2SO_4$, filtered, concentrated and purified by silica column chromatography (15% ethyl acetate in hexanes) to afford 82 mg (93.9%) as a light-yellow solid.

(Z)-5-(4-ethoxybenzylidene)-3-(2-hydroxyethyl) thiazolidine-2,4-dione (28e)

The title compound 28e was prepared from compound 2 (249 mg, 1.00 mmol), ethane-1,2-diol (111 μL, 2.00 mmol), triphenylphosphine (524 mg, 2.00 mmmol) and DIAD (394 μL, 2.00 mmol) in a manner similar to that described for 9 in 95.2% (279 mg) yield as a white solid.

(Z)-3-(2-chloroethyl)-5-(4-ethoxybenzylidene)thiazolidine-2,4-dione (28f)

The title compound 28f was prepared from compound 2 (249 mg, 1.00 mmol), 2-chloroethanol (100 μL, 1.50 mmol), triphenylphosphine (393 mg, 1.50 mmmol) and DIAD (295 μL, 1.50 mmol) in a manner similar to that described for 9 in 88.5% (276 mg) yield as a light-yellow solid.

(Z)-tert-butyl 2-(5-(4-ethoxybenzylidene)-2,4-dioxothiazolidin-3-yl)acetate (28g)

The title compound 28g was prepared from compound 2 (249 mg, 1.00 mmol), tert-butyl bromoacetate (215 mg, 1.10 mmol) and potassium carbonate (276 mg, 2.00 mmol) in a manner similar to that described for 28d in 99.0% (360 mg) yield as a pale-yellow solid.

(Z)-2-(5-(4-ethoxybenzylidene)-2,4-dioxothiazolidin-3-yl)acetic acid (28h)

The title compound 28h was prepared by deprotection of tert-butyl group of compound 28g (300 mg, 0.82 mmol). Deprotection following the procedure of compound 6 gave the title compound 28h as a yellow solid (93.4%, 235 mg).

(Z)-3-benzyl-5-(4-ethoxybenzylidene)thiazolidine-2,4-dione (28i)

The title compound 28i was prepared from compound 2 (75 mg, 0.30 mmol), benzyl bromide (39 μL, 0.33 mmol) and potassium carbonate (83 mg, 0.60 mmol) in a manner similar to that described for 28d in 99.6% (101 mg) yield as a white solid.

(Z)-5-(4-ethoxybenzylidene)-3-(pyridin-2-ylmethyl) thiazolidine-2,4-dione (28j)

The title compound 28j was prepared from compound 2 (75 mg, 0.30 mmol), 2-picolyl chloride.HCl (54 mg, 0.33 mmol), sodium iodide (45 mg, 0.30 mmol) and potassium carbonate (104 mg, 0.75 mmol) in a manner similar to that described for 28d in 97.5% (99 mg) yield as a white solid.

(Z)-5-(4-ethoxybenzylidene)-3-(pyridin-3-ylmethyl) thiazolidine-2,4-dione (28k)

The title compound 28k was prepared from compound 2 (75 mg, 0.30 mmol), 3-picolyl chloride.HCl (54 mg, 0.33 mmol), sodium iodide (45 mg, 0.30 mmol) and potassium carbonate (124 mg, 0.90 mmol) in a manner similar to that described for 28d in 93.1% (95 mg) yield as a white solid.

(Z)-5-(4-ethoxybenzylidene)-3-(pyridin-4-ylmethyl) thiazolidine-2,4-dione (28l)

The title compound 28l was prepared from compound 2 (75 mg, 0.30 mmol), 4-picolyl chloride.HCl (54 mg, 0.33 mmol), sodium iodide (45 mg, 0.30 mmol) and potassium carbonate (124 mg, 0.90 mmol) in a manner similar to that described for 28d in 96.1% (98 mg) yield as a white solid.

(Z)-4-((5-(4-ethoxybenzylidene)-2,4-dioxothiazolidin-3-yl)methyl)benzonitrile (28m)

The title compound 28m was prepared from compound 2 (75 mg, 0.30 mmol), p-cyanobenzyl bromide (65 mg, 0.33 mmol) and potassium carbonate (83 mg, 0.60 mmol) in a manner similar to that described for 28d in 81.5% (89 mg) yield as a light-yellow solid.

(Z)-5-(4-ethoxybenzylidene)-3-(4-nitrobenzyl)thiazolidine-2,4-dione (28n)

The title compound 28n was prepared from compound 2 (150 mg, 0.60 mmol), p-nitrobenzyl bromide (143 mg, 0.66 mmol) and potassium carbonate (166 mg, 1.20 mmol) in a manner similar to that described for 28d in 99.5% (229 mg) yield as a white solid.

(Z)-3-(4-aminobenzyl)-5-(4-ethoxybenzylidene)thiazolidine-2,4-dione (28o)

To a solution of compound 28n (100 mg, 0.26 mol) in 10 mL of chloroform-ethanol co-solvent (ratio, 4:1) was added tin(II) chloride.dihydrate (293 mg, 1.30 mmol). The reaction mixture was stirred at 45° C. overnight. The reaction mixture was diluted with dichloromethane and washed with sat'd aqueous NaHCO$_3$, collected the organic layer, dried over anhydrous Na$_2$SO$_4$, filtered, concentrated and purified by silica column chromatography (10% ethyl acetate in dichloromethane) to afford 88 mg (97.0%) of pure 28o as a yellow-orange solid.

(Z)-tert-butyl 4-((5-(4-ethoxybenzylidene)-2,4-dioxothiazolidin-3-yl)methyl)benzoate (28p)

The title compound 28p was prepared from compound 2 (75 mg, 0.30 mmol), tert-butyl 4-(bromomethyl)benzoate (106 mg, 0.39 mmol) and potassium carbonate (83 mg, 0.60 mmol) in a manner similar to that described for 28d in 96.4% (127 mg) yield as a white solid.

(Z)-4-((5-(4-ethoxybenzylidene)-2,4-dioxothiazolidin-3-yl)methyl)benzoic acid (28q)

The title compound 28q was prepared by deprotection of tert-butyl group of compound 28p (100 mg, 0.23 mmol). Deprotection following the procedure of compound 6 gave the title compound 28q as a white solid (85 mg, 97.3%).

(Z)-3-((5-(4-ethoxybenzylidene)-2,4-dioxothiazolidin-3-yl)methyl)benzoic acid (28r)

Step 1. Potassium carbonate (166 mg, 1.20 mmol) was added to a solution of compound 2 (100 mg, 0.40 mmol) in 4 mL of anhydrous DMF at 0° C. After stirring of the reaction mixture for 20 min, a solution of tert-butyl 3-(bromomethyl)benzoate (110 mg, 0.40 mmol) in 1 mL of anhydrous DMF was added and then the reaction mixture was stirred at room temperature for 3 h. The reaction was quenched by adding water and extracted with ethyl acetate. The ethyl acetate layer was washed with 10% NH$_4$Cl aqueous solution followed by water and dried over anhydrous Na$_2$SO$_4$, filtered, concentrated and purified by silica column chromatography (10% ethyl acetate in hexanes) to afford 116 mg (66.0%) of tert-butyl-28r as a light-yellow solid.
Step 2 (cleavage of tert-butyl group). The title compound 28r was prepared from tert-butyl-28r (60 mg, 0.14 mmol) in a manner similar to that described for 6 in 62.0% (42 mg) yield as a white solid.

(Z)-2-((5-(4-ethoxybenzylidene)-2,4-dioxothiazolidin-3-yl)methyl)benzoic acid (28s)

Step 1. The compound tert-butyl-28s was prepared from compound 2 (290 mg, 1.16 mmol), tert-butyl 2-(bromomethyl)benzoate (314 mg, 1.16 mmol) and potassium carbonate (480 mg, 3.48 mmol) in a manner similar to that described for 28r (step 1) in 61.8% (315 mg) yield as a white-yellow solid.
Step 2 (cleavage of tert-butyl group). The title compound 28s was prepared from tert-butyl-28s (100 mg, 0.23 mmol) in a manner similar to that described for 6 in 67.1% (76 mg) yield as a white solid.

3-(2-(tritylamino)ethyl)thiazolidine-2,4-dione (29)

To a solution of compound 1 (900 mg, 7.69 mmol) in 80 mL of anhydrous THF was 2-(tritylamino)ethanol (3.03 g, 10.00 mmol), triphenylphosphine (2.72 g, 10.40 mmol) and DIAD (1.97 mL, 10.00 mmol). The reaction mixture was stirred at room temperature overnight. The solvent was removed by evaporation and the residue was dissolved in ethyl acetate, and washed with sat'd aqueous NH$_4$Cl. The organic layer was collected, dried over anhydrous Na$_2$SO$_4$, filtered, concentrated and purified by silica column chromatography (20% ethyl acetate in hexanes) to afford 29 in 75.0% (2.31 g) yield as a white solid.

(Z)-3-(2-aminoethyl)-5-benzylidenethiazolidine-2,4-dione (30a)

Benzaldehyde (63 µL, 0.62 mmol) and compound 29 (250 mg, 0.62 mmol) were dissolved in 10 mL of anhydrous ethanol at room temperature, and piperidine (7 µL, 0.062 mmol) was added to the reaction solution. The reaction mixture was stirred at 75° C. for 1 day and then allowed to cool down to room temperature until a yellow crystalline precipitate formed, and the solid was collected by filtration, washed with water and ethyl acetate, and dried to afford a white solid. Deprotection following the procedure of compound 6 gave the title compound 30a as a white solid (48.1%, 74 mg).

(Z)-3-(2-aminoethyl)-5-(3-ethoxybenzylidene)thiazolidine-2,4-dione (30b)

The title compound 30b was prepared from 3-ethoxybenzaldehyde (87 µL, 0.62 mmol) and compound 29 (250 mg, 0.62 mmol) and piperidine (7.0 µL, 0.062 mmol) in a manner similar to that described for 30a in 20.4% (50 mg) yield as a white solid.

(Z)-3-(2-aminoethyl)-5-(2-ethoxybenzylidene)thiazolidine-2,4-dione (30c)

The title compound 30c was prepared from 2-ethoxybenzaldehyde (87 µL, 0.62 mmol) and compound 29 (250 mg, 0.62 mmol) and piperidine (7.0 µL, 0.062 mmol) in a manner similar to that described for 30a in 35.4% (64 mg) yield as a white solid.

(Z)-3-(2-aminoethyl)-5-(4-methylbenzylidene)thiazolidine-2,4-dione (30d)

The title compound 30d was prepared from 4-methylbenzaldehyde (73 µL, 0.62 mmol), compound 29 (250 mg, 0.62 mmol) and piperidine (7.0 µL, 0.062 mmol) in a manner similar to that described for 30a in 36.0% (83 mg) yield as a cream solid.

(Z)-3-(2-aminoethyl)-5-(4-propylbenzylidene)thiazolidine-2,4-dione (30e)

The title compound 30e was prepared from 4-propylbenzaldehyde (92 mg, 0.62 mmol), compound 29 (250 mg, 0.62 mmol) and piperidine (7.0 µL, 0.062 mmol) in a manner similar to that described for 30a in 38.0% (95 mg) yield as a white solid.

(Z)-3-(2-aminoethyl)-5-(4-hydroxybenzylidene)thiazolidine-2,4-dione (30f)

The title compound 30f was prepared from 4-hydroxybenzaldehyde (76 mg, 0.62 mmol), compound 29 (250 mg, 0.62 mmol) and piperidine (20.0 µL, 0.19 mmol) in a manner similar to that described for 30a in 43.0% (102 mg) yield as a yellow solid.

(Z)-3-(2-aminoethyl)-5-(4-isobutoxybenzylidene) thiazolidine-2,4-dione (30g)

To compound trityl-30f (100 mg, 0.20 mmol) and potassium carbonate (82 mg, 0.60 mmol) in 3 mL of anhydrous DMF was added isobutyl iodide (54 µL, 0.40 mmol). The reaction was allowed to stir at 70° C. for 12 h. The reaction solution was diluted with ethyl acetate and washed with water, brine, collected the organic phase, dried over anhydrous $Na_2SO_4$, filtered, concentrated and purified by silica column chromatography. Deprotection following the procedure of compound 6 gave the title compound 30g as a yellow solid (65.2%, 56 mg).

(Z)-3-(2-aminoethyl)-5-(4-(benzyloxy)benzylidene) thiazolidine-2,4-dione (30h)

To compound trityl-30f (100 mg, 0.20 mmol) and potassium carbonate (82 mg, 0.60 mmol) in 3 mL of anhydrous DMF was added benzyl bromide (50 µL, 0.40 mmol). The reaction was allowed to stir at room temperature for 3 h. The reaction solution was diluted with ethyl acetate and washed with water, brine, collected the organic phase, dried over anhydrous $Na_2SO_4$, filtered, concentrated and purified by silica column chromatography. Deprotection following the procedure of compound 6 gave the title compound 30h as a yellow solid (97.0%, 91 mg).

(Z)-3-(2-aminoethyl)-5-(2-hydroxybenzylidene)thiazolidine-2,4-dione (30i)

The title compound 30i was prepared from 2-hydroxybenzaldehyde (76 mg, 0.62 mmol), compound 29 (250 mg, 0.62 mmol) and piperidine (20.0 µL, 0.19 mmol) in a manner similar to that described for 30a in 50.0% (117 mg) yield as a yellow solid.

(Z)-3-(2-aminoethyl)-5-(2-isobutoxybenzylidene) thiazolidine-2,4-dione (30j)

To compound trityl-30i (100 mg, 0.20 mmol) and potassium carbonate (82 mg, 0.60 mmol) in 3 mL of anhydrous DMF was added isobutyl iodide (54 µL, 0.40 mmol). The reaction was allowed to stir at 70° C. for 12 h. The reaction solution was diluted with ethyl acetate and washed with water, brine, collected the organic phase, dried over anhydrous $Na_2SO_4$, filtered, concentrated and purified by silica column chromatography. Deprotection following the procedure of compound 6 gave the title compound 30j as a yellow solid (73.7%, 64 mg).

(Z)-3-(2-aminoethyl)-5-(2-(benzyloxy)benzylidene) thiazolidine-2,4-dione (30k)

To compound trityl-30i (100 mg, 0.20 mmol) and potassium carbonate (82 mg, 0.60 mmol) in 3 mL of anhydrous DMF was added benzyl bromide (50 µL, 0.40 mmol). The reaction was allowed to stir at room temperature for 3 h. The reaction solution was diluted with ethyl acetate and washed with water, brine, collected the organic phase, dried over anhydrous $Na_2SO_4$, filtered, concentrated and purified by silica column chromatography. Deprotection following the procedure of compound 6 gave the title compound 30k as a pale-yellow solid (95.1%, 89 mg).

(Z)-4-((2-((3-(2-aminoethyl)-2,4-dioxothiazolidin-5-ylidene)methyl)phenoxy)methyl)benzonitrile (30l To compound trityl-30i (100 mg, 0.20 mmol) and potassium carbonate (82 mg, 0.60 mmol) in 3 mL of anhydrous DMF was added 4-cyanobenzyl bromide (78 mg, 0.40 mmol). The reaction was allowed to stir at room temperature overnight. The reaction solution was diluted with ethyl acetate and washed with water, brine, collected the organic phase, dried over anhydrous $Na_2SO_4$, filtered, concentrated and purified by silica column chromatography. Deprotection following the procedure of compound 6 gave the title compound 30l as a light-yellow solid (79.1%, 78 mg).

Biology

Cell Proliferation Assay.

Cell proliferation was evaluated by water soluble tetrazolium-1 (WST-1) assay as previously described. Briefly, cells (~5000/well) were seeded in 96 well plates, allowed to recover for 16-20 hours, and then treated with the indicated test compound for 48 hours. After incubation, WST-1 reagent was added and absorbance was read at 450 nm with background subtraction taken at 650 nm. Values were normalized to the control (DMSO only treated) cells.

Luciferase Assay.

HeLa cells were seeded in 24-well plates ($4 \times 10^4$ cells/well) and incubated 18 hours prior to achieve ~60-70% confluent. Cells were transfected with activator protein-1 (pAP1(PMA)-TA-Luc; Clontech) or the serum response element (pGL4.33-SRE; Promega) luciferase reporter plasmids (250 ng/well) using Lipofectamine™ (Invitrogen). After 16 hours, cells were treated with increasing amount of compounds as indicated for 20 minutes, followed by stimulation with EGF (25 ng/mL) for 4.5 hr. The luciferase activity in the cell extracts was determined with a Dual Luciferase Assay System (Promega) according to the manufacturer's instructions. Luciferase activities were monitored with a Lumat LB 9507 luminometer (Berthold Technology) and data were normalized to the amount of protein in each sample.

The entire contents of each of the below mentioned articles is hereby incorporated by reference, the same as set forth at length.

Abramczyk, P., Rainey, M. A., Barnes, R., Martin, L., and Dalby, K. N. (2007) Expanding the repertoire of an ERK2 recruitment site: cysteine footprinting identifies the D-recruitment site as a mediator of Ets-1 binding, *Biochemistry* 46, 9174-9186.

Akella, R., Moon, T. M., and Goldsmith, E. J. (2008) Unique MAP Kinase binding sites, *Biochim Biophys Acta* 1784, 48-55.

Allan, L. A., Morrice, N., Brady, S., Magee, G., Pathak, S., and Clarke, P. R. (2003) Inhibition of caspase-9 through phosphorylation at Thr 125 by ERK MAPK. *Nat Cell Biol* 5, 647-654.

Anonymous (Discovery Studio 2.5, Accelrys Inc.)

Appels, N. M., Beijnen, J. H., and Schellens, J. H. (2005) Development of farnesyl transferase inhibitors: a review. *Oncologist* 10, 565-578.

Arkenau, H. T., Kefford, R., and Long, G. V. (2011) Targeting BRAF for patients with melanoma, *Br J Cancer* 104, 392-398.

Aronov, A. M., Baker, C., Bemis, G. W., Cao, J., Chen, G., Ford, P. J., Germann, U. A., Green, J., Hale, M. R., Jacobs, M., Janetka, J. W., Maltais, F., Martinez-Botella, G., Namchuk, M. N., Straub, J., Tang, Q., and Xie, X. (2007) Flipped out: structure-guided design of selective pyrazolylpyrrole ERK inhibitors, *J Med Chem* 50, 1280-1287.

Arora, A., and Scholar, E. M. (2005) Role of tyrosine kinase inhibitors in cancer therapy. *J Pharmacol Exp Ther* 315, 971-979.

Basbous, J., Chalbos, D., Hipskind, R., Jariel-Encontre, I., and Piechaczyk, M. (2007) Ubiquitin-independent proteasomal degradation of Fra-1 is antagonized by Erk1/2 pathway-mediated phosphorylation of a unique C-terminal destabilizer, *Mol Cell Biol* 27, 3936-3950.

Bernard, D., Coop, A., and MacKerell, A. D., Jr. (2003) 2D Conformationally Sampled Pharmacophore: A Ligand-Based Pharmacophore To Differentiate delta Opioid Agonists from Antagonists. *J Am Chem Soc* 125, 3101-3107.

Bernstein F C, et al. (1977) The Protein Data Bank. A computer-based archival file for macromolecular structures. *Eur J Biochem* 80(2):319-324.

Booy, E. P., Henson, E. S., and Gibson, S. B. (2011) Epidermal growth factor regulates Mcl-1 expression through the MAPK-Elk-1 signalling pathway contributing to cell survival in breast cancer. *Oncogene* 30, 2367-2378.

Bos, J. L. (1989) ras oncogenes in human cancer: a review. *Cancer Res* 49, 4682-4689.

Boston S R, et al. (2011) Characterization of ERK docking domain inhibitors that induce apoptosis by targeting Rsk-1 and caspase-9. *BMC Cancer* 11:7.

Brooks B R, et al. (2009) CHARMM: the biomolecular simulation program. *Journal of computational chemistry* 30(10):1545-1614.

Brose, M. S., Volpe, P., Feldman, M., Kumar, M., Rishi, I., Gerrero, R., Einhorn, E., Herlyn, M., Minna, J., Nicholson, A., Roth, J. A., Albelda, S. M., Davies, H., Cox, C., Brignell, G., Stephens, P., Futreal, P. A., Wooster, R., Stratton, M. R., and Weber, B. L. (2002) BRAF and RAS mutations in human lung cancer and melanoma. *Cancer Res* 62, 6997-7000.

Buchwalter, G., Gross, C., and Wasylyk, B. (2004) Ets ternary complex transcription factors. *Gene* 324, 1-14.

Burkhard K A, Chen F, & Shapiro P (2011) Quantitative analysis of ERK2 interactions with substrate proteins: roles for kinase docking domains and activity in determining binding affinity. *J Biol Chem* 286(4):2477-2485.

Burkhard, K., Smith, S., Deshmukh, R., MacKerell, A. D., Jr., and Shapiro, P. (2009) Development of extracellular signal-regulated kinase inhibitors. *Curr Top Med Chem* 9, 678-689.

Canagarajah B J, Khokhlatchev A, Cobb M H, & Goldsmith E J (1997) Activation mechanism of the MAP kinase ERK2 by dual phosphorylation. *Cell* 90(5):859-869.

Carlson, H. A. (2002) Protein flexibility and drug design: how to hit a moving target, *Curr Opin Chem Biol* 6, 447-452.

Carpenter Ga & Grossberg S (1987) Art-2—Self-Organization of Stable Category Recognition Codes for Analog Input Patterns. *Applied Optics* 26(23):4919-4930.

Cerchietti, L. C., Ghetu, A. F., Zhu, X., Da Silva, G. F., Zhong, S., Matthews, M., Bunting, K. L., Polo, J. M., Fares, C., Arrowsmith, C. H., Yang, S. N., Garcia, M., Coop, A., Mackerell, A. D., Jr., Prive, G. G., and Melnick, A. (2010) A small-molecule inhibitor of BCL6 kills DLBCL cells in vitro and in vivo. *Cancer Cell* 17, 400-411.

Chambers C C, Hawkins G D, Cramer C J, & Truhlar D G (1996) Model for aqueous solvation based on class IV atomic charges and first solvation shell effects. *J. Phys. Chem.* 100(40):16385-16398.

Chen, F., Hancock, C. N., Macias, A. T., Joh, J., Still, K., Zhong, S., MacKerell, A. D., Jr., and Shapiro, P. (2006) Characterization of ATP-independent ERK inhibitors identified through in silico analysis of the active ERK2 structure. *Bioorg Med Chem Lett* 16, 6281-6287.

Chen, F., Mackerell, A. D., Jr., Luo, Y., and Shapiro, P. (2008) Using *Caenorhabditis elegans* as a model organism for evaluating extracellular signal-regulated kinase docking domain inhibitors. *J Cell Commun Signal* 2, 81-92.

Chen, X., Zhong, S., Zhu, X., Dziegielewska, B., Ellenberger, T., Wilson, G. M., MacKerell, A. D., Jr., and Tomkinson, A. E. (2008) Rational design of human DNA ligase inhibitors that target cellular DNA replication and repair. *Cancer Res* 68, 3169-3177.

Chen, Z., Demuth, T. P., Jr., and Wireko, F. C. (2001) Stereoselective synthesis and antibacterial evaluation of 4-amido-isothiazolidinone oxides. *Bioorg Med Chem Lett* 11, 2111-2115.

Chuderland, D., Marmor, G., Shainskaya, A., and Seger, R. (2008) Calcium-mediated interactions regulate the subcellular localization of extracellular signal-regulated kinases. *J Biol Chem* 283, 11176-11188.

Comess, K. M., Sun, C., Abad-Zapatero, C., Goedken, E. R., Gum, R. J., Borhani, D. W., Argiriadi, M., Groebe, D. R., Jia, Y., Clampit, J. E., Haasch, D. L., Smith, H. T., Wang, S., Song, D., Coen, M. L., Cloutier, T. E., Tang, H., Cheng, X., Quinn, C., Liu, B., Xin, Z., Liu, G., Fry, E. H., Stoll, V., Ng, T. I., Banach, D., Marcotte, D., Burns, D. J., Calderwood, D. J., and Hajduk, P. J. (2011) Discovery and characterization of non-ATP site inhibitors of the mitogen activated protein (MAP) kinases, *ACS chemical biology* 6, 234-244.

Connolly M L (1983) Solvent-accessible surfaces of proteins and nucleic acids. *Science* 221(4612):709-713.

Corcoran, R. B., Settleman, J., and Engelman, J. A. (2011) Potential therapeutic strategies to overcome acquired resistance to BRAF or MEK inhibitors in BRAF mutant cancers. *Oncotarget* 2, 336-346.

Cruickshank, D. W. J. (1999) Remarks about protein structure precision, *Acta Crystallographica Section D-Biological Crystallography* 55, 583-601.

Dai, B., Zhao, X. F., Hagner, P., Shapiro, P., Mazan-Mamczarz, K., Zhao, S., Natkunam, Y., and Gartenhaus, R. B. (2009) Extracellular signal-regulated kinase positively regulates the oncogenic activity of MCT-1 in diffuse large B-cell lymphoma. *Cancer Res* 69, 7835-7843.

Dai, B., Zhao, X. F., Mazan-Mamczarz, K., Hagner, P., Corl, S., Bahassi el, M., Lu, S., Stambrook, P. J., Shapiro, P., and Gartenhaus, R. B. (2011) Functional and molecular interactions between ERK and CHK2 in diffuse large B-cell lymphoma. *Nature communications* 2, 402.

Darden T, York D, & Pedersen L (1993) Particle Mesh Ewald—an N.Log(N) Method for Ewald Sums in Large Systems. *Journal of Chemical Physics* 98(12):10089-10092.

Davidson, W., Frego, L., Peet, G. W., Kroe, R. R., Labadia, M. E., Lukas, S. M., Snow, R. J., Jakes, S., Grygon, C. A., Pargellis, C., and Werneburg, B. G. (2004) Discovery and characterization of a substrate selective p38alpha inhibitor, *Biochemistry* 43, 11658-11671.

Davies, B. R., Logie, A., McKay, J. S., Martin, P., Steele, S., Jenkins, R., Cockerill, M., Cartlidge, S., and Smith, P. D. (2007) AZD6244 (ARRY-142886), a potent inhibitor of mitogen-activated protein kinase/extracellular signal-regulated kinase kinase 1/2 kinases: mechanism of action in vivo, pharmacokinetic/pharmacodynamic relationship, and potential for combination in preclinical models. *Mol Cancer Ther* 6, 2209-2219.

Davies, H., Bignell, G. R., Cox, C., Stephens, P., Edkins, S., Clegg, S., Teague, J., Woffendin, H., Garnett, M. J., Bottomley, W., Davis, N., Dicks, E., Ewing, R., Floyd, Y., Gray, K., Hall, S., Hawes, R., Hughes, J., Kosmidou, V., Menzies, A., Mould, C., Parker, A., Stevens, C., Watt, S., Hooper, S., Wilson, R., Jayatilake, H., Gusterson, B. A., Cooper, C., Shipley, J., Hargrave, D., Pritchard-Jones, K., Maitland, N., Chenevix-Trench, G., Riggins, G. J., Bigner, D. D., Palmieri, G., Cossu, A., Flanagan, A., Nicholson, A., Ho, J. W., Leung, S. Y., Yuen, S. T., Weber, B. L., Seigler, H. F., Darrow, T. L., Paterson, H., Marais, R., Marshall, C. J., Wooster, R., Stratton, M. R., and Futreal, P. A. (2002) Mutations of the BRAF gene in human cancer. *Nature* 417, 949-954.

Dibbern, D. A., Jr., and Montanaro, A. (2008) Allergies to sulfonamide antibiotics and sulfur-containing drugs. *Ann Allergy Asthma Immunol* 100, 91-100; quiz 100-103, 111.

Dimitri, C. A., Dowdle, W., MacKeigan, J. P., Blenis, J., and Murphy, L. O. (2005) Spatially separate docking sites on ERK2 regulate distinct signaling events in vivo. *Curr Biol* 15, 1319-1324.

Domina, A. M., Vrana, J. A., Gregory, M. A., Hann, S. R., and Craig, R. W. (2004) MCL1 is phosphorylated in the PEST region and stabilized upon ERK activation in viable cells, and at additional sites with cytotoxic okadaic acid or taxol. *Oncogene* 23, 5301-5315.

Duffy, A., and Kummar, S. (2009) Targeting mitogen-activated protein kinase kinase (MEK) in solid tumors, *Target Oncol* 4, 267-273.

Durchdewald, M., Angel, P., and Hess, J. (2009) The transcription factor Fos: a Janus-type regulator in health and disease. *Histol Histopathol* 24, 1451-1461.

Ekins, S., Boulanger, B., Swaan, P. W., and Hupcey, M. A. (2002) Towards a new age of virtual ADME/TOX and multidimensional drug discovery. *J Comput Aided Mol Des* 16, 381-401.

Ekins, S., Waller, C. L., Swaan, P. W., Cruciani, G., Wrighton, S. A., and Wikel, J. H. (2000) Progress in predicting human ADME parameters in silico. *J Pharmacol Toxicol Methods* 44, 251-272.

Elkins, J. M., Wang, J., Deng, X., Pattison, M. J., Arthur, J. S., Erazo, T., Gomez, N., Lizcano, J. M., Gray, N. S., and Knapp, S. (2013) X-ray crystal structure of ERK5 (MAPK7) in complex with a specific inhibitor, *J Med Chem* 56, 4413-4421.

Emrick, M. A., Hoofnagle, A. N., Miller, A. S., Ten Eyck, L. F., and Ahn, N. G. (2001) Constitutive activation of extracellular signal-regulated kinase 2 by synergistic point mutations, *J Biol Chem* 276, 46469-46479.

Ewing T J A & Kuntz I D (1997) Critical evaluation of search algorithms for automated molecular docking and database screening. *J. Comput. Chem.* 18(9):1175-1189.

Fantz, D. A., Jacobs, D., Glossip, D., and Kornfeld, K. (2001) Docking sites on substrate proteins direct extracellular signal-regulated kinase to phosphorylate specific residues, *J Biol Chem* 276, 27256-27265.

Farooq, A., Chaturvedi, G., Mujtaba, S., Plotnikova, O., Zeng, L., Dhalluin, C., Ashton, R., and Zhou, M. M. (2001) Solution structure of ERK2 binding domain of MAPK phosphatase MKP-3: structural insights into MKP-3 activation by ERK2, *Mol Cell* 7, 387-399.

Feig, M., and Brooks, C. L., III (2004) Recent advances in the development and application of implicit solvent models in biomolecular simulations. *Curr. Opin. Struct. Biol.* 14, 217-224.

Feller S E, Zhang Y H, Pastor R W, & Brooks B R (1995) Constant-Pressure Molecular-Dynamics Simulation—the Langevin Piston Method. *Journal of Chemical Physics* 103(11):4613-4621.

Ferrin T E, Huang C C, Jarvis L E, & Langridge R (1988) The Midas Display System. *J. Mol. Graphics* 6(1):13-27.

Foster, T. J., MacKerell Jr., A. D. and Guvench, O. (2012) Balancing Target Flexibility and Target Denaturation in Computational Fragment-Based Inhibitor Discovery. *Journal of computational chemistry In press*.

Friday, B. B., and Adjei, A. A. (2008) Advances in targeting the Ras/Raf/MEK/Erk mitogen-activated protein kinase cascade with MEK inhibitors for cancer therapy. *Clin Cancer Res* 14, 342-346.

Furci L M, et al. (2007) Inhibition of the bacterial heme oxygenases from *Pseudomonas aeruginosa* and *Neisseria meningitidis*: novel antimicrobial targets. *J. Med. Chem.* 50(16):3804-3813.

Galanis, A., Yang, S. H., and Sharrocks, A. D. (2001) Selective targeting of MAPKs to the ETS domain transcription factor SAP-1, *J Biol Chem* 276, 965-973.

Gee, J. M., Robertson, J. F., Gutteridge, E., Ellis, I. O., Pinder, S. E., Rubini, M., and Nicholson, R. I. (2005) Epidermal growth factor receptor/HER2/insulin-like growth factor receptor signalling and oestrogen receptor activity in clinical breast cancer, *Endocrine-related cancer* 12 Suppl 1, S99-S111.

Gille, H., Kortenjann, M., Thomae, O., Moomaw, C., Slaughter, C., Cobb, M. H., and Shaw, P. E. (1995) ERK phosphorylation potentiates Elk-1-mediated ternary complex formation and transactivation, *Embo J* 14, 951-962.

Goodford P J (1985) A computational procedure for determining energetically favorable binding sites on biologically important macromolecules. *J Med Chem* 28(7):849-857.

Gopal, Y. N., Deng, W., Woodman, S. E., Komurov, K., Ram, P., Smith, P. D., and Davies, M. A. (2010) Basal and treatment-induced activation of AKT mediates resistance to cell death by AZD6244 (ARRY-142886) in Braf-mutant human cutaneous melanoma cells. *Cancer research* 70, 8736-8747.

Greger, J. G., Eastman, S. D., Zhang, V., Bleam, M. R., Hughes, A. M., Smitheman, K. N., Dickerson, S. H., Laquerre, S. G., Liu, L., and Gilmer, T. M. (2012) Combinations of BRAF, MEK, and PI3K/mTOR inhibitors overcome acquired resistance to the BRAF inhibitor GSK2118436 dabrafenib, mediated by NRAS or MEK mutations. *Mol Cancer Ther* 11, 909-920.

Gruda, M. C., Kovary, K., Metz, R., and Bravo, R. (1994) Regulation of Fra-1 and Fra-2 phosphorylation differs during the cell cycle of fibroblasts and phosphorylation in vitro by MAP kinase affects DNA binding activity, *Oncogene* 9, 2537-2547.

Guvench O & MacKerell A D, Jr. (2009) Computational fragment-based binding site identification by ligand competitive saturation. *PLoS computational biology* 5(7):e1000435.

Halgren T A (1999) MMFF VI. MMFF94s option for energy minimization studies. *J. Comput. Chem.* 20(7):720-729.

Halgren T A (1999) MMFF VII. Characterization of MMFF94, MMFF94s, and other widely available force fields for conformational energies and for intermolecular-interaction energies and geometries. *J. Comput. Chem.* 20(7):730-748.

Hancock, C. N., Macias, A., Lee, E. K., Yu, S. Y., Mackerell, A. D., Jr., and Shapiro, P. (2005) Identification of novel extracellular signal-regulated kinase docking domain inhibitors. *J Med Chem* 48, 4586-4595.

Hann M M & Oprea T I (2004) Pursuing the leadlikeness concept in pharmaceutical research. *Curr Opin Chem Biol* 8(3):255-263.

Hatzivassiliou, G., Liu, B., O'Brien, C., Spoerke, J. M., Hoeflich, K. P., Haverty, P. M., Soriano, R., Forrest, W. F., Heldens, S., Chen, H., Toy, K., Ha, C., Zhou, W., Song, K., Friedman, L. S., Amler, L. C., Hampton, G. M., Moffat, J., Belvin, M., and Lackner, M. R. (2012) ERK Inhibition Overcomes Acquired Resistance to MEK Inhibitors. *Mol Cancer Ther* 11, 1143-1154.

Hoofnagle, A. N., Resing, K. A., Goldsmith, E. J., and Ahn, N. G. (2001) Changes in protein conformational mobility upon activation of extracellular regulated protein kinase-2 as detected by hydrogen exchange, *Proc Natl Acad Sci USA* 98, 956-961.

Hsu, T., Trojanowska, M., and Watson, D. K. (2004) Ets proteins in biological control and cancer, *J Cell Biochem* 91, 896-903.

Huang, N., Nagarsekar, A., Xia, G., Hayashi, J., and MacKerell, A. D., Jr. (2004) Identification of non-phosphate-containing small molecular weight inhibitors of the tyrosine kinase p56 Lck SH2 domain via in silico screening against the pY+3 binding site, *J Med Chem* 47, 3502-3511.

Humphrey, W., Dalke, A., and Schulten, K. (1996) VMD: visual molecular dynamics, *Journal of molecular graphics* 14, 33-38, 27-38.

Hynes, J., Dyckman, A. J., Lin, S., Wrobleski, S. T., Wu, H., Gillooly, K. M., Kanner, S. B., Lonial, H., Loo, D., McIntyre, K. W., Pitt, S., Shen, D. R., Shuster, D. J., Yang, X., Zhang, R., Behnia, K., Zhang, H., Marathe, P. H., Doweyko, A. M., Tokarski, J. S., Sack, J. S., Pokross, M., Kiefer, S. E., Newitt, J. A., Banish, J. C., Dodd, J., Schieven, G. L., and Leftheris, K. (2007) Design, Synthesis, and Anti-inflammatory Properties of Orally Active 4-(Phenylamino)-pyrrolo[2,1-f][1,2,4]triazine p38α Mitogen-Activated Protein Kinase Inhibitors, *Journal of Medicinal Chemistry* 51, 4-16.

Ikediobi, O. N., Davies, H., Bignell, G., Edkins, S., Stevens, C., O'Meara, S., Santarius, T., Avis, T., Barthorpe, S., Brackenbury, L., Buck, G., Butler, A., Clements, J., Cole, J., Dicks, E., Forbes, S., Gray, K., Halliday, K., Harrison, R., Hills, K., Hinton, J., Hunter, C., Jenkinson, A., Jones, D., Kosmidou, V., Lugg, R., Menzies, A., Mironenko, T., Parker, A., Perry, J., Raine, K., Richardson, D., Shepherd, R., Small, A., Smith, R., Solomon, H., Stephens, P., Teague, J., Tofts, C., Varian, J., Webb, T., West, S., Widaa, S., Yates, A., Reinhold, W., Weinstein, J. N., Stratton, M. R., Futreal, P. A., and Wooster, R. (2006) Mutation analysis of 24 known cancer genes in the NCI-60 cell line set, *Mol Cancer Ther* 5, 2606-2612.

Jacobs, D., Glossip, D., Xing, H., Muslin, A. J., and Kornfeld, K. (1999) Multiple docking sites on substrate proteins form a modular system that mediates recognition by ERK MAP kinase, *Genes Dev* 13, 163-175.

Jarvis R A & Patrick E A (1973) Clustering using a similarity measure based on shared nearest neighbors. *IEEE Trans. Comput.* C-22(11):1025-1034.

Johannessen, C. M., Boehm, J. S., Kim, S. Y., Thomas, S. R., Wardwell, L., Johnson, L. A., Emery, C. M., Stransky, N., Cogdill, A. P., Barretina, J., Caponigro, G., Hieronymus, H., Murray, R. R., Salehi-Ashtiani, K., Hill, D. E., Vidal, M., Zhao, J. J., Yang, X., Alkan, O., Kim, S., Harris, J. L., Wilson, C. J., Myer, V. E., Finan, P. M., Root, D. E., Roberts, T. M., Golub, T., Flaherty, K. T., Dummer, R., Weber, B. L., Sellers, W. R., Schlegel, R., Wargo, J. A., Hahn, W. C., and Garraway, L. A. (2010) COT drives resistance to RAF inhibition through MAP kinase pathway reactivation. *Nature* 468, 968-972.

Jorgensen W L, Chandrasekhar J, Madura J D, Impey R W, & Klein M L (1983) Comparison of simple potential functions for simulating liquid water. *J. Chem. Phys.* 79(2):926-935.

Joseph, E. W., Pratilas, C. A., Poulikakos, P. I., Tadi, M., Wang, W., Taylor, B. S., Halilovic, E., Persaud, Y., Xing, F., Viale, A., Tsai, J., Chapman, P. B., Bollag, G., Solit, D. B., and Rosen, N. The RAF inhibitor PLX4032 inhibits ERK signaling and tumor cell proliferation in a V600E BRAF-selective manner. *Proc Natl Acad Sci USA* 107, 14903-14908.

Jung, K. Y., Samadani, R., Chauhan, J., Nevels, K., Yap, J. L., Zhang, J., Worlikar, S., Lanning, M. E., Chen, L., Ensey, M., Shukla, S., Salmo, R., Heinzl, G., Gordon, C., Dukes, T., MacKerell, A. D., Jr., Shapiro, P., and Fletcher, S. (2013) Structural modifications of (Z)-3-(2-aminoethyl)-5-(4-ethoxybenzylidene)thiazolidine-2,4-dione that improve selectivity for inhibiting the proliferation of melanoma cells containing active ERK signaling, *Organic & biomolecular chemistry* 11, 3706-3732.

Kaoud, T. S., Park, H., Mitra, S., Yan, C., Tseng, C. C., Shi, Y., Jose, J., Taliaferro, J. M., Lee, K., Ren, P., Hong, J., and Dalby, K. N. (2012) Manipulating JNK signaling with (−)-zuonin A, *ACS chemical biology* 7, 1873-1883.

Karpen M E, Tobias D J, & Brooks C L, 3rd (1993) Statistical clustering techniques for the analysis of long molecular dynamics trajectories: analysis of 2.2-ns trajectories of YPGDV. *Biochemistry* 32(2):412-420.

Keshet, Y., and Seger, R. (2010) The MAP kinase signaling cascades: a system of hundreds of components regulates a diverse array of physiological functions, *Methods Mol Biol* 661, 3-38.

Kinoshita, T., Warizaya, M., Ohori, M., Sato, K., Neya, M., and Fujii, T. (2006) Crystal structure of human ERK2 complexed with a pyrazolo[3,4-c]pyridazine derivative, *Bioorg Med Chem Lett* 16, 55-58.

Kinoshita, T., Yoshida, I., Nakae, S., Okita, K., Gouda, M., Matsubara, M., Yokota, K., Ishiguro, H., and Tada, T. (2008) Crystal structure of human mono-phosphorylated ERK1 at Tyr204. *Biochem Biophys Res Commun* 377, 1123-1127.

Kohno, M., and Pouyssegur, J. (2006) Targeting the ERK signaling pathway in cancer therapy, *Ann Med* 38, 200-211.

Kolch, W., Kotwaliwale, A., Vass, K., and Janosch, P. (2002) The role of Raf kinases in malignant transformation. *Expert Rev Mol Med* 4, 1-18.

Krejci, P., Pejchalova, K., and Wilcox, W. R. (2007) Simple, mammalian cell-based assay for identification of inhibitors of the Erk MAP kinase pathway. *Invest New Drugs* 25, 391-395.

Krishnamurty, R., and Maly, D. J. (2010) Biochemical mechanisms of resistance to small-molecule protein kinase inhibitors, *ACS chemical biology* 5, 121-138.

Kuntz I D (1992) Structure-based strategies for drug design and discovery. *Science* 257(5073):1078-1082.

Kuntz I D, Blaney J M, Oatley S J, Langridge R, & Ferrin T E (1982) A geometric approach to macromolecule-ligand interactions. *J Mol Biol* 161(2):269-288.

Leach A R & Kuntz I D (1992) Conformational analysis of flexible ligands in macromolecular receptor sites. *J. Comput. Chem.* 13(6):730-748.

Lee, S., Warthaka, M., Yan, C., Kaoud, T. S., Ren, P., and Dalby, K. N. (2011) Examining docking interactions on ERK2 with modular peptide substrates. *Biochemistry* 50, 9500-9510.

Lee, T., Hoofnagle, A. N., Kabuyama, Y., Stroud, J., Min, X., Goldsmith, E. J., Chen, L., Resing, K. A., and Ahn, N. G. (2004) Docking motif interactions in MAP kinases revealed by hydrogen exchange mass spectrometry. *Mol Cell* 14, 43-55.

Levitt M & Lifson S (1969) Refinement of protein conformations using a macromolecular energy minimization procedure. *J Mol Biol* 46(2):269-279.

Lewis, T. S., Shapiro, P. S., Ahn, N. G. (1998) Signal transduction through MAP Kinase Cascades. *Advances in cancer research* 74, 49-139.

Li J B, Zhu T H, Cramer C J, & Truhlar D G (1998) New class IV charge model for extracting accurate partial charges from wave functions. *J. Phys. Chem. A* 102(10):1820-1831.

Li, Q., Al-Ayoubi, A., Guo, T., Zheng, H., Sarkar, A., Nguyen, T., Eblen, S. T., Grant, S., Kellogg, G. E., and Zhang, S. (2009) Structure-activity relationship (SAR) studies of 3-(2-amino-ethyl)-5-(4-ethoxy-benzylidene)-thiazolidine-2,4-dione: development of potential substrate-specific ERK1/2 inhibitors. *Bioorg Med Chem Lett* 19, 6042-6046.

Liao, Z., Wan, Y., Thomas, S. N., and Yang, A. J. (2012) IsoQuant: A Software Tool for SILAC-Based Mass Spectrometry Quantitation. *Anal Chem* In press.

Lipinski C A, Lombardo F, Dominy B W, & Feeney P J (1997) Experimental and computational approaches to estimate solubility and permeability in drug discovery and development settings. *Adv Drug Deliv Rev* 23(1-3):3-25.

Liu, S., Sun, J. P., Zhou, B., and Zhang, Z. Y. (2006) Structural basis of docking interactions between ERK2 and MAP kinase phosphatase 3, *Proc Natl Acad Sci USA* 103, 5326-5331.

Lopez-Bergami, P., Huang, C., Goydos, J. S., Yip, D., Bar-Eli, M., Herlyn, M., Smalley, K. S., Mahale, A., Eroshkin, A., Aaronson, S., and Ronai, Z. (2007) Rewired ERK-JNK signaling pathways in melanoma, *Cancer Cell* 11, 447-460.

Lowinger, T. B., Riedl, B., Dumas, J., and Smith, R. A. (2002) Design and discovery of small molecules targeting raf-1 kinase. *Current pharmaceutical design* 8, 2269-2278.

MacKerell A D, et al. (1998) All-atom empirical potential for molecular modeling and dynamics studies of proteins. *Journal of Physical Chemistry B* 102(18):3586-3616.

Mackerell A D, Jr., Feig M, & Brooks C L, 3rd (2004) Extending the treatment of backbone energetics in protein force fields: limitations of gas-phase quantum mechanics in reproducing protein conformational distributions in molecular dynamics simulations. *Journal of computational chemistry* 25(11):1400-1415.

MacKerell, A. D., Bashford, D., Bellott, M., Dunbrack, R. L., Evanseck, J. D., Field, M. J., Fischer, S., Gao, J., Guo, H., Ha, S., Joseph-McCarthy, D., Kuchnir, L., Kuczera, K., Lau, F. T. K., Mattos, C., Michnick, S., Ngo, T., Nguyen, D. T., Prodhom, B., Reiher, W. E., Roux, B., Schlenkrich, M., Smith, J. C., Stote, R., Straub, J., Watanabe, M., Wiorkiewicz-Kuczera, J., Yin, D., and Karplus, M. (1998) All-atom empirical potential for molecular modeling and dynamics studies of proteins, *Journal of Physical Chemistry B* 102, 3586-3616.

Mackerell, A. D., Jr., Feig, M., and Brooks, C. L., 3rd. (2004) Extending the treatment of backbone energetics in protein force fields: limitations of gas-phase quantum mechanics in reproducing protein conformational distributions in molecular dynamics simulations, *Journal of computational chemistry* 25, 1400-1415.

Markowitz, J., Chen, I., Gitti, R., Baldisseri, D. M., Pan, Y., Udan, R., Carrier, F., MacKerell, A. D., Jr., and Weber, D. J. (2004) Identification and characterization of small molecule inhibitors of the calcium-dependent S100B-p53 tumor suppressor interaction. *J Med Chem* 47, 5085-5093.

Martin, M. C., Allan, L. A., Mancini, E. J., and Clarke, P. R. (2008) The docking interaction of caspase-9 with ERK2 provides a mechanism for the selective inhibitory phosphorylation of caspase-9 at threonine 125. *J Biol Chem* 283, 3854-3865.

Matthews, M. M., Weber, D. J., Shapiro, P. S., Coop, A., and Mackerell, A. D., Jr. (2008) Inhibition of protein-protein interactions with low molecular weight compounds. *Current trends in medicinal chemistry* 5, 21-32.

McCubrey, J. A., Milella, M., Tafuri, A., Martelli, A. M., Lunghi, P., Bonati, A., Cervello, M., Lee, J. T., and Steelman, L. S. (2008) Targeting the Raf/MEK/ERK pathway with small-molecule inhibitors, *Curr Opin Investig Drugs* 9, 614-630.

McCubrey, J. A., Steelman, L. S., Chappell, W. H., Abrams, S. L., Wong, E. W., Chang, F., Lehmann, B., Terrian, D. M., Milella, M., Tafuri, A., Stivala, F., Libra, M., Basecke, J., Evangelisti, C., Martelli, A. M., and Franklin, R. A. (2007) Roles of the Raf/MEK/ERK pathway in cell growth, malignant transformation and drug resistance. *Biochim Biophys Acta* 1773, 1263-1284.

Mendelsohn, J., and Baselga, J. (2006) Epidermal growth factor receptor targeting in cancer. *Semin Oncol* 33, 369-385.

Milde-Langosch, K. (2005) The Fos family of transcription factors and their role in tumourigenesis, *Eur J Cancer* 41, 2449-2461.

Monje, P., Marinissen, M. J., and Gutkind, J. S. (2003) Phosphorylation of the carboxyl-terminal transactivation domain of c-Fos by extracellular signal-regulated kinase mediates the transcriptional activation of AP-1 and cellular transformation induced by platelet-derived growth factor, *Mol Cell Biol* 23, 7030-7043.

Morgillo, F., Cantile, F., Fasano, M., Troiani, T., Martinelli, E., and Ciardiello, F. (2009) Resistance mechanisms of tumour cells to EGFR inhibitors. *Clinical & translational oncology: official publication of the Federation of Spanish Oncology Societies and of the National Cancer Institute of Mexico* 11, 270-275.

Morris, E. J., Jha, S., Restaino, C. R., Dayananth, P., Zhu, H., Cooper, A., Carr, D., Deng, Y., Jin, W., Black, S., Long, B., Liu, J., Dinunzio, E., Windsor, W., Zhang, R., Zhao, S., Angagaw, M. H., Pinheiro, E. M., Desai, J., Xiao, L., Shipps, G., Hruza, A., Wang, J., Kelly, J., Paliwal, S., Gao, X., Babu, B. S., Zhu, L., Daublain, P., Zhang, L., Lutterbach, B. A., Pelletier, M. R., Philippar, U., Siliphaivanh, P., Witter, D., Kirschmeier, P., Bishop, W. R., Hicklin, D., Gilliland, D. G., Jayaraman, L., Zawel, L., Fawell, S., and Samatar, A. A. (2013) Discovery of a Novel ERK Inhibitor with Activity in Models of Acquired Resistance to BRAF and MEK Inhibitors, *Cancer discovery* 3, 742-750.

Murphy, L. O., Smith, S., Chen, R. H., Fingar, D. C., and Blenis, J. (2002) Molecular interpretation of ERK signal duration by immediate early gene products. *Nat Cell Biol* 4, 556-564.

Niesen, F. H., Berglund, H., and Vedadi, M. (2007) The use of differential scanning fluorimetry to detect ligand interactions that promote protein stability. *Nature protocols* 2, 2212-2221.

Nissink, J. W. M. (2009) Simple Size-Independent Measure of Ligand Efficiency, *Journal of Chemical Information and Modeling* 49, 1617-1622.

Oashi, T., Ringer, A. L., Raman, E. P., and Mackerell, A. D. (2011) Automated selection of compounds with physicochemical properties to maximize bioavailability and druglikeness. *J Chem Inf Model* 51, 148-158.

Ohori, M., Kinoshita, T., Okubo, M., Sato, K., Yamazaki, A., Arakawa, H., Nishimura, S., Inamura, N., Nakajima, H., Neya, M., Miyake, H., and Fujii, T. (2005) Identification of a selective ERK inhibitor and structural determination of the inhibitor-ERK2 complex, *Biochem Biophys Res Commun* 336, 357-363.

Okazaki, K., and Sagata, N. (1995) The Mos/MAP kinase pathway stabilizes c-Fos by phosphorylation and augments its transforming activity in NIH 3T3 cells, *Embo J* 14, 5048-5059.

Over, B., Wetzel, S., Grutter, C., Nakai, Y., Renner, S., Rauh, D., and Waldmann, H. (2013) Natural-product-derived fragments for fragment-based ligand discovery, *Nat Chem* 5, 21-28.

Pan Y, Huang N, Cho S, & MacKerell A D, Jr. (2003) Consideration of molecular weight during compound selection in virtual target-based database screening. *J. Chem. Inf. Comput. Sci.* 43(1):267-272.

Pao Y H (1989) Adaptive Pattern Recognition and Neural Networks (Addison-Wesley, Reading, Mass., U.S.A.).

Pearson, G., English, J. M., White, M. A., and Cobb, M. H. (2001) ERK5 and ERK2 cooperate to regulate NF-kappaB and cell transformation, *J Biol Chem* 276, 7927-7931.

Pearson, G., Robinson, F., Beers Gibson, T., Xu, B. E., Karandikar, M., Berman, K., and Cobb, M. H. (2001) Mitogen-activated protein (MAP) kinase pathways: regulation and physiological functions, *Endocr Rev* 22, 153-183.

Phillips J C, et al. (2005) Scalable molecular dynamics with NAMD. *J Comput Chem* 26(16):1781-1802.

Piserchio, A., Warthaka, M., Devkota, A. K., Kaoud, T. S., Lee, S., Abramczyk, O., Ren, P., Dalby, K. N., and Ghose, R. (2011) Solution NMR insights into docking interactions involving inactive ERK2. *Biochemistry* 50, 3660-3672.

Polychronopoulos, S., Verykokakis, M., Yazicioglu, M. N., Sakarellos-Daitsiotis, M., Cobb, M. H., and Mavrothalassitis, G. (2006) The transcriptional ETS2 repressor factor associates with active and inactive Erks through distinct FXF motifs, *J Biol Chem* 281, 25601-25611.

Poulikakos, P. I., and Rosen, N. (2011) Mutant BRAF melanomas—dependence and resistance, *Cancer cell* 19, 11-15.

Poulikakos, P. I., Zhang, C., Bollag, G., Shokat, K. M., and Rosen, N. RAF inhibitors transactivate RAF dimers and ERK signalling in cells with wild-type BRAF. *Nature* 464, 427-430.

Pouyssegur, J., Volmat, V., and Lenormand, P. (2002) Fidelity and spatio-temporal control in MAP kinase (ERKs) signalling, *Biochemical pharmacology* 64, 755-763.

Pozharski, E. (2010) Percentile-based spread: a more accurate way to compare crystallographic models, *Acta Crystallographica Section D* 66, 970-978.

Quinn, B. A., Dash, R., Azab, B., Sarkar, S., Das, S. K., Kumar, S., Oyesanya, R. A., Dasgupta, S., Dent, P., Grant, S., Rahmani, M., Curiel, D. T., Dmitriev, I., Hedvat, M., Wei, J., Wu, B., Stebbins, J. L., Reed, J. C., Pellecchia, M., Sarkar, D., and Fisher, P. B. (2011) Targeting Mcl-1 for the therapy of cancer. *Expert Opin Investig Drugs* 20, 1397-1411.

Rais, R., Acharya, C., Tririya, G., Mackerell, A. D., and Polli, J. E. (2010) Molecular switch controlling the binding of anionic bile acid conjugates to human apical sodium-dependent bile acid transporter. *J Med Chem* 53, 4749-4760.

Raman E P, Yu W, Guvench O, & Mackerell A D (2011) Reproducing crystal binding modes of ligand functional groups using Site-Identification by Ligand Competitive Saturation (SILCS) simulations. *J Chem Inf Model* 51(4):877-896.

Raman, M., Chen, W., and Cobb, M. H. (2007) Differential regulation and properties of MAPKs, *Oncogene* 26, 3100-3112.

Reuter, C. W., Morgan, M. A., and Bergmann, L. (2000) Targeting the Ras signaling pathway: a rational, mechanism-based treatment for hematologic malignancies? *Blood* 96, 1655-1669.

Rexer, B. N., Engelman, J. A., and Arteaga, C. L. (2009) Overcoming resistance to tyrosine kinase inhibitors: lessons learned from cancer cells treated with EGFR antagonists. *Cell Cycle* 8, 18-22.

Reynolds, C. H., Tounge, B. A., and Bembenek, S. D. (2008) Ligand Binding Efficiency: Trends, Physical Basis, and Implications, *Journal of Medicinal Chemistry* 51, 2432-2438.

Robinson, F. L., Whitehurst, A. W., Raman, M., and Cobb, M. H. (2002) Identification of novel point mutations in ERK2 that selectively disrupt binding to MEK1, *J Biol Chem* 277, 14844-14852.

Ryckaert J P, Ciccotti G, & Berendsen H J C (1977) Numerical integration of the cartesian equations of motion of a system with constraints: molecular dynamics of n-alkanes. *J Comput Phys* 23(3):219-341.

Shapiro, P. S., Whalen, A. M., Tolwinski, N. S., Wilsbacher, J., Froelich-Ammon, S. J., Garcia, M., Osheroff, N., and Ahn, N. G. (1999) Extracellular signal-regulated kinase activates topoisomerase IIalpha through a mechanism independent of phosphorylation. *Mol Cell Biol* 19, 3551-3560.

Sharrocks, A. D., Yang, S. H., and Galanis, A. (2000) Docking domains and substrate-specificity determination for MAP kinases, *Trends in biochemical sciences* 25, 448-453.

Sheridan, D. L., Kong, Y., Parker, S. A., Dalby, K. N., and Turk, B. E. (2008) Substrate discrimination among mitogen-activated protein kinases through distinct docking sequence motifs, *J Biol Chem* 283, 19511-19520.

Shimamura, A., Ballif, B. A., Richards, S. A., and Blenis, J. (2000) Rsk1 mediates a MEK-MAP kinase cell survival signal. *Curr Biol* 10, 127-135.

Stebbins, J. L., De, S. K., Machleidt, T., Becattini, B., Vazquez, J., Kuntzen, C., Chen, L. H., Cellitti, J. F., Riel-Mehan, M., Emdadi, A., Solinas, G., Karin, M., and Pellecchia, M. (2008) Identification of a new JNK inhibitor targeting the JNK-JIP interaction site, *Proc Natl Acad Sci USA* 105, 16809-16813.

Steinbach P J & Brooks B R (1994) New Spherical-Cutoff Methods for Long-Range Forces in Macromolecular Simulation. *Journal of Computational Chemistry* 15(7): 667-683.

Tanimoto T T (1957) *IBM Internal Report, Nov.*

Tanoue, T., Adachi, M., Moriguchi, T., and Nishida, E. (2000) A conserved docking motif in MAP kinases common to substrates, activators and regulators, *Nat. Cell Biol.* 2, 110-116.

Tanoue, T., Maeda, R., Adachi, M., and Nishida, E. (2001) Identification of a docking groove on ERK and p38 MAP kinases that regulates the specificity of docking interactions, *Embo J* 20, 466-479.

Tawbi, H., and Nimmagadda, N. (2009) Targeted therapy in melanoma. *Biologics* 3, 475-484.

Tipton, K. F., Boyce, S., O'Sullivan, J., Davey, G. P., and Healy, J. (2004) Monoamine oxidases: certainties and uncertainties. *Curr Med Chem* 11, 1965-1982.

Treisman, R. (1994) Ternary complex factors: growth factor regulated transcriptional activators, *Curr Opin Genet Dev* 4, 96-101.

Tsai, J., Lee, J. T., Wang, W., Zhang, J., Cho, H., Mamo, S., Bremer, R., Gillette, S., Kong, J., Haass, N. K., Sproesser, K., Li, L., Smalley, K. S., Fong, D., Zhu, Y. L., Marimuthu, A., Nguyen, H., Lam, B., Liu, J., Cheung, I., Rice, J., Suzuki, Y., Luu, C., Settachatgul, C., Shellooe, R., Cantwell, J., Kim, S. H., Schlessinger, J., Zhang, K. Y., West, B. L., Powell, B., Habets, G., Zhang, C., Ibrahim, P. N., Hirth, P., Ards, D. R., Herlyn, M., and Bollag, G. (2008) Discovery of a selective inhibitor of oncogenic BRaf kinase with potent antimelanoma activity. Proc Natl Acad Sci USA 105, 3041-3046.

Tsurumi, C., Ishida, N., Tamura, T., Kakizuka, A., Nishida, E., Okumura, E., Kishimoto, T., Inagaki, M., Okazaki, K., Sagata, N., and et al. (1995) Degradation of c-Fos by the 26S proteasome is accelerated by c-Jun and multiple protein kinases, Mol Cell Biol 15, 5682-5687.

Tzarum, N., Eisenberg-Domovich, Y., Gills, J. J., Dennis, P. A., and Livnah, O. (2012) Lipid Molecules Induce p38α Activation via a Novel Molecular Switch, Journal of Molecular Biology 424, 339-353.

Tzarum, N., Komornik, N., Ben Chetrit, D., Engelberg, D., and Livnah, O. (2013) DEF pocket in p38alpha facilitates substrate selectivity and mediates autophosphorylation, J Biol Chem 288, 19537-19547.

Vanommeslaeghe, K., and MacKerell, A. D., Jr. (2012) Automation of the CHARMM General Force Field (CGenFF) I: bond perception and atom typing, J Chem Inf Model 52, 3144-3154.

Vanommeslaeghe, K., Hatcher, E., Acharya, C., Kundu, S., Zhong, S., Shim, J., Darian, E., Guvench, O., Lopes, P., Vorobyov, I., and MacKerell, J., A. D. (2010) CHARMM General Force Field (CGenFF): A force field for drug-like molecules compatible with the CHARMM all-atom additive biological force fields. J. Comp. Chem. 31, 671-690, 2010.

Vanommeslaeghe, K., Raman, E. P., and MacKerell, A. D., Jr. (2012) Automation of the CHARMM General Force Field (CGenFF) II: assignment of bonded parameters and partial atomic charges, J Chem Inf Model 52, 3155-3168.

Verde, P., Casalino, L., Talotta, F., Yaniv, M., and Weitzman, J. B. (2007) Deciphering AP-1 function in tumorigenesis: fra-ternizing on target promoters, Cell Cycle 6, 2633-2639.

Vinciguerra, M., Vivacqua, A., Fasanella, G., Gallo, A., Cuozzo, C., Morano, A., Maggiolini, M., and Musti, A. M. (2004) Differential phosphorylation of c-Jun and JunD in response to the epidermal growth factor is determined by the structure of MAPK targeting sequences, J Biol Chem 279, 9634-9641.

von Kriegsheim, A., Baiocchi, D., Birtwistle, M., Sumpton, D., Bienvenut, W., Morrice, N., Yamada, K., Lamond, A., Kalna, G., Orton, R., Gilbert, D., and Kolch, W. (2009) Cell fate decisions are specified by the dynamic ERK interactome. Nat Cell Biol 11, 1458-1464.

Wagle, N., Emery, C., Berger, M. F., Davis, M. J., Sawyer, A., Pochanard, P., Kehoe, S. M., Johannessen, C. M., Maccomaill, L. E., Hahn, W. C., Meyerson, M., and Garraway, L. A. (2011) Dissecting therapeutic resistance to RAF inhibition in melanoma by tumor genomic profiling. J Clin Oncol 29, 3085-3096.

Wagner, E. F. Bone development and inflammatory disease is regulated by AP-1 (Fos/Jun). Ann Rheum Dis 69 Suppl 1, i86-88.

Wilhelm, S. M., Carter, C., Tang, L., Wilkie, D., McNabola, A., Rong, H., Chen, C., Zhang, X., Vincent, P., McHugh, M., Cao, Y., Shujath, J., Gawlak, S., Eveleigh, D., Rowley, B., Liu, L., Adnane, L., Lynch, M., Auclair, D., Taylor, I., Gedrich, R., Voznesensky, A., Riedl, B., Post, L. E., Bollag, G., and Trail, P. A. (2004) BAY 43-9006 exhibits broad spectrum oral antitumor activity and targets the RAF/MEK/ERK pathway and receptor tyrosine kinases involved in tumor progression and angiogenesis. Cancer Res 64, 7099-7109.

Willems, A., Gauger, K., Henrichs, C., and Harbeck, N. (2005) Antibody therapy for breast cancer. Anticancer research 25, 1483-1489.

Word J M, Lovell S C, Richardson J S, & Richardson D C (1999) Asparagine and glutamine: using hydrogen atom contacts in the choice of side-chain amide orientation. J Mol Biol 285(4):1735-1747.

Word, J. M., Lovell, S. C., Richardson, J. S., and Richardson, D. C. (1999) Asparagine and glutamine: using hydrogen atom contacts in the choice of side-chain amide orientation, J Mol Biol 285, 1735-1747.

Yap, J. L., Worlikar, S., MacKerell, A. D., Jr., Shapiro, P., and Fletcher, S. (2011) Small-molecule inhibitors of the ERK signaling pathway: Towards novel anticancer therapeutics, Chem Med Chem 6, 38-48.

Yeh, J. J., Routh, E. D., Rubinas, T., Peacock, J., Martin, T. D., Shen, X. J., Sandler, R. S., Kim, H. J., Keku, T. O., and Der, C. J. (2009) KRAS/BRAF mutation status and ERK1/2 activation as biomarkers for MEK1/2 inhibitor therapy in colorectal cancer. Mol Cancer Ther 8, 834-843.

Yu W M, Guvench O, Mackerell A D, & Qu C K (2008) Identification of small molecular weight inhibitors of Src homology 2 domain-containing tyrosine phosphatase 2 (SHP-2) via in silico database screening combined with experimental assay. J. Med. Chem. 51(23):7396-7404.

Zhang F, Strand A, Robbins D, Cobb M H, & Goldsmith E J (1994) Atomic structure of the MAP kinase ERK2 at 2.3 A resolution [see comments]. Nature 367(6465):704-711.

Zhang, J., Zhou, B., Zheng, C. F., and Zhang, Z. Y. (2003) A bipartite mechanism for ERK2 recognition by its cognate regulators and substrates, J Biol Chem 278, 29901-29912.

Zheng, L., Chen, M., and Yang, W. (2009) Simultaneous escaping of explicit and hidden free energy barriers: application of the orthogonal space random walk strategy in generalized ensemble based conformational sampling. J Chem Phys 130, 234105.

Zhong S & MacKerell A D, Jr. (2007) Binding response: a descriptor for selecting ligand binding site on protein surfaces. J Chem Inf Model 47(6):2303-2315.

Zhong, S., Chen, X., Zhu, X., Dziegielewska, B., Bachman, K. E., Ellenberger, T., Ballin, J. D., Wilson, G. M., Tomkinson, A. E., and MacKerell, A. D., Jr. (2008) Identification and validation of human DNA ligase inhibitors using computer-aided drug design. J Med Chem 51, 4553-4562.

Zhong, S., Macias, A. T., and MacKerell, A. D., Jr. (2007) Computational identification of inhibitors of protein-protein interactions. Curr Top Med Chem 7, 63-82.

Zhou, T., Sun, L., Humphreys, J., and Goldsmith, E. J. (2006) Docking interactions induce exposure of activation loop in the MAP kinase ERK2, Structure 14, 1011-1019.

Zuniga, A., Torres, J., Ubeda, J., and Pulido, R. (1999) Interaction of mitogen-activated protein kinases with the kinase interaction motif of the tyrosine phosphatase PTP-SL provides substrate specificity and retains ERK2 in the cytoplasm, J Biol Chem 274, 21900-21907.

The invention claimed is:
1. A compound, having the formula A-1:
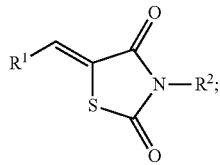
wherein A-1 is one of the following compounds:
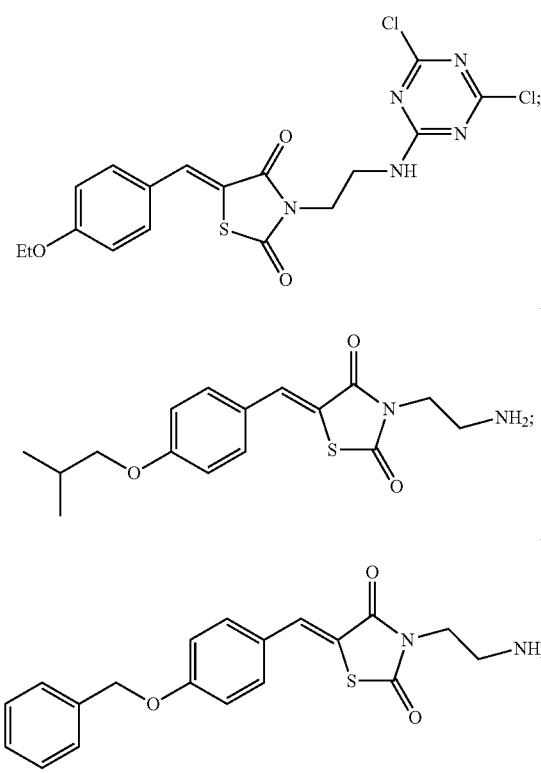
2. A composition, comprising the compound of claim 1 and a pharmaceutically acceptable carrier.
3. A compound, having the formula E-2:
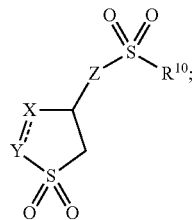
wherein E-2 is one of the following compounds:
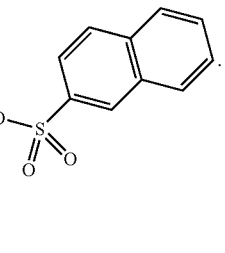
4. A composition, comprising the compound of claim 3 and a pharmaceutically acceptable carrier.
* * * * *